United States Patent
Zhu et al.

(10) Patent No.: US 12,297,233 B2
(45) Date of Patent: *May 13, 2025

(54) FCRN-TARGETED MUCOSAL VACCINATION AGAINST INFLUENZA INFECTIONS

(71) Applicant: UNIVERSITY OF MARYLAND, COLLEGE PARK, College Park, MD (US)

(72) Inventors: Xiaoping Zhu, Clarksville, MD (US); Susan Park-Ochsner, Towson, MD (US); Weizhong Li, College Park, MD (US)

(73) Assignee: University of Maryland, College Park, College Park, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/163,145

(22) Filed: Feb. 1, 2023

(65) Prior Publication Data

US 2023/0295240 A1 Sep. 21, 2023

Related U.S. Application Data

(63) Continuation of application No. 16/373,272, filed on Apr. 2, 2019, now Pat. No. 11,591,371.

(60) Provisional application No. 62/651,522, filed on Apr. 2, 2018.

(51) Int. Cl.
| | | |
|---|---|---|
| C07K 14/005 | (2006.01) | |
| A61K 39/145 | (2006.01) | |
| A61P 31/16 | (2006.01) | |
| A61K 39/00 | (2006.01) | |

(52) U.S. Cl.
CPC .......... *C07K 14/005* (2013.01); *A61K 39/145* (2013.01); *A61P 31/16* (2018.01); *A61K 2039/543* (2013.01); *A61K 2039/55561* (2013.01); *A61K 2039/55572* (2013.01); *C07K 2319/30* (2013.01); *C12N 2760/16022* (2013.01); *C12N 2760/16034* (2013.01)

(58) Field of Classification Search
None
See application file for complete search history.

(56) References Cited

U.S. PATENT DOCUMENTS

| | | |
|---|---|---|
| 9,238,683 B2 | 1/2016 | Zhu |
| 10,188,724 B2 | 1/2019 | Zhu |
| 11,375,317 B2 | 7/2022 | Zhu |
| 11,376,317 B2 | 7/2022 | Balint et al. |
| 11,591,371 B2 | 2/2023 | Zhu et al. |
| 2007/0009523 A1 | 1/2007 | Presta |
| 2011/0086058 A1 | 4/2011 | Jiang |
| 2013/0164286 A1 | 6/2013 | Chou |
| 2015/0079121 A1 | 3/2015 | Weiner et al. |
| 2015/0125473 A1 | 5/2015 | Burt et al. |
| 2018/0244756 A1 | 8/2018 | Graham et al. |
| 2019/0060440 A1 | 2/2019 | Zhu et al. |
| 2019/0359655 A1 | 11/2019 | Zhu et al. |
| 2022/0401547 A1 | 12/2022 | Zhu et al. |
| 2023/0295240 A1 | 9/2023 | Zhu et al. |

FOREIGN PATENT DOCUMENTS

| | | |
|---|---|---|
| EP | 18851829.4 | 10/2018 |
| WO | WO/2019/046859 A1 | 3/2019 |
| WO | WO-2019/046864 A1 | 3/2019 |

OTHER PUBLICATIONS

Allie SR, Randall TD (2017) Pulmonary immunity to viruses. Clin Sci (Lond). 131:1737-1762.
Iwasaki A, Foxman EF, Molony RD (2017) Early local immune defenses in the respiratory tract. Nat Rev Immunol. 17:7-20.
Barría MI, et al (2013) Localized mucosal response to intranasal live attenuated influenza vaccine in adults. J Infect Dis. 207:115-24.
Chiu C, Openshaw PJ (2015) Antiviral B cell and T cell immunity in the lungs. Nat Immunol. 16:18-26.
Mueller SN, Gebhardt T, Carbone FR, Heath WR (2013) Memory T cell subsets, migration patterns, and tissue residence. Annu Rev Immunol. 31:137-61.
Turner DL, Farber DL (2014) Mucosal resident memory CD4 T cells in protection and immunopathology. Front Immunol. 14;5:331.
Iijima N, Iwasaki A (2015) *Tissue instruction for migration and retention of TRM cells*. Trends Immunol. 36:556-64.
Hodge LM, et al. (2001) Immunoglobulin A (IgA) responses and IgE-associated inflammation along the respiratory tract after mucosal but not systemic immunization. Infect Immun. 69:2328-38.
Brokstad KA (2002) Parenteral vaccination against influenza does not induce a local antigen-specific immune response in the nasal mucosa. J Infect Dis. 185:878-84.
Muszkat M, et al. (2003) *Local and systemic immune response in nursing-home elderly following intranasal or intramuscular immunization with inactivated influenza vaccine*. Vaccine. 21:1180-6.
Minne A, et al. (2007) *The delivery site of a monovalent influenza vaccine within the respiratory tract impacts on the immune response*. Immunology. 122:316-25.

(Continued)

*Primary Examiner* — Benjamin P Blumel
(74) *Attorney, Agent, or Firm* — BALLARD SPAHR LLP

(57) ABSTRACT

Disclosed are peptides comprising a monomeric Fc fragment of an immunoglobulin recognized by a neonatal receptor (FcRn); an influenza HA protein; and a trimerization domain. Disclosed are compositions comprising one or more of the peptides described herein. Disclosed are nucleic acid sequences capable of encoding any one of the peptides described herein. Disclosed are methods for eliciting a protective immune response against influenza comprising administering to a subject an effective amount of a composition comprising a monomeric Fc fragment of an immunoglobulin recognized by a FcRn; an influenza HA protein; and a trimerization domain, wherein the administering is to a mucosal epithelium. Disclosed are methods of treating a subject exposed to influenza or at risk of being exposed to influenza comprising administering to the subject an effective amount of a composition comprising a monomeric Fc fragment of an immunoglobulin recognized by a FcRn; an influenza HA protein; and a trimerization domain, wherein the administering is to a mucosal epithelium.

22 Claims, 22 Drawing Sheets

Specification includes a Sequence Listing.

(56) References Cited

OTHER PUBLICATIONS

Iwasaki A. (2016) Exploiting Mucosal Immunity for Antiviral Vaccines. Annu Rev Immunol. 34:575-608.
McMaster SR, et al. (2018) Pulmonary antigen encounter regulates the establishment of tissue-resident CD8 memory T cells in the lung airways and parenchyma. Mucosal Immunol. 11:1071-8.
Dickinson BL, et al. (1999) *Bidirectional FcRn-dependent IgG transport in a polarized human intestinal epithelial cell line*. J Clin Invest. 104:903-11.
Spiekermann GM, et al. (2002) Receptor-mediated immunoglobulin G transport across mucosal barriers in adult life: functional expression of FcRn in the mammalian lung. J Exp Med. 196:303-10.
Li Z, et al. (2011) Transfer of IgG in the female genital tract by MHC class I-related neonatal Fc receptor (FcRn) confers protective immunity to vaginal infection. Proc Natl Acad Sci U S A. 108:4388-93.
Yoshida M, et al. (2006) Neonatal Fc receptor for IgG regulates mucosal immune responses to luminal bacteria. J Clin Invest. 116:2142-2151.
Bai Y, et al (2011) Intracellular neutralization of viral infection in polarized epithelial cells by neonatal Fc receptor (FcRn)-mediated IgG transport. Proc Natl Acad Sci U S A. 108:18406-11.
Ko SY, et al. (2014) Enhanced neonatal Fc receptor function improves protection against primate SHIV infection. Nature. 514:642-5.
Vaughn DE, Bjorkman PJ. (1998) Structural basis of pH-dependent Ab binding by the neonatal Fc receptor. Structure. 6:63-73.
Roopenian DC Akilesh S (2007) FcRn: the neonatal Fc receptor comes of age. Nat Rev Immunol. 7:715-25.
Zhirnov OP, Ikizler MR, Wright PF (2002) Cleavage of influenza a virus hemagglutinin in human respiratory epithelium is cell associated and sensitive to exogenous antiproteases. J Virol. 76:8682-9.
Kim JK, Tsen MF, Ghetie V, Ward ES (1994) Localization of the site of the murine IgGI molecule that is involved in binding to the murine intestinal Fc receptor. Eur J Immunol. 24:2429-34.
Duncan AR, Winter G (1988) The binding site for Clq on IgG. Nature. 332:738-40.
Letarov AV, Londer YY, Boudko SP, Mesyanzhinov VV (1999) The carboxy-terminal domain initiates trimerization of bacteriophage T4 fibritin. Biochemistry (Mosc). 64:817-23.
Krammer F, et al. (2012) *A carboxy-terminal trimerization domain stabilizes conformational epitopes on the stalk domain of soluble recombinant hemagglutinin substrates*. PLoS One. 7:e43603.
Weldon WC, et al. (2010) Enhanced immunogenicity of stabilized trimeric soluble influenza hemagglutinin. PLoS One. 5. pii: e12466.
Ekiert DC, et al. (2011) A highly conserved neutralizing epitope on group 2 influenza A viruses. Science. 333:843-50.
Tan GS, et al. (2012) A pan-H1 anti-hemagglutinin monoclonal Ab with potent broad-spectrum efficacy in vivo. J Virol. 86:6179-88.
Krammer F, et al. (2014) Assessment of influenza virus hemagglutinin stalk-based immunity in ferrets. J Virol. 88:3432-42.
Friesen RH, et al. (2014) A common solution to group 2 influenza virus neutralization. Proc Natl Acad Sci U S A. Jan. 7, 2014;111(1):445-50.
Iho S, Maeyama J, Suzuki F (2015) CpG oligodeoxynucleotides as mucosal adjuvants. Hum Vaccin Immunother. 11:755-60.
Renegar KB, Small PA Jr., Boykins LG, Wright PF (2004) Role of IgA versus IgG in the control of influenza viral infection in the murine respiratory tract. J Immunol. 173:1978-86.
Slifka MK, Antia R, Whitmire JK, Ahmed R (1998) Humoral immunity due to long-lived plasma cells. Immunity. 8:363-72.
Sallusto F, Lanzavecchia A, Araki K, Ahmed R (2010) From vaccines to memory and back. Immunity. 33:451-63.
Zens KD, Chen JK, Farber DL (2016) Vaccine-generated lung tissue-resident memory T cells provide heterosubtypic protection to influenza infection. JCI Insight. 1. pii: e85832.
Pizzolla A, et al. (2017) Resident memory CD8+T cells in the upper respiratory tract prevent pulmonary influenza virus infection. Sci Immunol. 2. pii: eaam6970.

Qiao SW, et al. (2008) Dependence of Ab mediated presentation of antigen on FcRn. Proc Natl Acad Sci U S A. 105:9337-42.
Liu X, et al. (2011) The neonatal FcR-mediated presentation of immune-complexed antigen is associated with endosomal and phagosomal pH and antigen stability in macrophages and dendritic cells. J Immunol. 186:4674-86.
Baker K, et al (2011) Neonatal Fc receptor for IgG (FcRn) regulates cross-presentation of IgG immune complexes by CD8-CD11b+ dendritic cells. Proc Natl Acad Sci U S A. 108:9927-32.
Major D, et al. (2015) Intranasal vaccination with a plant-derived H5 Ha vaccine protects mice and ferrets against highly pathogenic avian influenza virus challenge. Hum Vaccin Immunother. 11:1235-43.
Kubo T, et al. (2015) CpG-DNA enhances the tight junction integrity of the bronchial epithelial cell barrier. J Allergy Clin Immunol. 136:1413-6.
Van Riet E, Ainai A, Suzuki T, Hasegawa H (2012) Mucosal IgA responses in influenza virus infections; thoughts for vaccine design. Vaccine. 30:5893-900.
Brown DM, et al. (2012) Multifunctional CD4 cells expressing gamma interferon and perforin mediate protection against lethal influenza virus infection. J Virol. 86:6792-803.
Houser K, Subbarao K (2015) Influenza vaccines: challenges and solutions. Cell Host Microbe. 17:295-300.
Laidlaw BJ, et al. (2014) CD4+ T cell help guides formation of CD103+ lung-resident memory CD8+ T cells during influenza viral infection. Immunity. 41:633-45.
McMaster SR, Wilson JJ, Wang H, Kohlmeier JE (2015) Airway-Resident Memory CD8 T Cells Provide Antigen-Specific Protection against Respiratory Virus Challenge through Rapid IFN-β Production. J Immunol. 195:203-9.
Slütter B, et al. (2017) Dynamics of influenza-induced lung-resident memory T cells underlie waning heterosubtypic immunity. Sci Immunol. 2. pii: eaag2031.
Erbelding EJ, et al. (2018) A Universal Influenza Vaccine: The Strategic Plan for the National Institute of Allergy and Infectious Diseases. J Infect Dis. 218:347-54.
Krammer F, Pica N, Hai R, Margine I, Palese P (2013) Chimeric hemagglutinin influenza virus vaccine constructs elicit broadly protective stalk-specific Abs. J Virol. 87:6542-50.
Krammer F, Palese P. (2015) Advances in the development of influenza virus vaccines. Nat Rev Drug Discov. 14:167-82.
Ermler ME, et al. (2017) Chimeric Hemagglutinin Constructs Induce Broad Protection against Influenza B Virus Challenge in the Mouse Model. J Virol. 91: pii: e00286-17.
Margine I, et al. (2013) Hemagglutinin stalk-based universal vaccine constructs protect against group 2 influenza A viruses. J Virol. 87:10435-46.
Wu T, et al. (2014) Lung-resident memory CD8 T cells (TRM) are indispensable for optimal cross-protection against pulmonary virus infection. J Leukoc Biol. 95:215-24.
Ye L, Zeng R, Bai Y, Roopenian DC, Zhu X (2011) Efficient mucosal vaccination mediated by the neonatal Fc receptor. Nat Biotechnol. 29:158-63.
Frey A, Di Canzio J, Zurakowski D (1998) A statistically defined endpoint titer determination method for immunoassays. J. Immunol. Methods, 221:35-41.
Hirst GK (1942) The Quantitative Determination of Influenza Virus and Abs by Means of Red Cell Agglutination. J. Exp. Med. 75:49-64.
Oh S, et al. (2009) Neutralizing monoclonal Abs to different clades of Influenza A H5N1 viruses. J Virol Methods. 157:161-7.
McLellan et al. Structure-based design of a fusion glycoprotein vaccine for respiratory syncytial virus. Science. Vol 342, Nov. 2013, pp. 592-598.
Lu et al. A neonatal Fc receptor-targeted mucosal vaccine strategy effectively induces HIV-1 antigen-specific immunity to genital infection. J Virol. Oct. 2011. pp. 10542-10553, vol. 85, No. 20.
U.S. Appl. No. 16/373,272, filed Apr. 2, 2019, Xiaoping Zhu.
U.S. Appl. No. 62/651,522, filed Apr. 2, 2018, Xiaoping Zhu.
U.S. Appl. No. 17/187,214, filed Feb. 26, 2021, Xiaoping Zhu.
U.S. Appl. No. 17/831,928, filed Jun. 3, 2022, Xiaoping Zhu.
U.S. Appl. No. 18/517,578, filed Nov. 22, 2023, Xiaoping Zhu.

(56) References Cited

OTHER PUBLICATIONS

Afkhami, S et al. Respiratory mucosal delivery of next-generation COVID-19 vaccine provides robust protection against both ancestral and variant strains of SARS-CoV-2. Cell 185, 896-915.e19 (2022).
Al-Aly Z, Bowe B, & Xie Y. Long COVID after breakthrough SARS-CoV-2 infection. Nat. Med. 28, 1461-1467 (2022).
Allie, S. R. et al. The establishment of resident memory B cells in the lung requires local antigen encounter. Nat. Immunol. 20, 97-108 (2019).
Andrews, M. G. et al. Tropism of SARS-CoV-2 for human cortical astrocytes. Proc. Natl. Acad. Sci. USA. 119(30), pp. 1-12, e2122236119 (2022).
Bauer, L. et al. The neuroinvasiveness, neurotropism, and neurovirulence of SARS-CoV-2. Trends Neurosci. 45(5):358-368 (2022).
Berneman A, Belec L, Fischetti VA, Bouvet JP. 1998. The specificity patterns of human immunoglobulin G antibodies in serum differ from those in autologous secretions. Infect Immun. 66:4163-4168.
Boukhvalova MS, Blanco JC. 2013. The cotton rat Sigmodon hispidus model of respiratory syncytial virus infection. Curr Top Microbiol Immunol. 372:347-58.
Castilow EM, Varga SM. 2008. Overcoming T cell-mediated immunopathology to achieve safe RSV vaccination. Future Virol. 3:445-454.
Chandrashekar, A. et al. Vaccine protection against the SARS-CoV-2 Omicron variant in macaques. Cell 185, 1549-1555.e11 (2022).
Cullen LM, Blanco JC, Morrison TG. 2015. Cotton rat immune responses to virus-like particles containing the pre-fusion form of respiratory syncytial virus fusion protein. J Transl Med. 13:350.
Dan, J. M. et al. Immunological memory to SARS-CoV-2 assessed for up to 8 months after infection. Science 371, eabf4063 (2021).
Dekkers, G. et al. Affinity of human IgG subclasses to mouse Fc gamma receptors. MAbs 9, 767-773 (2017).
Du, L. et al. The spike protein of SARS-CoV—a target for vaccine and therapeutic development. Nat. Rev. Microbiol. 7, 226-236 (2009).
Fischer, H. & Widdicombe, J. H. Mechanisms of acid and base secretion by the airway epithelium. J. Membr. Biol. 211, 139-150 (2006).
Fröberg, J. et al. SARS-CoV-2 mucosal antibody development and persistence and their relation to viral load and COVID-19 symptoms. Nat. Commun. 12, 5621 (2021).
Garg R, Latimer L, Simko E, Gerdts V, Potter A, van den Hurk Sv. Induction of mucosal immunity and protection by intranasal immunization with a respiratory syncytial virus subunit vaccine formulation. J Gen Virol. Feb. 2014;95(Pt 2):301-6.
Garg R, Theaker M, Martinez EC, van Drunen Littel-van den Hurk S. A single intranasal immunization with a subunit vaccine formulation induces higher mucosal IgA production than live respiratory syncytial virus. Virology. Dec. 2016;499:288-297.
Gebril A, Alsaadi M, Acevedo R, Mullen AB, Ferro VA. 2012. Optimizing efficacy of mucosal vaccines. Expert Rev Vaccines. 11:1139-55.
Golden, J. W. et al. Hamsters Expressing Human Angiotensin-Converting Enzyme 2 Develop Severe Disease following Exposure to SARS-CoV-2. mBio 13, e0290621(2022).
Graham BS, Modjarrad K, McLellan JS. 2015. Novel antigens for RSV vaccines. Curr Opin Immunol. 35:30-8.
Grau-Expósito, J. et al. Peripheral and lung resident memory T cell responses against SARS-CoV-2. Nat. Commun. 12, 3010 (2021).
Hartwell, B. L. et al. Intranasal vaccination with lipid-conjugated immunogens promotes antigen transmucosal uptake to drive mucosal and systemic immunity. Sci. Transl. Med 14(654), pp. 1-14, eabn1413 (2022).
Hassan, A. O. et al. A Single-Dose Intranasal ChAd Vaccine Protects Upper and Lower Respiratory Tracts against SARS-CoV-2. Cell 183, 169-184, e13 (2020).
He, W. et al. FcRn-mediated antibody transport across epithelial cells revealed by electron tomography. Nature 455, 542-546 (2008).
Holmgren J, Svennerholm AM. 2012. Vaccines against mucosal infections. Curr Opin Immunol. 24:343-53.
Hou, Y. J. et al. SARS-CoV-2 reverse genetics reveals a variable infection gradient in the respiratory tract. Cell 182, 429-446, e14 (2020).
http://www.grandviewresearch.com/press-release/global-vaccine-market.
https://seekingalpha.com/article/4061495-novavax-will-ride-high-rsv-vaccine-wave-2017.
https://www.cdc.gov/features/rsv/.
https://www.fiercepharma.com/vaccines/bavarian-nordic-reports-positive-rsv-vaccine-top-line-phase-2-data.
https://www.fiercepharma.com/vaccines/novavax-still-gunning-for-first-to-market-status-rsv-ceo.
Hunter, P. Viral diseases and the brain: Long COVID puts the spotlight on how viral infections affect the brain. EMBO Rep. 23, e54342 (2022).
Idusogie, E, E, et al. Mapping of the C1q binding site on rituxan, a chimeric antibody with a human IgG1 Fc. J. Immunol. 164, 4178-4184 (2000).
Jeyanathan, M. et al. Immunological considerations for COVID-19 vaccine strategies. Nat. Rev. Immunol. 20, 615-632 (2020).
Johnson TR, Rangel D, Graham BS, Brough DE, Gall JG. Genetic vaccine for respiratory syncytial virus provides protection without disease potentiation. Mol Ther. Jan. 2014;22(1):196-205.
Johnson TR, Rao S, Seder RA, Chen M, Graham BS. 2009. TLR9 agonist, but not TLR7/8, functions as an adjuvant to diminish FI-RSV vaccine-enhanced disease, while either agonist used as therapy during primary RSV infection increases disease severity. Vaccine. 27:3045-52.
Joyce MG, et al. 2016. Iterative structure-based improvement of a fusion-glycoprotein vaccine against RSV. Nat Struct Mol Biol. 23:811-20.
Kinnear E, Lambert L, McDonald JU, Cheeseman HM, Caproni LJ, Tregoning JS. Airway T cells protect against RSV infection in the absence of antibody. Mucosal Immunol. May 24, 2017.
Krarup A, et al., 2015. A highly stable prefusion RSV F vaccine derived from structural analysis of the fusion mechanism. Nat Commun. 6:8143.
Liang et al., Enhanced Neutralizing Antibody Response Induced by Respiratory Syncytial Virus Prefusion F Protein Expressed by a Vaccine Candidate. J Virol. 2015, vol. 89(18), p. 9499-510.
Lipsitch, M., Krammer, F., Regev-Yochay, G., Lustig, Y., & Balicer, R.D. SARS-CoV-2 breakthrough infections in vaccinated individuals: measurement, causes and impact. Nat. Rev. Immunol. 22, 57-65 (2022).
Lu L, Palaniyandi S, Zeng R, Bai Y, Liu X, Wang Y, Pauza CD, Roopenian DC, Zhu X. 2011. An FcRn-targeted mucosal vaccine strategy effectively induces HIV-1 antigen-specific immunity to genital infection. J. Virol. 85:10542-10553.
Lund, F. E. & Randall, T. D. Scent of a vaccine. Science 373, 397-399 (2021).
McGhee JR. 2011. A mucosal gateway for vaccines. Nat Biotechnol. 29:136-8.
Mao, T. et al. Unadjuvanted intranasal spike vaccine elicits protective mucosal immunity against sarbecoviruses. Science 378(872), pp. 1-14, eabo2523 (2022).
Meinhardt, J. et al. Olfactory transmucosal SARS-CoV-2 invasion as a port of central nervous system entry in individuals with COVID-19. Nat. Neurosci. 24, 168-175 (2021).
Moghaddam A, Olszewska W, Wang B, Tregoning JS, Helson R, Sattentau QJ, Openshaw PJ. 2006. A potential molecular mechanism for hypersensitivity caused by formalin-inactivated vaccines. Nat Med. 12:905-7.
Morabito KM, Ruckwardt TR, Redwood AJ, Moin SM, Price DA, Graham BS. 2017. Intranasal administration of RSV antigen-expressing MCMV elicits robust tissue-resident effector and effector memory CD8+ T cells in the lung. Mucosal Immunol. 10:545-554.
Neutra MR, Kozlowski PA. 2006. Mucosal vaccines: the promise and the challenge. Nat Rev Immunol. 6:148-58.

(56) References Cited

OTHER PUBLICATIONS

Ngwuta JO, et al. 2015. Prefusion F-specific antibodies determine the magnitude of RSV neutralizing activity in human sera. Sci Transl Med. 7:309ra162.

Ochsner, S. P. et al. FcRn-Targeted Mucosal Vaccination against Influenza Virus Infection. *J Immunol.* 207(5), 1310-1321 (2021).

Oh, J. E. et al. Intranasal priming induces local lung-resident B cell populations that secrete protective mucosal antiviral IgA. *Sci. Immunol.* 6, pp. 1-11, eabj5129 (2021).

Oladunni, F. S. et al. Lethality of SARS-CoV-2 infection in K18 human angiotensin-converting enzyme 2 transgenic mice. *Nat. Commun.* 11, 6122 (2020).

Openshaw PJ, Tregoning JS. 2005. Immune responses and disease enhancement during respiratory syncytial virus infection. Clin Microbiol Rev. 18:541-55.

Oshansky CM, Zhang W, Moore E, Tripp RA. 2009. The host response and molecular pathogenesis associated with respiratory syncytial virus infection. Future Microbiol. 4:279-97.

Pallesen, J. et al. Immunogenicity and structures of a rationally designed prefusion MERS-CoV spike antigen. *Proc. Natl. Acad. Sci. U S A.* 114, E7348-E7357 (2017).

Palomo C, et al. 2016. Influence of Respiratory Syncytial Virus F Glycoprotein Conformation on Induction of Protective Immune Responses. J Virol. 90:5485-98.

Passmore C, et al. Intranasal immunization with W 80 5EC adjuvanted recombinant RSV rF-ptn enhances clearance of respiratory syncytial virus in a mouse model. Hum Vaccin Immunother. 2014;10(3):615-22.

Pavot V, Rochereau N, Genin C, Verrier B, Paul S. 2012. New insights in mucosal vaccine development. Vaccine. 30:142-54.

Pierantoni A, et al. Mucosal delivery of a vectored RSV vaccine is safe and elicits protective immunity in rodents and nonhuman primates. Mol Ther Methods Clin Dev. May 20, 2015;2:15018.

Planas, D. et al. Considerable escape of SARS-CoV-2 Omicron to antibody neutralization. *Nature* 602, 671-675 (2022).

Rath et al., Regulation of immune responses by the neonatal Fc receptor and its therapeutic implications. Front Immunol. 2015, vol. 5:664.

Roukens, A. H. E. et al. Prolonged activation of nasal immune cell populations and development of tissue-resident SARS-CoV-2-specific CD8+ T cell responses following COVID-19. *Nat. Immunol.* 23, 23-32 (2022).

Ruan et al., Suppressive effect of locally produced interleukin-10 on respiratory syncytial virus infection. Immunology. 2001, vol. 104(3), p. 355-60.

Russell, M. W. & Mestecky, J. Mucosal immunity: The missing link in comprehending SARS-CoV-2 infection and transmission. *Front Immunol.* 13: 957107 (2022).

Sakurai, A. et al. Natural History of Asymptomatic SARS-CoV-2 Infection. *N. Engl. J. Med.* 383, 885-886 (2020).

Sia, S. F. et al. Pathogenesis and transmission of SARS-CoV-2 in golden hamsters. *Nature* 583, 834-838 (2020).

Spiekermann, G. M. et al. Receptor-mediated immunoglobulin G transport across mucosal barriers in adult life: functional expression of FcRn in the mammalian lung. J. Exp. Med. 196: 303-310 (2002).

Sterlin, D. et al. IgA dominates the early neutralizing antibody response to SARS-CoV-2. *Sci. Transl. Med.* 13, pp. 1-10, eabd2223 (2021).

Sui, Y. et al. Protection against SARS-CoV-2 infection by a mucosal vaccine in rhesus macaques. JCI Insight. Apr. 28, 2021;6(10): e148494.

Szabo, P. A., Miron, M., & Farber, D. L. Location, location, location: Tissue resident memory T cells in mice and humans. Sci. Immunol. 4(34), eaas9673 (2019).

Tang, J. et al. Respiratory mucosal immunity against SARS-CoV-2 after mRNA vaccination. *Sci. Immunol.* 7(76), eadd4853 (2022).

Van Doremalen, N. et al. ChAdOx1 nCoV-19 vaccine prevents SARS-CoV-2 pneumonia in rhesus macaques. *Nature* 586, 578-592 (2020). Erratum in: *Nature* 590, E24 (2021).

Vissers M, Ahout IML, de Jonge MI, Ferwerda G. 2016. Mucosal IgG levels correlate better with respiratory syncytial virus load and inflammation than plasma IgG levels. Clin Vaccine Immunol 23:243-245.

V'kovski, P., Kratzel, A., Steiner, S., Stalder, H., & Thiel, V. Coronavirus biology and replication: implications for SARS-CoV-2. *Nat. Rev. Microbiol.* 19, 155-170 (2021).

Walls et al. "Structure, function and antigenicity of the SARS-CoV-2 spike glycoprotein" bioRxiv, Feb. 20, 2020; Cell 180, 281-292, Apr. 16, 2020.

Ward, E.S., Zhou, J., Ghetie, V., & Ober, R. J. Evidence to support the cellular mechanism involved in serum IgG homeostasis in humans. *Int. Immunol.* 15, 187-195 (2003).

Yang K, Varga SM. 2014. Mucosal vaccines against respiratory syncytial virus. Curr Opin Virol. 6:78-84.

Yen, H. L. et al. Transmission of SARS-CoV-2 delta variant (AY.127) from pet hamsters to humans, leading to onward human-to-human transmission: a case study. *Lancet* 399, 1070-1078 (2022).

Yoshida, M. et al. Human neonatal Fc receptor mediates transport of IgG into luminal secretions for delivery of antigens to mucosal dendritic cells. *Immunity* 20, 769-783 (2004).

Zeng, et al. SARS-CoV-2 spreads through cell-to-cell transmission. *Proc. Natl. Acad. Sci. U S A.* 119(1), e2111400119 (2022).

Zhou, D. et al. Robust SARS-CoV-2 infection in nasal turbinates after treatment with systemic neutralizing antibodies. *Cell Host Microbe.* 29(4), 551-563.e5 (2021).

International Search Report and Written Opinion were mailed on Feb. 22, 2019 by the International Searching Authority for International Application No. PCT/US2018/055896, filed on Oct. 15, 2018 and published as WO 2019/046864 on Apr. 4, 2019 (Applicant—Xiaoping Zhu) (14 Pages).

Written Opinion and International Search Report issued Jul. 1, 2021 by the International Searching Authority for Application No. PCT/US2021/020099 filed on Feb. 26, 2021 (Applicant: University of Maryland) (11 pages).

An, Xingyue et al., "Single-does intranasal vaccination elicits systemic and mucosal immunity against SARS-CoV-2," BioRxiv, XP093120206, DOI: 10.1101/2020.07.23.212357 (2020).

Li, Jie et al., "Immunogenicity and Protection Efficacy of Monomeric and Trimeric Recombinant SARS Coronavirus Spike Protein Subunit Vaccine Candidates," Viral Immunology, 26(2): 126-132 (2013).

Li, Weizhong et al., An FcRn-targeted mucosal vaccine against SARS-CoV-2 infection and transmission, bioRxiv, XP093119729, DOI: 10.1101/2022.11.23.517678 (2022).

Shan et al., "In vivo pharmacokinetic enhancement of momomeric Fc and monovalent bispecific designs through structural guidance," Communications Biology (2021) 4:1048; and https://doi.org/10.1038/s42003-021-02565-5, Nature.com/commsbio (Year: 2021), (11 Pages).

Wrapp et al., "Cryo-EM structure of 2019-nCoV spike in the prefusion conformation," Science 367:1260-1263 (2020).

Supplementary European Search Report mailed Jan. 29, 2024 for EP 21760268.9, filed Sep. 23, 2022.

SEQUENCE LISTING

```
Sequence total quantity: 17
SEQ ID NO: 1            moltype = AA  length = 833
FEATURE                 Location/Qualifiers
REGION                  1..833
                        note = synthetic construct; a monomeric Fc fragment of an
                        immunoglobulinrecognized by a FcRn; an influenza HA
                        protein; and atrimerization domain
source                  1..833
                        mol_type = protein
                        organism = synthetic construct
SEQUENCE: 1
MPMGSLQPLA TLYLLGMLVA SCLGEPRGPT IKPSPPSKSP APNLLGGPSV FIFPPKIKDV   60
LMISLSPIVT CVVVDVSEDD PDVQISWFVN NVEVHTAQTQ THREDYNSTL RVVSALPIQH  120
QDWMSGKAFA CAVNNKDLPA PIERTISKPK GSVRAPQVYV LPPPEEEMTK KQVTLTCMVT  180
DFMPEDIYVE WTNNGKTELN YKNTEPVLDS DGSYFMYSKL RVEKKNWVER NSYSCSVVHE  240
GLHNHHTTKS FSRTPGKGSG GGGSGGGGSG SDTICIGYHA NNSTDTVDTV LEKNVTVTHS  300
VNLLEDSHNG KLCRLKGIAP LQLGKCNIAG WLLGNPECDP LLPVRSWSYI VETPNSENGI  360
CYPGDFIDYE ELREQLSSVS SFERFEIFPK ESSWPNHNTN GVTAACSHEG KSSFYRNLLW  420
LTEKEGSYPK LKNSYVNKKG KEVLVLWGIH HPPNSKEQQN IYQNENAYVS VVTSNYNRRF  480
TPEIAERPKV RDQAGRMNYY WTLLKPGDTI IFEANGNLIA PMYAFALSRG FGSGIITSNA  540
SMHECNTKCQ TPLGAINSSL PYQNIHPVTI GECPKYVRSA KLRMVTGLRN NPQRETRGLF  600
GAIAGFIEGG WTGMIDGWYG YHHQNEQGSG YAADQKSTQN AINGITNKVN TVIEKMNIQF  660
TAVGKEFNKL EKRMENLNKK VDDGFLDIWT YNAELLVLLE NERTLDFHDS NVKNLYEKVK  720
SQLKNNAKEI GNGCFEFYHK CDNECMESVR NGTYDYPKYS EESKLNREKV DGVKLESMGI  780
YQGSGSGSRS LVPRGSPGSG YIPEAPRDGQ AYVRKDGEWV LLSTFLGHHH HHH         833

SEQ ID NO: 2            moltype = AA  length = 233
FEATURE                 Location/Qualifiers
```

| | | |
|---|---|---|
| REGION | 1..233 | |
| | note = synthetic construct; a monomeric Fc fragment of a mouse IgG2a | |
| source | 1..233 | |
| | mol_type = protein | |
| | organism = synthetic construct | |

SEQUENCE: 2
```
EPRGPTIKPS PPSKSPAPNL LGGPSVFIFP PKIKDVLMIS LSPIVTCVVV DVSEDDPDVQ   60
ISWFVNNVEV HTAQTQTHRE DYNSTLRVVS ALPIQHQDWM SGKAFACAVN NKDLPAPIER  120
TISKPKGSVR APQVYVLPPP EEEMTKKQVT LTCMVTDFMP EDIYVEWTNN GKTELNYKNT  180
EPVLDSDGSY FMYSKLRVEK KNWVERNSYS CSVVHEGLHN HHTTKSFSRT PGK         233
```

| | | |
|---|---|---|
| SEQ ID NO: 3 | moltype = DNA  length = 699 | |
| FEATURE | Location/Qualifiers | |
| misc_feature | 1..699 | |
| | note = synthetic construct; a monomeric Fc fragment of a mouse IgG2a | |
| source | 1..699 | |
| | mol_type = other DNA | |
| | organism = synthetic construct | |

SEQUENCE: 3
```
gagcccagag ggcccacaat caagccctct cctccatcca aatccccagc acctaacctc   60
ttgggtggac catccgtctt catcttccct ccaaagatca aggatgtact catgatctcc  120
ctgagcccca tagtcacatg tgtggtggtg gatgtgagcg aggatgaccc agatgtccag  180
atcagctggt ttgtgaacaa cgtggaagta cacacagctc agacacaaac ccatagagag  240
gattacaaca gtactctccg ggtggtcagt gccctcccca tccagcacca ggactggatg  300
agtggcaagg cgttcgcatg cgcggtcaac aacaaagacc tcccagcgcc catcgagaga  360
accatctcaa aacccaaagg gtcagtaaga gctccacagg tatatgtctt gcctccacca  420
gaagaagaga tgactaagaa acaggtcact ctgacctgca tggtcacaga cttcatgcct  480
gaagacattt acgtggagtg gaccaacaac gggaaaacag agctaaacta caagaacact  540
gaaccagtcc tggactctga tggttcttac ttcatgtaca gcaagctgag agtggaaaag  600
aagaactggg tggaaagaaa tagctactcc tgttcagtgg tccacgaggg tctgcacaat  660
caccacacga ctaagagctt ctcccggact ccgggtaaa                         699
```

| | | |
|---|---|---|
| SEQ ID NO: 4 | moltype = AA  length = 233 | |
| FEATURE | Location/Qualifiers | |
| REGION | 1..233 | |
| | note = synthetic construct; a monomeric Fc fragment of a mouse IgG2awith FcRn-binding abolished | |
| source | 1..233 | |
| | mol_type = protein | |
| | organism = synthetic construct | |

SEQUENCE: 4
```
EPRGPTIKPS PPSKSPAPNL LGGPSVFIFP PKIKDVLMIS LSPIVTCVVV DVSEDDPDVQ   60
ISWFVNNVEV HTAQTQTHRE DYNSTLRVVS ALPIQADDWM SGKAFACAVN NKDLPAPIER  120
TISKPKGSVR APQVYVLPPP EEEMTKKQVT LTCMVTDFMP EDIYVEWTNN GKTELNYKNT  180
EPVLDSDGSY FMYSKLRVEK KNWVERNSYS CSVVHEGLAQ HHTTKSFSRT PGK         233
```

| | | |
|---|---|---|
| SEQ ID NO: 5 | moltype = DNA  length = 699 | |
| FEATURE | Location/Qualifiers | |
| misc_feature | 1..699 | |
| | note = synthetic construct; a monomeric Fc fragment of a mouse IgG2awith FcRn-binding abolished | |
| source | 1..699 | |
| | mol_type = other DNA | |
| | organism = synthetic construct | |

SEQUENCE: 5
```
gagcccagag ggcccacaat caagccctct cctccatcca aatccccagc acctaacctc   60
ttgggtggac catccgtctt catcttccct ccaaagatca aggatgtact catgatctcc  120
ctgagcccca tagtcacatg tgtggtggtg gatgtgagcg aggatgaccc agatgtccag  180
atcagctggt ttgtgaacaa cgtggaagta cacacagctc agacacaaac ccatagagag  240
gattacaaca gtactctccg ggtggtcagt gccctcccca tccaggccga cgactggatg  300
agtggcaagg cgttcgcatg cgcggtcaac aacaaagacc tcccagcgcc catcgagaga  360
accatctcaa aacccaaagg gtcagtaaga gctccacagg tatatgtctt gcctccacca  420
gaagaagaga tgactaagaa acaggtcact ctgacctgca tggtcacaga cttcatgcct  480
gaagacattt acgtggagtg gaccaacaac gggaaaacag agctaaacta caagaacact  540
gaaccagtcc tggactctga tggttcttac ttcatgtaca gcaagctgag agtggaaaag  600
aagaactggg tggaaagaaa tagctactcc tgttcagtgg tccacgaggg tctggcccaa  660
caccacacga ctaagagctt ctcccggact ccgggtaaa                         699
```

| | | |
|---|---|---|
| SEQ ID NO: 6 | moltype = AA  length = 511 | |
| FEATURE | Location/Qualifiers | |
| source | 1..511 | |
| | mol_type = protein | |
| | organism = Influenza A virus | |

SEQUENCE: 6
```
DTICIGYHAN NSTDTVDTVL EKNVTVTHSV NLLEDSHNGK LCRLKGIAPL QLGKCNIAGW   60
LLGNPECDPL LPVRSWSYIV ETPNSENGIC YPGDFIDYEE LREQLSSVSS FERFEIFPKE  120
SSWPNHNTNG VTAACSHEGK SSFYRNLLWL TEKEGSYPKL KNSYVNKKGK EVLVLWGIHH  180
```

```
PPNSKEQQNI YQNENAYVSV VTSNYNRRFT PEIAERPKVR DQAGRMNYYW TLLKPGDTII   240
FEANGNLIAP MYAFALSRGF GSGIITSNAS MHECNTKCQT PLGAINSSLP YQNIHPVTIG   300
ECPKYVRSAK LRMVTGLRNN PQRETRGLFG AIAGFIEGGW TGMIDGWYGY HHQNEQGSGY   360
AADQKSTQNA INGITNKVNT VIEKMNIQFT AVGKEFNKLE KRMENLNKKV DDGFLDIWTY   420
NAELLVLLEN ERTLDFHDSN VKNLYEKVKS QLKNNAKEIG NGCFEFYHKC DNECMESVRN   480
GTYDYPKYSE ESKLNREKVD GVKLESMGIY Q                                 511

SEQ ID NO: 7            moltype = AA  length = 29
FEATURE                 Location/Qualifiers
REGION                  1..29
                        note = synthetic construct; foldon
source                  1..29
                        mol_type = protein
                        organism = synthetic construct
SEQUENCE: 7
GSGYIPEAPR DGQAYVRKDG EWVLLSTFL                                    29

SEQ ID NO: 8            moltype = AA  length = 87
FEATURE                 Location/Qualifiers
REGION                  1..87
                        note = synthetic construct; foldon
source                  1..87
                        mol_type = protein
                        organism = synthetic construct
SEQUENCE: 8
GGCAGCGGCT ACATCCCCGA GGCCCCCAGA GACGGCCAGG CCTACGTGAG AAAGGACGGC   60
GAGTGGGTGC TGCTGAGCAC CTTCCTG                                      87

SEQ ID NO: 9            moltype = AA  length = 32
FEATURE                 Location/Qualifiers
REGION                  1..32
                        note = synthetic construct; transcription factor GCN4pII
                          trimerizationmotif
source                  1..32
                        mol_type = protein
                        organism = synthetic construct
SEQUENCE: 9
MKQIEDKIEE ILSKIYHIEN EIARIKKLIG EV                                 32

SEQ ID NO: 10           moltype = AA  length = 6
FEATURE                 Location/Qualifiers
REGION                  1..6
                        note = synthetic construct; linker
source                  1..6
                        mol_type = protein
                        organism = synthetic construct
SEQUENCE: 10
GSGSGS                                                              6

SEQ ID NO: 11           moltype = AA  length = 14
FEATURE                 Location/Qualifiers
REGION                  1..14
                        note = synthetic construct; linker
source                  1..14
                        mol_type = protein
                        organism = synthetic construct
SEQUENCE: 11
GSGGGGSGGG GSGS                                                     14

SEQ ID NO: 12           moltype = DNA  length = 45
FEATURE                 Location/Qualifiers
misc_feature            1..45
                        note = synthetic construct; primer
source                  1..45
                        mol_type = other DNA
                        organism = synthetic construct
SEQUENCE: 12
gccgaagctt gccaccatga aggcaaacct actggtcctg ttaag                   45

SEQ ID NO: 13           moltype = DNA  length = 64
FEATURE                 Location/Qualifiers
misc_feature            1..64
                        note = synthetic construct; primer
source                  1..64
                        mol_type = other DNA
                        organism = synthetic construct
SEQUENCE: 13
agatcccgag ccacctcctc cggacccacc cccgcctgat ccctgataga tccccattga   60
ttcc                                                                64
```

```
SEQ ID NO: 14          moltype = DNA  length = 67
FEATURE                Location/Qualifiers
misc_feature           1..67
                       note = synthetic construct; primer
source                 1..67
                       mol_type = other DNA
                       organism = synthetic construct
SEQUENCE: 14
ggatcaggcg ggggtgggtc cggaggaggt ggctcgggat ctgagcccag agggcccaca    60
atcaagc                                                              67

SEQ ID NO: 15          moltype = DNA  length = 38
FEATURE                Location/Qualifiers
misc_feature           1..38
                       note = synthetic construct; primer
source                 1..38
                       mol_type = other DNA
                       organism = synthetic construct
SEQUENCE: 15
gccgtctaga ttatttaccc ggagtccggg agaagctc                            38

SEQ ID NO: 16          moltype = DNA  length = 68
FEATURE                Location/Qualifiers
misc_feature           1..68
                       note = synthetic construct; primer
source                 1..68
                       mol_type = other DNA
                       organism = synthetic construct
SEQUENCE: 16
ggatcaggcg ggggtgggtc cggaggaggt ggctcgggat ctgacacaat atgtataggc    60
taccatgc                                                             68

SEQ ID NO: 17          moltype = DNA  length = 60
FEATURE                Location/Qualifiers
misc_feature           1..60
                       note = synthetic construct; primer
source                 1..60
                       mol_type = other DNA
                       organism = synthetic construct
SEQUENCE: 17
cctctgggca ccaggcttct tgatcctgag cctgatccct gatagatccc cattgattcc    60
```

FCRN-TARGETED MUCOSAL VACCINATION AGAINST INFLUENZA INFECTIONS

CROSS-REFERENCE TO RELATED APPLICATIONS

This application is a continuation of U.S. application Ser. No. 16/373,272, filed Apr. 2, 2019, which claims the benefit of U.S. Provisional Patent Application No. 62/651,522, filed Apr. 2, 2018, each of which is incorporated by reference herein in its entirety.

REFERENCE TO SEQUENCE LISTING

The Sequence Listing submitted Feb. 1, 2023 as a text file named "36429_0024U3.xml," created on Jan. 31, 2023, and having a size of 25,727 bytes is hereby incorporated by reference pursuant to 37 C.F.R. § 1.52(e)(5).

STATEMENT REGARDING FEDERALLY SPONSORED RESEARCH

This invention was made with government support under AI067965 and AI146063 awarded by National Institutes of Health. The government has certain rights in the invention.

BACKGROUND

Respiratory infections are particularly significant causes of illnesses and deaths. Vaccination decreases the spread, severity, and complications of respiratory diseases by inducing mucosal immunity in the airway. FcRn mediates IgG transfer across the respiratory epithelium. Our strategy targets FcRn to deliver vaccines to the entire airway surface. An intranasal vaccine based on a model influenza virus hemagglutinin antigen has been designed. This FcRn-targeted mucosal vaccine delivery pathway induces remarkable and long-lasting T-cell responses and IgA and IgG Abs in the airway and blood. The achieved immunity or memory immune responses are effective against lethal virus infections. Thus, FcRn-targeted respiratory immunization offers an effective platform for generating protective immune responses against influenza virus infection and other common respiratory pathogens.

BRIEF SUMMARY

Disclosed are peptides comprising a monomeric Fc fragment of an immunoglobulin recognized by a neonatal receptor (FcRn); an influenza HA protein; and a trimerization domain.

Disclosed are compositions comprising one or more of the peptides described herein.

Disclosed are nucleic acid sequences capable of encoding any one of the peptides described herein.

Disclosed are methods for eliciting a protective immune response against influenza comprising administering to a subject an effective amount of a composition comprising a monomeric Fc fragment of an immunoglobulin recognized by a FcRn; an influenza HA protein; and a trimerization domain, wherein the administering is to a mucosal epithelium.

Disclosed are methods of treating a subject exposed to influenza or at risk of being exposed to influenza comprising administering to the subject an effective amount of a composition comprising a monomeric Fc fragment of an immunoglobulin recognized by a FcRn; an influenza HA protein; and a trimerization domain, wherein the administering is to a mucosal epithelium.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIGS. 11A and 111B. The percentage of IFN-γ and TNF-α producing T cells in the lung 7 days after the boost. The lung lymphocytes from the immunized mice were stimulated for 10 hr with purified HA or medium control. Lymphocytes were gated by forward and side scatters and T cells labeled with anti-CD3 and identified by their respective surface markers CD4 and CD8 and intracellular IFN-γ or TNF-α staining. Numbers represent the percentage of IFN-γ+CD4+ (A) or TNF-α+CD4+(B). Isotype controls included FITC-mouse-IgG1 with baseline response. Flow cytometry plots are representative of two independent experiments with 4 immunized mice pooled in each group. Numbers in the quadrants are the percentage of CD4+T lymphocytes.

Lane 7, representing HA-Fc/wt protein, was used as a positive control. wt: wild-type; mut: mutant proteins.

Figure 18:
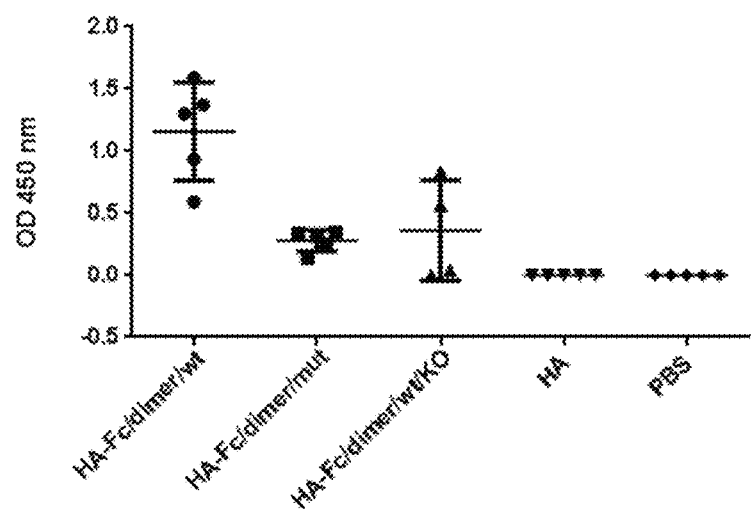

FIG. 18. Measurement of HA-specific IgG antibody responses. The 5 µg HA-Fc/wt, HA-Fc/mut, HA, or PBS in combination with 10 µg CpG were i.n. administered into wild-type (WT) or FcRn knockout (KO) mice for prime and boost immunizations at a 14-day interval. Total IgG antibodies were determined by ELISA in the sera of immunized mice (n=4-5) 14 days after a boost. The titers were shown by endpoint titer. Asterisk (***) denotes p<0.001.

Figure 19:
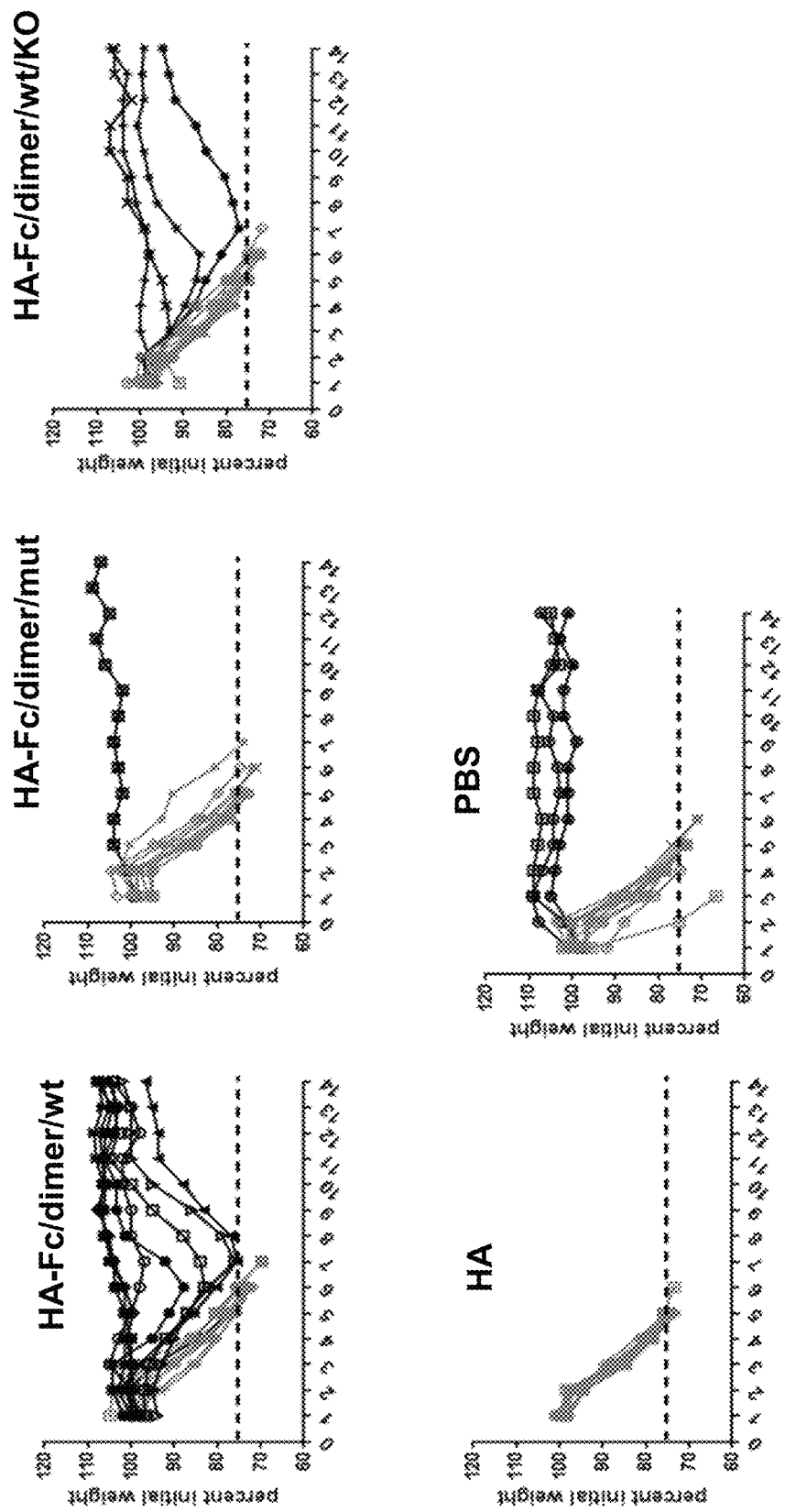

FIG. 19. The individual weight loss of the immunized mice in each group after influenza PR8 challenge. 14 days after the boost, mice were i.n. infected with 5 MLD50 of the PR8 virus and weighed daily for 14 days. Mice were euthanized when the body-weight loss reached a 25% endpoint. The weight loss of individual mouse in each group is shown. Respective colors represent mouse that has lost minimal weight or recovered.

Figure 20:
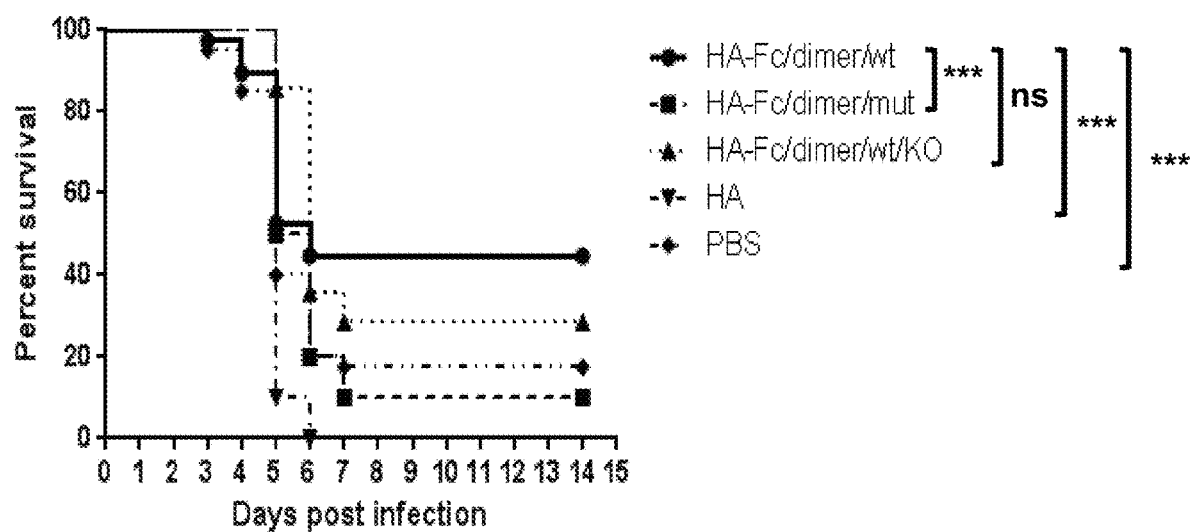

FIG. 20. Mean survival of mice following influenza challenge. Two weeks after the boost, groups of 10-40 mice were i.n. challenged with PR8 virus (5 MLD50) and weighed daily for fourteen days. Mice were deceased or humanely euthanized if the initial body weight was lost more than 25%. The percentage of mice from protection after the challenge was shown by a Kaplan-Meier survival curve. The data is representative of at least 3-4 similar experiments. Statistical differences were determined using multiple Mantel-Cox tests.

DETAILED DESCRIPTION

The disclosed method and compositions may be understood more readily by reference to the following detailed description of particular embodiments and the Example included therein and to the Figures and their previous and following description.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a peptide is disclosed and discussed and a number of modifications that can be made to a number of molecules including the amino acids are discussed, each and every combination and permutation of the peptide and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

A. Definitions

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a peptide" includes a plurality of such peptides, reference to "the peptide" is a reference to one or more peptide and equivalents thereof known to those skilled in the art, and so forth.

The word "or" as used herein means any one member of a particular list and also includes any combination of members of that list.

As used herein, the term "therapeutically effective amount" means an amount of a therapeutic, prophylactic, and/or diagnostic agent that is sufficient, when administered to a subject suffering from or susceptible to a disease, disorder, and/or condition, to treat, alleviate, ameliorate, relieve, alleviate symptoms of, prevent, delay onset of, inhibit progression of, reduce severity of, and/or reduce incidence of the disease, disorder, and/or condition.

As used herein, the term "treating" refers to partially or completely alleviating, ameliorating, relieving, delaying onset of, inhibiting progression of, reducing severity of, and/or reducing incidence of one or more symptoms or features of a particular disease, disorder, and/or condition. For example, "treating" influenza may refer to inhibiting survival, growth, and/or spread of the virus. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

As used herein, the term "amino acid sequence" refers to a list of abbreviations, letters, characters or words representing amino acid residues. The amino acid abbreviations used herein are conventional one letter codes for the amino acids and are expressed as follows: A, alanine; C, cysteine; D aspartic acid; E, glutamic acid; F, phenylalanine; G, glycine; H histidine; I isoleucine; K, lysine; L, leucine; M, methionine; N, asparagine; P, proline; Q, glutamine; R, arginine; S, serine; T, threonine; V, valine; W, tryptophan; and Y, tyrosine.

"Peptide" as used herein refers to any peptide, oligopeptide, polypeptide, gene product, expression product, or protein. A peptide is comprised of consecutive amino acids. The term "peptide" encompasses naturally occurring or synthetic molecules.

As used herein, "sample" is meant to mean an animal; a tissue or organ from an animal; a cell (either within a subject, taken directly from a subject, or a cell maintained in culture or from a cultured cell line); a cell lysate (or lysate fraction) or cell extract; or a solution containing one or more molecules derived from a cell or cellular material (e.g. a polypeptide or nucleic acid), which is assayed as described herein. A sample may also be any body fluid or excretion (for example, but not limited to, blood, urine, stool, saliva, tears, bile) that contains cells or cell components.

As used herein, "subject" refers to the target of administration, e.g. an animal. Thus the subject of the disclosed methods can be a vertebrate, such as a mammal. For example, the subject can be a human. The term does not denote a particular age or sex. Subject can be used interchangeably with "individual" or "patient".

Ranges may be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

B. Peptides

Disclosed are peptides comprising a monomeric Fc fragment of an immunoglobulin recognized by a FcRn; an influenza HA protein; and a trimerization domain. In some instances, disclosed are peptides comprising a monomeric Fc fragment of an immunoglobulin recognized by a FcRn; an influenza HA protein; and a trimerization domain wherein the peptide comprises the sequence:

(SEQ ID NO: 1)
mpmgslqplatlyllgmlvasclgEPRGPTIKPSPPSKSPAPNLLGGPS

VFIFPPKIKDVLMISLSPIVTCVVVDVSEDDPDVQISWFVNNVEVHTAQ

TQTHREDYNSTLRVVSALPIQHQDWMSGKAFACAVNNKDLPAPIERTIS

KPKGSVRAPQVYVLPPPEEEMTKKQVTLTCMVTDFMPEDIYVEWTNNGK

TELNYKNTEPVLDSDGSYFMYSKLRVEKKNWVERNSYSCSVVHEGLHNH
HTTKSFSRTPGKGSGGGGSGGGGSGSDTICIGYHANNSTDTVDTVLEKN
VTVTHSVNLLEDSHNGKLCRLKGIAPLQLGKCNIAGWLLGNPECDPLLP
VRSWSYIVETPNSENGICYPGDFIDYEELREQLSSVSSFERFEIFPKES
SWPNHNTNGVTAACSHEGKSSFYRNLLWLTEKEGSYPKLKNSYVNKKGK
EVLVLWGIHHPPNSKEQQNIYQNENAYVSVVTSNYNRRFTPEIAERPKV
RDQAGRMNYYWTLLKPGDTIIFEANGNLIAPMYAFALSRGFGSGIITSN
ASMHECNTKCQTPLGAINSSLPYQNIHPVTIGECPKYVRSAKLRMVTGL
RNNPQRETRGLFGAIAGFIEGGWTGMIDGWYGYHHQNEQGSGYAADQKS
TQNAINGITNKVNTVIEKMNIQFTAVGKEFNKLEKRMENLNKKVDDGFL
DIWTYNAELLVLLENERTLDFHDSNVKNLYEKVKSQLKNNAKEIGNGCF
EFYHKCDNECMESVRNGTYDYPKYSEESKLNREKVDGVKLESMGIYQgs
gsgsRSLVPRGSPGSGYIPEAPRDGQAYVRKDGEWVLLSTFLGHHHHHH.

The lower case letters represent a CD5 signal peptide. The bold, underlined, capitalized letters represent a mouse Fc IgG2a single chain. The double underlined codons in the Fc IgG2a show the three cysteine sites that are mutated to serine in order to generate a monomeric Fc IgG2a. The two grey highlighted regions of the monomeric Fc IgG2a are regions responsible for FcRn binding. The first sequence, HQ, can be mutated to AD. The second sequence, HN, can be mutated to AQ in order to abolish FcRn binding. The bold, capitalized letters represent a influenza HA protein. The underlined, lower case letters represent a 6 GS linker. The italicized, capital letters represent a 14 GS linker. The double underlined, capitalized letters represent a thrombin recognition site. The underlined, capitalized letters represent foldon from T4 fibritin. The underlined with the curved lines, capitalized letters represent 6×His tag at the C-terminus.

In some instances, disclosed are peptides comprising a monomeric Fc fragment of an immunoglobulin recognized by a FcRn; an influenza HA protein; and a trimerization domain wherein the peptide comprises a sequence that is 90% identical to the sequence of SEQ ID NO: 1, wherein the CD5 signal peptide, an influenza HA protein, the GS linker, the 14 GS linker, the thrombin recognition site, the foldon from T4 fibritin, the mouse Fc IgG2a single chain, or the regions of the monomeric Fc IgG2a regions responsible for FcRn binding are the same or 50%, 55%, 65%, 70%, 75%, 80%, 90%, 95%, 96%, 97%, 98%, or 99% identical to the sequence of SEQ ID NO: 1.

1. Monomeric Fc Fragment of an Immunoglobulin Recognized by FcRn

A monomeric Fc fragment of an immunoglobulin as disclosed herein can be recognized by a FcRn. In some instances the monomeric Fc fragment of an immunoglobulin comprises a mutation in the Fc region of an immunoglobulin recognized by FcRn sequence that results in the prevention of dimer formation. In some aspects, the monomeric Fc fragment of an immunoglobulin recognized by a FcRn comprises at least one mutation in a cysteine residue responsible for dimer formation. For example, mutations can be at one or more of positions 224, 227, and 229. In some aspects, the cysteines at one or more of positions 224, 227, and 229 are substituted with a serine.

In some instances, the amino acid sequence of a monomeric Fc fragment of a mouse IgG2a can be EPRGP-TIKPSPPSKSPAPNLLGGPSVFIFPPKIKDVLMISLSPIV-TCVVVDVSEDDPDVQIS WFVNNVEVHTAQTQTHREDYNSTLRVVSAL-PIQHQDWMSGKAFACAVNNKDLPAPIE RTISKPKGSVRAPQVYVLPP-PEEEMTKKQVTLTCMVTDFMPEDIYVEWTNNGK-TELNY KNTEPVLDSDGSYFMYSKLRVEK-KNWVERNSYSCSVVHEGLHNHHTTKSFSRTPGK (SEQ ID NO:2) or a sequence 50%, 55%, 65%, 70%, 75%, 80%, 90%, 95%, 96%, 97%, 98%, or 99% identical to the sequence of SEQ ID NO:2. The bold underlined amino acids represent a mutation from cysteine to serine to generate a single chain Fc.

In some instances, the nucleic acid sequence of a monomeric Fc fragment of a mouse IgG2a can be GAGCCCAGAGGGCCCACAATCAAGCCCTCTCCTC-CATCCAAATCCCCAGCACCTAA CCTCTTGGGTGGACCATCCGTCTTCATCTTCCCTC-CAAAGATCAAGGATGTACTCAT GATCTCCCT-GAGCCCCATAGTCACATGTGTGGTGGTGGATGT-GAGCGAGGATGACC CAGATGTCCAGATCAGCTGGTTTGTGAACAACGTG-GAAGTACACACAGCTCAGACA CAAACCCAT-AGAGAGGATTA-CAACAGTACTCTCCGGGTGGTCAGTGCCCTCCCCAT CCAGCACCAGGACTGGAT-GAGTGGCAAGGCGTTCGCATGCGCGGT-CAACAACAAA GACCTCCCAGCGCC-CATCGAGAGAACCATCTCAAAACCCAAAGGGTCA-GTAAGAGC TCCACAGGTATATGTCTTGCCTC-CACCAGAAGAAGAGATGACTAAGAAACAGGTCA CTCTGACCTGCATGGTCACAGACTTCATGCCTGAA-GACATTTACGTGGAGTGGACCA ACAACGG-GAAAACAGAGCTAAACTACAAGAACACT-GAACCAGTCCTGGACTCTGAT GGTTCTTACTTCATGTACAGCAAGCTGAGAGTG-GAAAAGAAGAACTGGGTGGAAAG AAATAGC-TACTCCTGTTCAGTGGTC-CACGAGGGTCTGCACAATCACCACACGACTA AGAGCTTCTCCCGGACTCCGGGTAAA (SEQ ID NO:3) or a sequence 50%, 55%, 65%, 70%, 75%, 80%, 90%, 95%, 96%, 97%, 98%, or 99% identical to the sequence of SEQ ID NO:3. The bold underlined nucleic acids represent a mutation that encodes serine instead of cysteine to generate a single chain Fc.

In some instances, corresponding mutations can be made in other IgG Fc fragments in order to mutate the cysteine residues responsible for dimer formation.

In some instances, other mutations can be made throughout the Fc fragment of an immunoglobulin recognized by a FcRn so long as the FcRn binding region is not affected. In some instances, other mutations can be made throughout the Fc fragment of an immunoglobulin wherein the FcRn binding region is disrupted. For example, in some instances, the amino acid sequence of a monomeric Fc fragment of a mouse IgG2a with FcRn-binding abolished can be EPRGP-TIKPSPPSKSPAPNLLGGPSVFIFPPKIKDVLMISLSPIV-TCVVVDVSEDDPDVQIS WFVNNVEVHTAQTQ-THREDYNSTLRVVSALPIQADDWMSGKAFACAVNN-KDLPAPIE RTISKPKGSVRAPQVYVLPP-PEEEMTKKQVTLTCMVTDFMPEDIYVEWTNNGK-TELNY KNTEPVLDSDGSYFMYSKLRVEK-KNWVERNSYSCSVVHEGLAQHHTTKSFSRTPGK (SEQ ID NO:4). The bold underlined amino acids represent mutations that generate abolished FcRn-binding.

In some instances, the nucleic acid sequence of a monomeric Fc fragment of a mouse IgG2a with FcRn-binding abolished can be GAGCCCAGAGGGCCCACAAT-CAAGCCCTCTCCTCCATC-CAAATCCCCAGCACCTAA CCTCTTGGGTGGAC-CATCCGTCTTCATCTTCCCTCCAAAGATCAAGGAT-GTACTCAT GATCTCCCTGAGCCCCATAGTCA-CATGTGTGGTGGTGGATGTGAGCGAGGATGACC CAGATGTCCAGATCAGCTGGTTTGTGAACAACGTG-GAAGTACACACAGCTCAGACA CAAACCCAT-AGAGAGGATTA-CAACAGTACTCTCCGGGTGGTCAGTGCCCTCCCCAT CCAGGCCGACGACTGGAT-GAGTGGCAAGGCGTTCGCATGCGCGGT-CAACAACAAA GACCTCCCAGCGCC-CATCGAGAGAACCATCTCAAAACCCAAAGGGTCA-GTAAGAGC TCCACAGGTATATGTCTTGCCTC-CACCAGAAGAAGAGATGACTAAGAAACAGGTCA CTCTGACCTGCATGGTCACAGACTTCATGCCTGAA-GACATTTACGTGGAGTGGACCA ACAACGG-GAAAACAGAGCTAAACTACAAGAACACT-GAACCAGTCCTGGACTCTGAT GGTTCTTACTTCATGTACAGCAAGCTGAGAGTG-GAAAAGAAGAACTGGGTGGAAAG AAATAGC-TACTCCTGTTCAGTGGTCCACGAGGGTCTGGCC-CAACACCACACGACTA AGAGCTTCTCCCGGACTCCGGGTAAA (SEQ ID NO:5) or a sequence 50%, 55%, 65%, 70%, 75%, 80%, 90%, 95%, 96%, 97%, 98%, or 99% identical to the sequence of SEQ ID NO:5. The bold underlined nucleic acids represent mutations that generate abolished FcRn-binding.

In some instances, the monomeric Fc fragment of an immunoglobulin recognized by a FcRn is conjugated to the amino or carboxy terminal end of an influenza protein. For example, the influenza protein can be HA or a fragment thereof. The conjugation can be direct or indirect. Indirect conjugation can be due to the presence of a linker in between the influenza protein and the monomeric Fc fragment of an immunoglobulin recognized by a FcRn.

In some instances, the monomeric Fc fragment of an immunoglobulin recognized by a FcRn is an IgG Fc fragment.

2. Influenza Protein

In some instances, an influenza protein is a wild type influenza protein from any influenza strain. In some instances, the influenza protein is a HA protein. In some instances, the influenza protein can be other influenza proteins, including HA stalk, M2, NA, and NP.

In some instances, for example, the wild type sequence of a HA protein can be (SEQ ID NO: 6)
DTICIGYHANNSTDTVDTVLEKNVTVTHSVNLLEDSHNGKLCRLKGIAPL

QLGKCNIAGWLLGNPECDPLLPVRSWSYIVETPNSENGICYPGDFIDYEE

LREQLSSVSSFERFEIFPKESSWPNHNTNGVTAACSHEGKSSFYRNLLWL

TEKEGSYPKLKNSYVNKKGKEVLVLWGIHHPPNSKEQQNIYQNENAYVSV

VTSNYNRRFTPEIAERPKVRDQAGRMNYYWTLLKPGDTIIFEANGNLIAP

MYAFALSRGFGSGIITSNASMHECNTKCQTPLGAINSSLPYQNIHPVTIG

ECPKYVRSAKLRMVTGLRNNPQRETRGLFGAIAGFIEGGWTGMIDGWYGY

HHQNEQGSGYAADQKSTQNAINGITNKVNTVIEKMNIQFTAVGKEFNKLE

KRMENLNKKVDDGFLDIWTYNAELLVLLENERTLDFHDSNVKNLYEKVKS

QLKNNAKEIGNGCFEFYHKCDNECMESVRNGTYDYPKYSEESKLNREKVD

GVKLESMGIYQ (Accession number AF389118.1).

In some instances, an influenza protein is a variant of a wild type sequence influenza HA protein. In some instances, a variant of a wild type sequence of influenza HA protein can be 50%, 55%, 65%, 70%, 75%, 80%, 90%, 95%, 96%, 97%, 98%, or 99% identical to the sequence of SEQ ID NO:6.

In some instances, the influenza HA protein can be a non-cleavable HA0 protein. In some instances, a non-cleavable HA0 protein comprises mutations at the cleavage site of wild type HA0. For a full-length HA or chimeric HA which is engineered from different influenza strains, the amino acids of HA cleavage sites can be mutated by replacing with other amino acids.

3. Trimerization Domain

The disclosed peptides have a trimerization domain. In some instances, the trimerization domain is a T4 fibritin trimerization domain. For example, the T4 fibritin trimerization domain can be foldon. In some instances, the amino acid sequence of foldon is GSGYIPEAPRDGQAYVRKDGEWVLLSTFL (SEQ ID NO:7). In some instances, the amino acid sequence of foldon is 50%, 55%, 65%, 70%, 75%, 80%, 90%, 95%, 96%, 97%, 98%, or 99% identical to SEQ ID NO:7. For example, the nucleic acid sequence of foldon can be represented by the sequence (SEQ ID NO: 8)
GGCAGCGGCTACATCCCCGAGGCCCCCAGAGACGGCCAGGCCTACGTGAG

AAAGGACGGCGAGTGGGTGCTGCTGAGCACCTTCCTG.

In some instances, the trimerization domain can be, but is not limited to the transcription factor GCN4pII trimerization motif (MKQIEDKIEEILSKIYHIENEIARIKKLIGEV; SEQ ID NO:9), or human collagen XV trimerization domain. In some instances, the trimerization domain can be an amino acid sequence that is 50%, 55%, 65%, 70%, 75%, 80%, 90%, 95%, 96%, 97%, 98%, or 99% identical to SEQ ID NO:9.

4. Linkers

Disclosed are peptides comprising a monomeric Fc fragment of an immunoglobulin recognized by FcRn; an influenza protein; and a trimerization domain, wherein the peptide further comprises one or more linkers.

In some instances, at least one of the one or more linkers is on the N-terminus end of the monomeric Fc fragment of an immunoglobulin recognized by a FcRn. In some instances, at least one of the one or more linkers is on the C-terminus end of the monomeric Fc fragment of an immunoglobulin recognized by a FcRn.

In some instances, at least one of the one or more linkers is located between the influenza HA protein and the monomeric Fc fragment of an immunoglobulin recognized by a FcRn. In some instances, at least one of the one or more linkers is located between the trimerization domain and the monomeric Fc fragment of an immunoglobulin recognized by a FcRn.

In some instances, the one or more linkers are small, nonpolar, amino acid linkers. For example, the linker can be a GS-linker. The number of glycine, serine, and glycine/serine repeats can vary in the one or more linkers. Examples of GS linkers can be GSGSGS (SEQ ID NO:10) and GSGGGGSGGGGSGS (SEQ ID NO:11).

5. Additional Elements

In some instances, the disclosed peptides can further comprise cleavage sites or tag sequences.

In some instances, a cleavage site can be present in the disclosed peptides. Cleavage sites can allow for cleavage of the monomeric Fc fragment of an immunoglobulin recognized by FcRn away from the influenza protein. In some instances, a cleavage site can be recognized by a protease or a chemical compound. In some instances, a cleavage site can be a site recognized by, but not limited to, enterokinase, pepsin, factor Xa, tobacco etch virus protease, or thrombin.

In some instances, a tag sequence can be present in the disclosed peptides. In some instances, a tag sequence can be a detection label/label sequence or a purification tag. As used herein, a detection label or label sequence is any molecule that can be associated with a nucleic acid or peptide, directly or indirectly, and which results in a measurable, detectable signal, either directly or indirectly. Many such labels for incorporation into nucleic acids or coupling to nucleic acid or antibody probes are known to those of skill in the art. Examples of detection labels can be, but are not limited to, radioactive isotopes, fluorescent molecules, phosphorescent molecules, enzymes, antibodies, and ligands.

Examples of suitable fluorescent labels include fluorescein (FITC), 5,6-carboxymethyl fluorescein, Texas red, nitrobenz-2-oxa-1,3-diazol-4-yl (NBD), coumarin, dansyl chloride, rhodamine, 4'-6-diamidino-2-phenylinodole (DAPI), and the cyanine dyes Cy3, Cy3.5, Cy5, Cy5.5 and Cy7. Preferred fluorescent labels are fluorescein (5-carboxyfluorescein-N-hydroxysuccinimide ester) and rhodamine (5,6-tetramethyl rhodamine). Preferred fluorescent labels for combinatorial multicolor coding are FITC and the cyanine dyes Cy3, Cy3.5, Cy5, Cy5.5 and Cy7. The absorption and emission maxima, respectively, for these fluors are: FITC (490 nm; 520 nm), Cy3 (554 nm; 568 nm), Cy3.5 (581 nm; 588 nm), Cy5 (652 nm: 672 nm), Cy5.5 (682 nm; 703 nm) and Cy7 (755 nm; 778 nm), thus allowing their simultaneous detection. The fluorescent labels can be obtained from a variety of commercial sources, including Molecular Probes, Eugene, OR and Research Organics, Cleveland, Ohio.

In some instances, a label sequence can be, but is not limited to, an isotope marker, colorimetric biosensors, or fluorescent labels. For example, fluorescent markers can be, but are not limited to, green fluorescent protein (GFP) or rhodamine fluorescent protein (RFP). Other label sequences can include biotin, streptavidin, horseradish peroxidase, or luciferase.

In some instances, a tag sequence can be a purification tag. In some instances, a purification tag can be, but is not limited to, histidine, glutathione-S-transferase, albumin-binding protein, FLAG epitope, galactose-binding protein, myc, or hemagglutinin.

C. Compositions

Disclosed are compositions comprising any of the disclosed peptides. In some instances, disclosed are compositions comprising a monomeric Fc fragment of an immunoglobulin recognized by a FcRn; an influenza protein; and a trimerization domain.

In some instances, the composition can be a vaccine.

In some instances, the compositions can further comprise a pharmaceutically acceptable carrier. By "pharmaceutically acceptable" is meant a material or carrier that would be selected to minimize any degradation of the active ingredient and to minimize any adverse side effects in the subject, as would be well known to one of skill in the art. Examples of carriers include dimyristoylphosphatidyl (DMPC), phosphate buffered saline or a multivesicular liposome. For example, PG:PC:Cholesterol:peptide or PC:peptide can be used as carriers in this invention. Other suitable pharmaceutically acceptable carriers and their formulations are described in Remington: The Science and Practice of Pharmacy (19th ed.) ed. A. R. Gennaro, Mack Publishing Company, Easton, PA 1995. Typically, an appropriate amount of pharmaceutically-acceptable salt is used in the formulation to render the formulation isotonic. Other examples of the pharmaceutically-acceptable carrier include, but are not limited to, saline, Ringer's solution and dextrose solution. The pH of the solution can be from about 5 to about 8, or from about 7 to about 7.5. Further carriers include sustained release preparations such as semi-permeable matrices of solid hydrophobic polymers containing the composition, which matrices are in the form of shaped articles, e.g., films, stents (which are implanted in vessels during an angioplasty procedure), liposomes or microparticles. It will be apparent to those persons skilled in the art that certain carriers may be more preferable depending upon, for instance, the route of administration and concentration of composition being administered. These most typically would be standard carriers for administration of drugs to humans, including solutions such as sterile water, saline, and buffered solutions at physiological pH.

Pharmaceutical compositions can also include carriers, thickeners, diluents, buffers, preservatives and the like, as long as the intended activity of the polypeptide, peptide, nucleic acid, vector of the invention is not compromised. Pharmaceutical compositions may also include one or more active ingredients (in addition to the composition of the invention) such as antimicrobial agents, anti-inflammatory agents, anesthetics, and the like. The pharmaceutical composition may be administered in a number of ways depending on whether local or systemic treatment is desired, and on the area to be treated.

Preparations of parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for optical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids, or binders may be desirable. Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mon-, di-, trialkyl and aryl amines and substituted ethanolamines.

The disclosed peptides can be formulated and/or administered in or with a pharmaceutically acceptable carrier. As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug (e.g. peptide) in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions that are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

Thus, the compositions disclosed herein can comprise lipids such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a peptide and a cationic liposome can be administered to the blood, to a target organ, or inhaled into the respiratory tract to target cells of the respiratory tract. For example, a composition comprising a peptide or nucleic acid sequence described herein and a cationic liposome can be administered to a subject's lung cells. Regarding liposomes, see, e.g., Brigham et al. Am. J. Resp. Cell. Mol. Biol. 1:95 100 (1989); Felgner et al. Proc. Natl. Acad. Sci USA 84:7413 7417 (1987); U.S. Pat. No. 4,897,355. Furthermore, the compound can be administered as a component of a microcapsule that can be targeted to specific cell types, such as macrophages, or where the diffusion of the compound or delivery of the compound from the microcapsule is designed for a specific rate or dosage.

In some instances, disclosed are pharmaceutical compositions comprising any of the disclosed peptides described herein, or a pharmaceutically acceptable salt or solvate thereof, and a pharmaceutically acceptable carrier, buffer, or diluent. In various aspects, the peptide of the pharmaceutical composition is encapsulated in a delivery vehicle. In a further aspect, the delivery vehicle is a liposome, a microcapsule, or a nanoparticle. In a still further aspect, the delivery vehicle is PEG-ylated.

In the methods described herein, delivery of the compositions to cells can be via a variety of mechanisms. As defined above, disclosed herein are compositions comprising any one or more of the peptides described herein and can also include a carrier such as a pharmaceutically acceptable carrier. For example, disclosed are pharmaceutical compositions, comprising the peptides disclosed herein, and a pharmaceutically acceptable carrier. In one aspect, disclosed are pharmaceutical compositions comprising the disclosed peptides. That is, a pharmaceutical composition can be provided comprising a therapeutically effective amount of at least one disclosed peptide or at least one product of a disclosed method and a pharmaceutically acceptable carrier.

In certain aspects, the disclosed pharmaceutical compositions comprise the disclosed peptides (including pharmaceutically acceptable salt(s) thereof) as an active ingredient, a pharmaceutically acceptable carrier, and, optionally, other therapeutic ingredients or adjuvants. The instant compositions include those suitable for nasal, oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

In practice, the peptides described herein, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

By "pharmaceutically acceptable" is meant a material or carrier that would be selected to minimize any degradation of the active ingredient and to minimize any adverse side effects in the subject, as would be well known to one of skill in the art. The peptides described herein, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen. Other examples of carriers include dimyristoylphosphatidyl (DMPC), phosphate buffered saline or a multivesicular liposome. For example, PG:PC:Cholesterol:peptide or PC:peptide can be used as carriers in this invention. Other suitable pharmaceutically acceptable carriers and their formulations are described in Remington: The Science and Practice of Pharmacy (19th ed.) ed. A. R. Gennaro, Mack Publishing Company, Easton, Pa. 1995. Typically, an appropriate amount of pharmaceutically-acceptable salt is used in the formulation to render the formulation isotonic. Other examples of the pharmaceutically-acceptable carrier include, but are not limited to, saline, Ringer's solution and dextrose solution. The pH of the solution can be from about 5 to about 8, or from about 7 to about 7.5. Further carriers include sustained release preparations such as semi-permeable matrices of solid hydrophobic polymers containing the composition, which matrices are in the form of shaped articles, e.g., films, stents (which are implanted in vessels during an angioplasty procedure), liposomes or microparticles. It will be apparent to those persons skilled in the art that certain carriers may be more preferable depending upon, for instance, the route of administration and concentration of composition being administered. These most typically would be standard carriers for administration of drugs to humans, including solutions such as sterile water, saline, and buffered solutions at physiological pH.

In order to enhance the solubility and/or the stability of the disclosed peptides in pharmaceutical compositions, it can be advantageous to employ α-, β- or γ-cyclodextrins or their derivatives, in particular hydroxyalkyl substituted cyclodextrins, e.g. 2-hydroxypropyl-β-cyclodextrin or sulfobutyl-β-cyclodextrin. Also, co-solvents such as alcohols may improve the solubility and/or the stability of the compounds according to the invention in pharmaceutical compositions.

Pharmaceutical compositions can also include carriers, thickeners, diluents, buffers, preservatives and the like, as long as the intended activity of the polypeptide, peptide, nucleic acid, vector of the invention is not compromised. Pharmaceutical compositions may also include one or more active ingredients (in addition to the composition of the invention) such as antimicrobial agents, anti-inflammatory agents, anesthetics, and the like. The pharmaceutical composition may be administered in a number of ways depending on whether local or systemic treatment is desired, and on the area to be treated.

Because of the ease in administration, oral administration can be used, and tablets and capsules represent the most advantageous oral dosage unit forms in which case solid pharmaceutical carriers are obviously employed. In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques.

Compositions for oral administration include powders or granules, suspensions or solutions in water or non-aqueous media, capsules, sachets, or tablets. Thickeners, flavorings, diluents, emulsifiers, dispersing aids, or binders may be desirable. Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mon-, di-, trialkyl and aryl amines and substituted ethanolamines.

A tablet containing the compositions of the present invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a disclosed peptide (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. Typically, the final injectable form should be sterile and should be effectively fluid for easy syringability. The pharmaceutical compositions should be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Injectable solutions, for example, can be prepared in which the carrier comprises saline solution, glucose solution or a mixture of saline and glucose solution. Injectable suspensions may also be prepared in which case appropriate liquid carriers, suspending agents and the like may be employed. Also included are solid form preparations that are intended to be converted, shortly before use, to liquid form preparations.

Preparations of parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot on, as an ointment.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

Formulations for optical administration may include ointments, lotions, creams, gels, drops, suppositories, sprays, liquids and powders. Conventional pharmaceutical carriers, aqueous, powder or oily bases, thickeners and the like may be desirable.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a disclosed peptide, and/or pharmaceutically acceptable salts thereof, can also be prepared in powder or liquid concentrate form.

The exact dosage and frequency of administration depends on the particular disclosed peptide, a product of a disclosed method of making, a pharmaceutically acceptable salt, solvate, or polymorph thereof, a hydrate thereof, a solvate thereof, a polymorph thereof, or a stereochemically isomeric form thereof, the particular condition being treated and the severity of the condition being treated; various factors specific to the medical history of the subject to whom the dosage is administered such as the age; weight, sex, extent of disorder and general physical condition of the particular subject, as well as other medication the individual may be taking; as is well known to those skilled in the art. Furthermore, it is evident that said effective daily amount may be lowered or increased depending on the response of the treated subject and/or depending on the evaluation of the physician prescribing the compositions.

Depending on the mode of administration, the pharmaceutical composition will comprise from 0.05 to 99% by weight, preferably from 0.1 to 70% by weight, more preferably from 0.1 to 50% by weight of the active ingredient, and, from 1 to 99.95% by weight, preferably from 30 to 99.9% by weight, more preferably from 50 to 99.9% by weight of a pharmaceutically acceptable carrier, all percentages being based on the total weight of the composition.

D. Nucleic Acid Sequences

As this specification discusses various peptide sequences it is understood that the nucleic acids that can encode those polypeptide sequences are also disclosed. This would include all degenerate sequences related to a specific polypeptide sequence, i.e. all nucleic acids having a sequence that encodes one particular polypeptide sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed polypeptide sequences.

Disclosed are nucleic acid sequences capable of encoding any of the peptides disclosed herein. Further disclosed are nucleic acid constructs comprising the nucleic acid sequences capable of encoding any of the peptides disclosed herein.

Disclosed are vectors comprising a nucleic acid sequence capable of encoding peptides comprising a monomeric Fc fragment of an immunoglobulin recognized by a FcRn; a influenza protein; and a trimerization domain. In some instances, the peptide can be any of the peptides disclosed herein.

In some instances, the disclosed vectors can further comprise a nucleic acid sequence capable of encoding a tag (e.g. label or purification tag). In some aspects, the label can be any peptide or protein that is encoded for by a nucleic acid. For example, the labeling moiety can be, but is not limited to, GST, myc, His, or GFP.

In some instances, the labeling moiety can be operably linked to the nucleic acid sequence capable of encoding the peptides comprising a monomeric Fc fragment of an immunoglobulin recognized by a FcRn; a influenza protein; and a trimerization domain. Thus, the labeling moiety and the peptide can be transcribed together.

In addition to a nucleic acid sequence capable of encoding the disclosed peptides, the disclosed vectors can carry regulatory sequences that control the expression of the disclosed peptides in a host cell. It will be appreciated by those skilled in the art that the design of the vector, including the selection of regulatory sequences can depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from retroviral LTRs, cytomegalovirus (CMV) (such as the CMV promoter/enhancer), Simian Virus 40 (SV40) (such as the SV40 promoter/enhancer), adenovirus, (e.g., the adenovirus major late promoter (AdMLP)), polyoma and strong mammalian promoters such as native immunoglobulin and actin promoters. For further description of viral regulatory elements, and sequences thereof, see e.g., U.S. Pat. Nos. 5,168,062, 4,510,245 and 4,968,615. Methods of expressing polypeptides in bacterial cells or fungal cells, e.g., yeast cells, are also well known in the art.

In some instances, the disclosed vectors further comprise a promoter operably linked to the nucleic acid sequence capable of encoding the disclosed peptides. In some instances, the promoter can be an inducible promoter. In some instances, the promoter can be a cell-specific promoter. The nucleic acid sequence capable of encoding the disclosed peptides can be functionally linked to a promoter. By "functionally linked" is meant such that the promoter can promote expression of the nucleic acid sequence, thus having appropriate orientation of the promoter relative to the nucleic acid sequence.

E. Methods

Disclosed are methods for eliciting a protective immune response against influenza comprising administering to a subject an effective amount of a composition comprising any of the peptides, nucleic acids or vectors disclosed herein.

Disclosed are methods for eliciting a protective immune response against influenza comprising administering to a subject an effective amount of a composition comprising a monomeric Fc fragment of an immunoglobulin recognized by a FcRn; an influenza HA protein; and a trimerization domain, wherein the administering is to a mucosal epithelium.

In some instances, the mucosal epithelium is selected from the group consisting of: lungs, intestines, trachea, colon, nasal tissue, and vaginal tissue.

In some instances, administering is intranasal administering. In some instances, any form of administering that allows for delivery to a mucosal epithelium can be used.

In some instances, an adjuvant is further administered with the composition. In some instances, an adjuvant can be formulated with the peptide into the disclosed compositions. Thus, the adjuvant can be administered simultaneously with the peptide. In some instances, the adjuvant is separate from the disclosed compositions and therefore can be administered simultaneously with the composition or separate from the composition. The adjuvant can be, for example, but is not limited to, CpG, MPL, poly[di(sodium carboxylatoethylphenoxy)phosphazene] (PCEP), poly[di(sodium carboxylatophenoxy)phosphazene] (PCPP), the Cholera Toxin-Derived CTA1-DD, Flagellin, IDR1002, α-Galactosylceramide, or saponins.

In some instances, the trimerization domain of the peptide administered to the subject is a T4 fibritin trimerization domain.

Disclosed are methods of treating a subject exposed to influenza or at risk of being exposed to influenza comprising administering to the subject an effective amount of a composition comprising a monomeric Fc fragment of an immunoglobulin recognized by a FcRn; an influenza HA protein; and a trimerization domain, wherein the administering is to a mucosal epithelium. In some instances, any of the disclosed peptides can be administered a part of a composition or pharmaceutical composition to the subject for treatment.

F. Combination Therapy

In one aspect of the disclosed methods, the compositions can be administered alone or in combination with one or more additional therapeutic agents. The additional therapeutic agents are selected based on the disease or symptom to be treated. A description of the various classes of suitable pharmacological agents and drugs may be found in Goodman and Gilman, The Pharmacological Basis of Therapeutics, (11th Ed., McGraw-Hill Publishing Co.) (2005).

G. Kits

The compositions and materials described above as well as other materials can be packaged together in any suitable combination as a kit useful for performing, or aiding in the performance of, the disclosed method. It is useful if the kit components in a given kit are designed and adapted for use together in the disclosed method. For example disclosed are kits for producing the disclosed peptides, the kit comprising monomeric Fc fragment of an immunoglobulin recognized by a.FcRn and an influenza protein. The kits also can contain vectors.

Examples

The respiratory tract is a common site for pathogen exposure. The respiratory tract can resist infection and facilitate the clearance of invading pathogens through a variety of mechanisms, including the airway barrier of polarized epithelial cells and various innate or adaptive immune responses (1, 2). Adaptive immunity, including effector and memory T or B lymphocytes and local and circulating Abs, can prevent infections or decrease the severity of subsequent respiratory infections (3, 4). For example, tissue-resident memory (TRM) T cells that reside in the lung are a recently appreciated subset of memory T cells and are required for optimal protection against previously encountered pathogens (5-7). Presently, most vaccines against respiratory infections are designed for delivery via parenteral routes including the muscle or skin, for intended protection of the lung. However, non-mucosal delivery routes elicit relatively poor mucosal immune responses in the respiratory tract, even though they often induce robust systemic immunity (8-11). A partial reason for the failure of systemic vaccination is the lack of strong mucosal Ab and cell-mediated immunity, including TRM T cells that reside in the lung tissue and their availability in the event of pathogen exposure. To prevent respiratory infections, an ideal way is to develop a mucosal vaccine that mimics natural respiratory infections and engenders beneficial lung immunity. This goal is best achieved by direct administration of vaccines via the respiratory route (12, 13). However, the ability to safely and effectively deliver vaccine antigens across the respiratory mucosal barrier is limited. Mucosal vaccines must avoid inducing excessively robust inflammatory responses that may lead to lung damage and exacerbate chronic diseases such as asthma or chronic obstructive pulmonary disease. Since respiratory infections are more prevalent in the young and elderly individuals, certain types of mucosal vaccines such as live attenuated vaccines, are not preferred for these vulnerable populations. Given the high impact of respiratory infections on public health, developing safe and effective mucosal vaccines is an urgent, unmet need (12).

Epithelial monolayers lining the respiratory, intestinal, and genital tracts, as well as the placenta, polarize into the apical and basolateral plasma membrane domains, which are separated by intercellular tight junctions. The neonatal Fc receptor (FcRn) is expressed in these epithelial monolayers and mediates the transfer of IgG Ab across the epithelium (14-16). By transcytosing IgG, FcRn provides a line of humoral defense at mucosal surfaces (16, 17-19), in addition to transferring maternal immunity to neonates. A hallmark of FcRn is its interaction with IgG Ab in a pH-dependent manner, binding IgG at acidic pH (6.0-6.5) and releasing IgG at neutral or higher pH (20). FcRn primarily resides within low pH endosomes and binds IgG through the Fc region. Normally, IgG enters epithelial cells via pinocytotic vesicles that fuse with acidic endosomes. IgG bound to FcRn then enters a non-degradative vesicular transport pathway within epithelial cells. Bound IgG is transported to the apical or basolateral surface and released into the lumen or submucosa upon physiological pH (21). Evidence of IgG transport across the respiratory epithelia by FcRn suggest that FcRn might also transport a vaccine antigen from a respiratory pathogen, if fused with the Fc portion of IgG, across the respiratory mucosal barrier.

To test this possibility, influenza A virus was used as a model respiratory pathogen. The hemagglutinin (HA) primarily mediates interactions of influenza virions with cell surface sialic acid residue receptors. After binding, virions are internalized through endocytic pathways to infect epithelial cells. The HA protein consists of the membrane-distal immunodominant globular head domain and the membrane-proximal HA stalk domain. The head domain shows high structural plasticity which is strongly affected by antigenic drift; in contrast, the stalk domain exhibits a high degree of conservation. HA plays a critical role in the early steps of viral infection and as the major antigen for eliciting both humoral and cellular immunity. In this study, the ability of FcRn to deliver the viral HA protein fused to an Fc region of IgG across the respiratory epithelial barrier was determined. Protective immune responses and mechanisms relevant to this route for mucosal vaccination in the lung were defined in a mouse model. The data suggest that FcRn-mediated intranasal delivery of influenza virus HA antigen induces high levels of long-lasting Ab and T-cell responses, including TRM T cells in the lung, to provide potent protection against lethal influenza virus challenge. The data demonstrate that FcRn-targeted delivery of an influenza virus vaccine antigen in the respiratory tract comprises an effective vaccine strategy and can be developed as a universal influenza vaccine against seasonal infection or for protection against pandemic influenza viruses or other common respiratory infections.

Figures 1A, 1B, 1C, 1D:
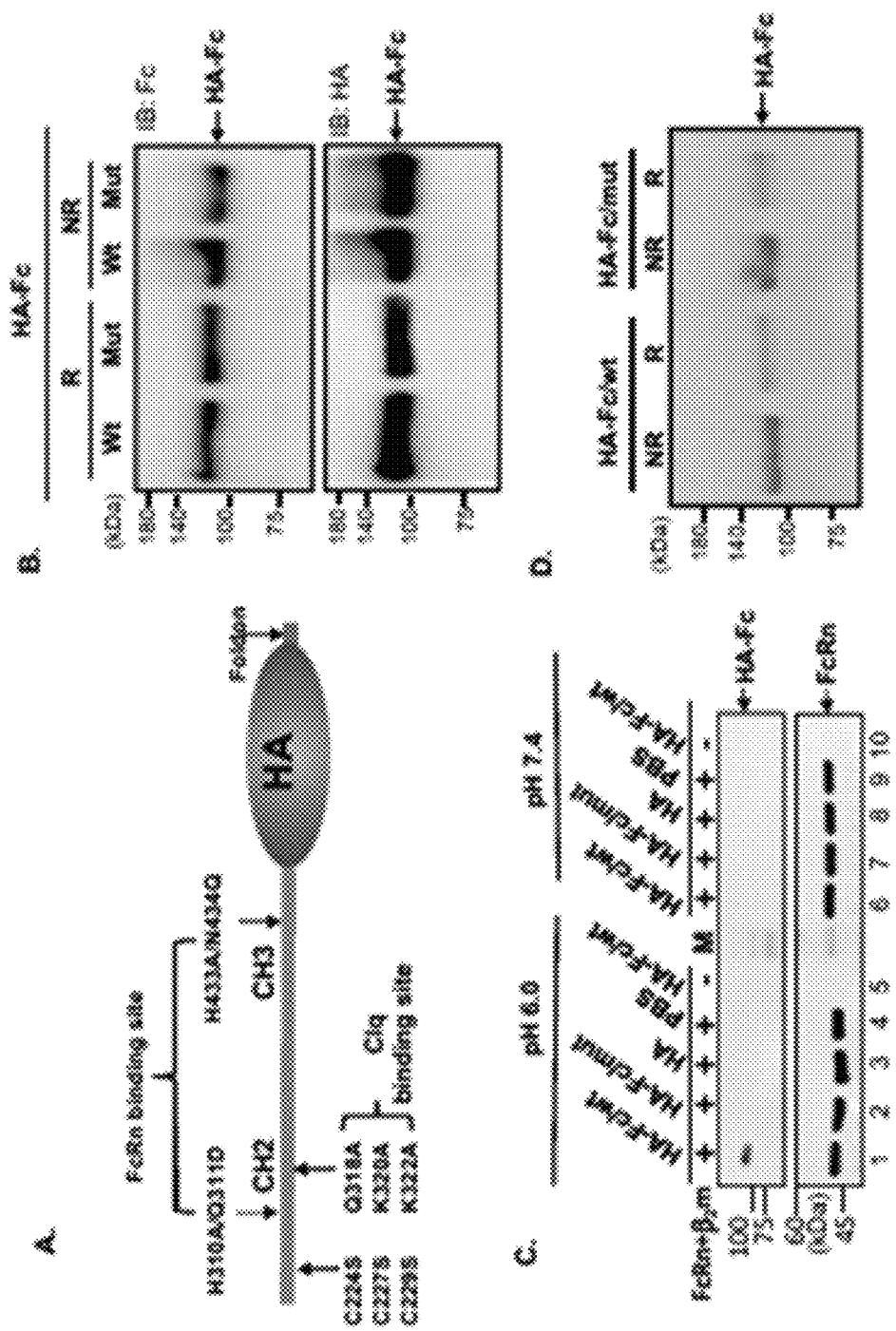
FIGS. 1A-1G. Expression and characterization of the trimeric HA-Fc fusion proteins. (A). Schematic illustration of the genetic fusion of influenza HA, the T4 fibritin foldon domain (Fd), and murine FcΔ2a cDNA to create a trimeric HA-Fc fusion gene. Mutations were made in the FcΔ2a fragment using site-directed mutagenesis by replacing Cys224, Cys227, and Cys229 respectively with a Ser residue to abolish Fc dimerization, and replacing Glu318, Lys320, and Lys322 with an Ala residue to deplete complement C1q binding site. His310/Gln311 (HQ) and His433/Asn434 (HN) residues were replaced with Ala310/Asp311 (AD) and Ala433/Gln434 (AQ) to eliminate FcRn binding sites, this plasmid was designated as HA-Fc/mut. (B). The HA-Fc fusion protein secreted by a stable CHO cell line. The HA-Fc were subjected to SDS-PAGE and Western blot analyses and detected by either goat anti-mouse IgG-Fc (top panel) or an anti-HA mAb (bottom panel). The fusion protein was shown as a monomer under both non-reducing (NR) and reducing (R) conditions. (C). FcRn binding of the HA-Fc. CHO cells expressing mouse FcRn and β2m were incubated with 3 μg HA-Fc/wt, HA-Fc/mut, or HA protein for 1 hr at 4° C. under pH 6.0 or pH 7.4 condition. After washing, the cells were lysed with 0.5% CHAPS in cold PBS (pH 6.0 or 7.4). Samples were subjected to Western blot analysis. The HA-Fc or HA (top) or mouse FcRn (bottom) was detected with anti-HA or anti-mouse FcRn primary Ab and HRP-conjugated secondary Ab. (D). The HA-Fc/wt and HA-Fc/mut were purified by affinity chromatography and visualized with Coomassie blue staining. (E). Western blot analysis of the purified HA-Fc that was cross-linked with BS3. The BS3-treated (left & middle panel) or -untreated (right panel) samples were separated by SDS-PAGE under reducing conditions followed by Western blotting using anti-Fc Ab (left & right panels) or anti-HA Ab (middle panel). (F). Stable CHO cell lines expressing HA-Fc/wt and HA-Fc/mut were probed with conformation-dependent anti-HA mAbs. CHO cells were transfected with HA-Fc plasmids and fixed with 4% paraformaldehyde. Cells were then incubated with HA-specific mAb 6F12 (top panel) or KB2 (bottom panel) and visualized using immunofluorescence staining. (G). Interactions of the purified HA-Fc with a panel of HA stalk-specific and conformation-dependent Abs CR6261, FI6v3, 6F12, or CR8020. The specific binding was detected by ELISA method. HIV gp120 specific IgG mAb B12 was used as a negative control.

1. Results i. Expression and Characterization of Influenza HA-Fc Fusion Proteins To activate virus infectivity, the HA precursor molecule HA0 is cleaved into HA1 and HA2 (22). To produce the non-cleavable HA0 protein, mutagenesis at the cleavage sites (SIQS→QRET) of PR8 HA ensured that the expressed HA would remain in the HA0 pre-cleavage state. The HA exists as a trimer on the virions or virally infected cells. It is likely that a trimeric HA antigen fused to an Fc would more closely mimic a native HA structure. Because IgG Fc forms a disulfide-bond dimer, we created a monomeric Fc by eliminating the disulfide bonds formed by three cysteines at positions 224, 227, and 229 by substituting with serine residues. An Fc mutant that was unable to bind FcRn owing to histidine residue substitutions at positions 310 and 433 was also generated (FIG. 1A; 23). In both wild-type (wt) and mutant (mut) Fc for FcRn binding, the complement C1q-binding motif was eliminated (24) (FIG. 1A). To facilitate trimerization, a foldon domain was engineered from T4 bacteriophage fibritin (25) to the C-terminus of HA0. The monomeric IgG Fc/wt or Fc/mut was fused in frame with the HA0-Foldon, respectively (FIG. 1A), generating plasmids that expressed trimeric HA-Fc/wt or HA-Fc/mut proteins.

Figures 8A, 8B, 8C:
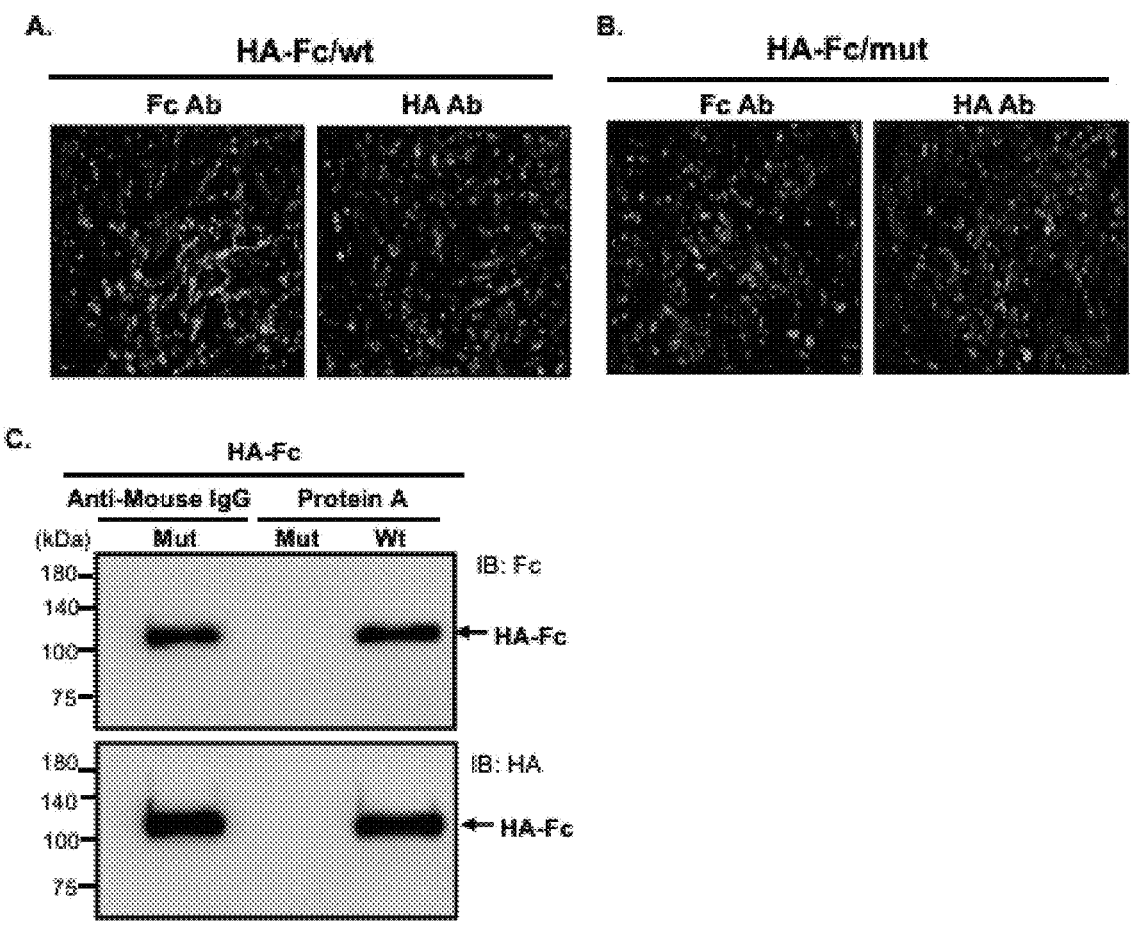
FIGS. 8A-C. Stable CHO cell lines are established to secrete the trimeric HA-Fc proteins. After transfection with the recombinant plasmids, CHO cell lines were established under G418 (1 mg/ml) selection. The trimeric HA-Fc/wt (A) or HA-Fc/mut (B) expression were stained by immunofluorescence assay using either an antibody against HA or mouse IgG2a Fc. (C). Protein A-pull-down of the trimeric HA-Fc. The ability of HA-Fc to interact with staphylococcal Protein A was assessed, as the IgG Fc binding sites for both FcRn and Protein A overlap. The 500 ng HA-Fc/wt or HA-Fc/mut was incubated with Protein A resin slurry or anti-mouse IgG conjugated Agarose beads for 2 h at 4° C. Samples were eluted and subjected to SDS-PAGE and Western blot analyses and probed with anti-Fc Ab (top panel) or anti-HA Ab (bottom panel). As expected, the HA-Fc/mut protein was pulled down by anti-mouse IgG beads. However, the HA-Fc/wt, but not HA-Fc/mut, proteins interacted with Protein A.

Both secreted HA-Fc/wt and HA-Fc/mut proteins from stable CHO cells (FIG. 8A+8B) were monomers under reducing or non-reducing conditions (FIGS. 1B and 1D), indicating the removal of the disulfide bonds in the Fc. FcRn binds IgG at acidic pH but not neutral pH conditions (21). To determine whether HA-Fc/wt or HA-Fc/mut protein binds to FcRn, CHO cells expressing mouse FcRn and β2m were incubated with 3 μg HA-Fc/wt, HA-Fc/mut, or HA protein under pH 6.0 or pH 7.4 condition for 1 hr at 4° C. In this way, FcRn at the cell surface would bind the HA-Fc proteins only at pH 6.0. As shown in FIG. 1C, the HA-Fc/wt and FcRn proteins were detected with anti-HA or anti-FcRn specific Ab (lane 1). However, the HA-Fc/mut (lane 2) or HA (lane 3) proteins were not found. Therefore, HA-Fc/wt protein maintains the structural integrity required to interact with FcRn.

Figure 1E:
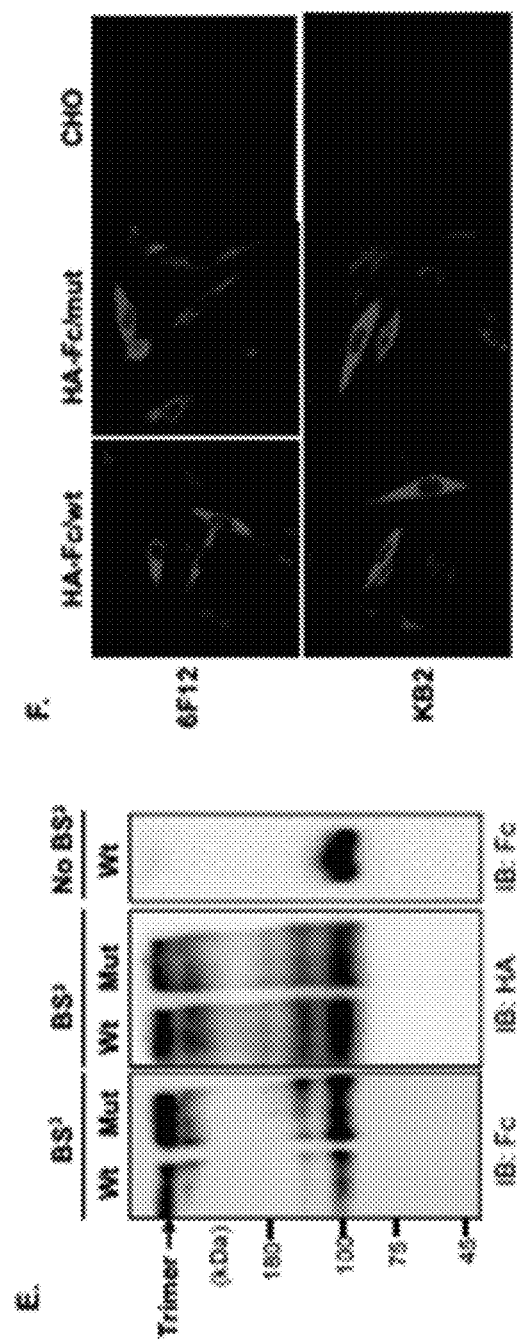
Figure 1F:
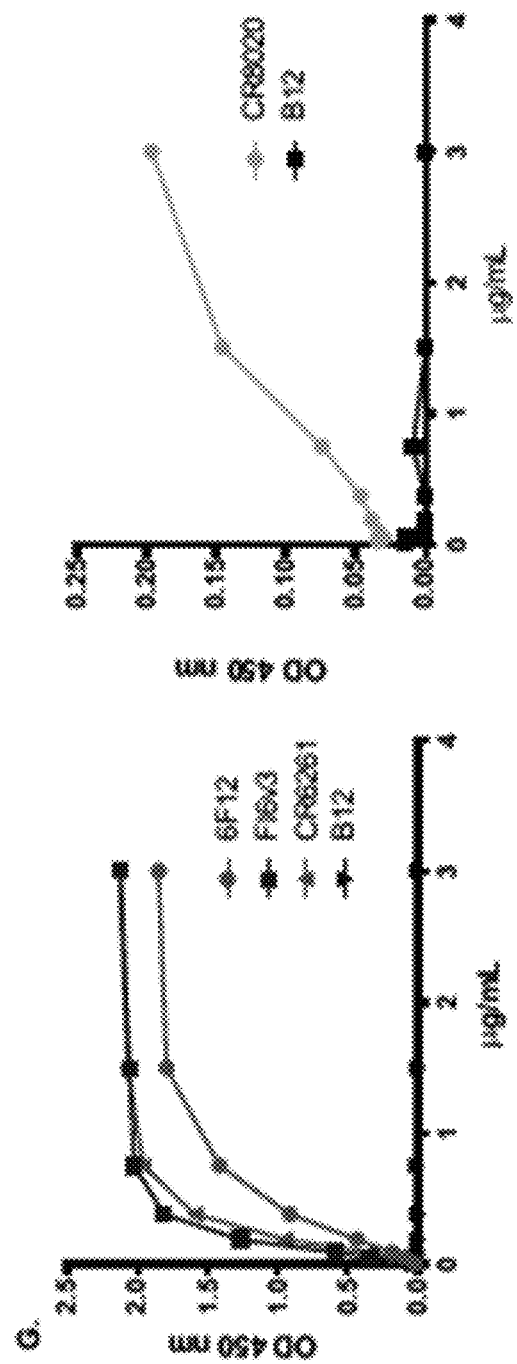
Figure 1G:
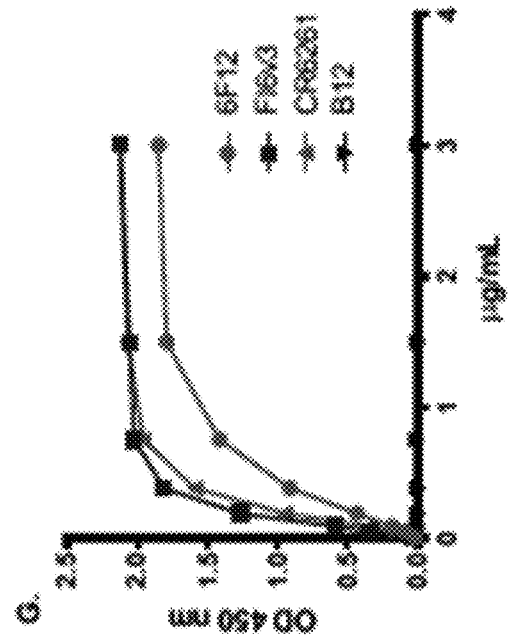
Figures 2A, 2B, 2C, 2D, 2E, 2F:
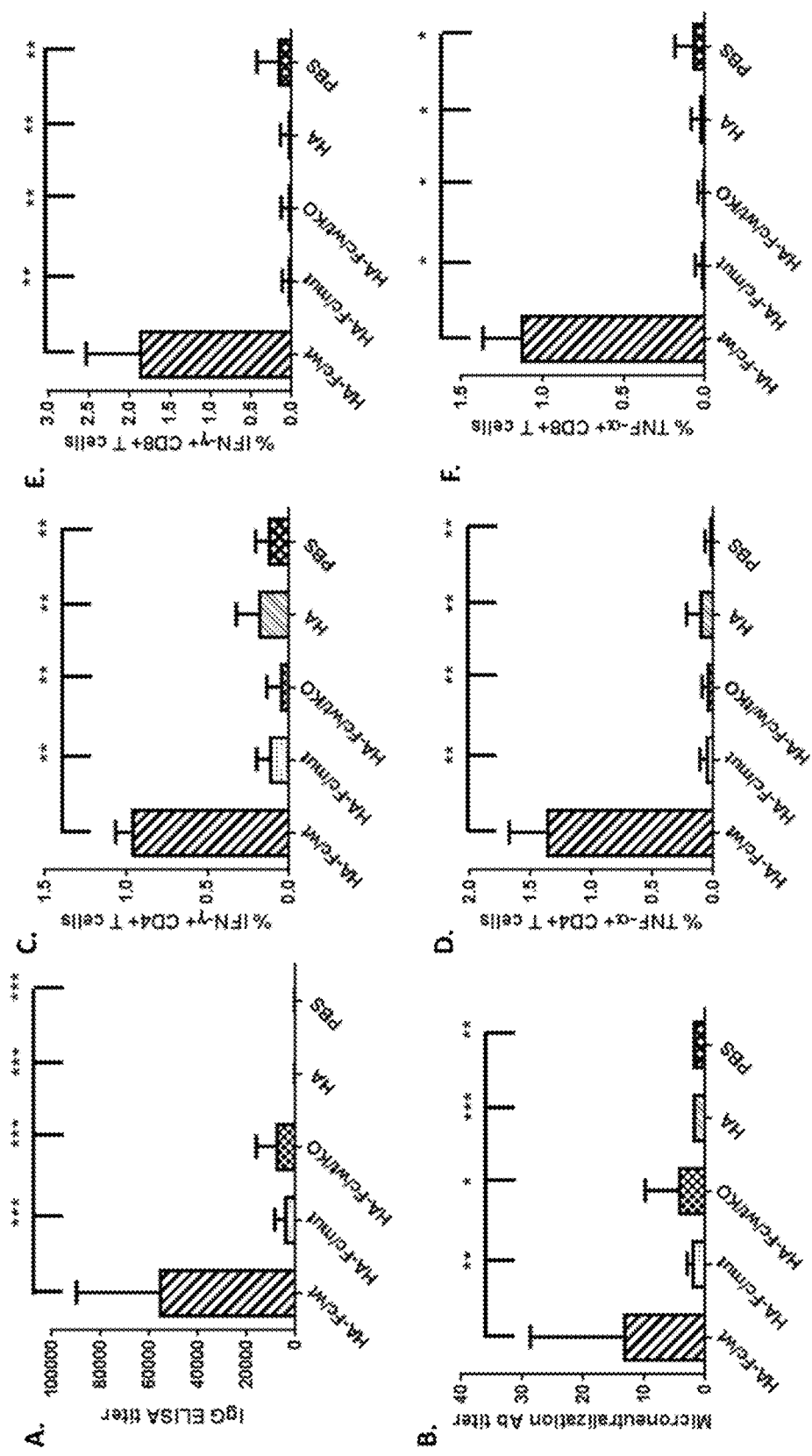
FIGS. 2A-F. FcRn-mediated respiratory immunization induces HA-specific Ab and T cell immune responses. Five g of HA-Fc/wt, HA-Fc/mut, HA, or PBS in combination with g of CpG were i.n. administered into wild-type (WT) or FcRn knockout (KO) mice. Values marked with asterisks in the figures: *, P<0.05; , P<0.01, *, P<0.001. Immunization conditions are displayed on the bottom. (A). Measurement of anti-influenza HA-specific IgG Ab titers in serum after the booster immunization. Influenza HA-specific Ab titers were measured by ELISA 14 days after boosting. The IgG titers were measured in 10 representative mouse sera. The data represent mean±S.E.M. (B). Test of neutralizing Ab activity in the immunized sera. Two weeks after boost, sera sampled from 13 to 20 mice per group were heat-inactivated, diluted twofold in PBS with antibiotics/antimycotics. Influenza PR8 (100 TCID50) was added and incubated at 37° C. for 1 hr the mixture was added to MDCK cells and incubated at 37° C. and subsequently removed after 1 hr. The serum-free Opti-MEM containing 1 µg/ml TPCK-trypsin was added to cells. After incubation at 37° C. for 72 hr, an HA assay was performed on the supernatant. The neutralization Ab titers were expressed as the reciprocal of the twofold serial dilution preventing the appearance of the agglutination of the erythrocytes of chicken. Each assay was performed in triplicate (C, D, E, & F). The percentage of IFN-7 and TNF-α producing T cells in the lung 7 days after the boost. The lung lymphocytes from the immunized mice were stimulated for 10 hr with purified HA or medium control. Lymphocytes were gated by forward and side scatters and T cells labeled with anti-CD3 and identified by their respective surface markers CD4 and CD8 and intracellular IFN-γ or TNF-α staining. Numbers represent the percentage of IFN-γ+CD4+(C), TNF-α+CD4+(D), IFN-γ+CD8+(E), or TNF-α+CD8+(F) T cells. Isotype controls included FITC-mouse-IgG1 with baseline response. Flow cytometry plots are representative of two independent experiments with 4 immunized mice pooled in each group. Graphical data is the average percentage of the two experiments.
Figures 3A, 3B, 3C:
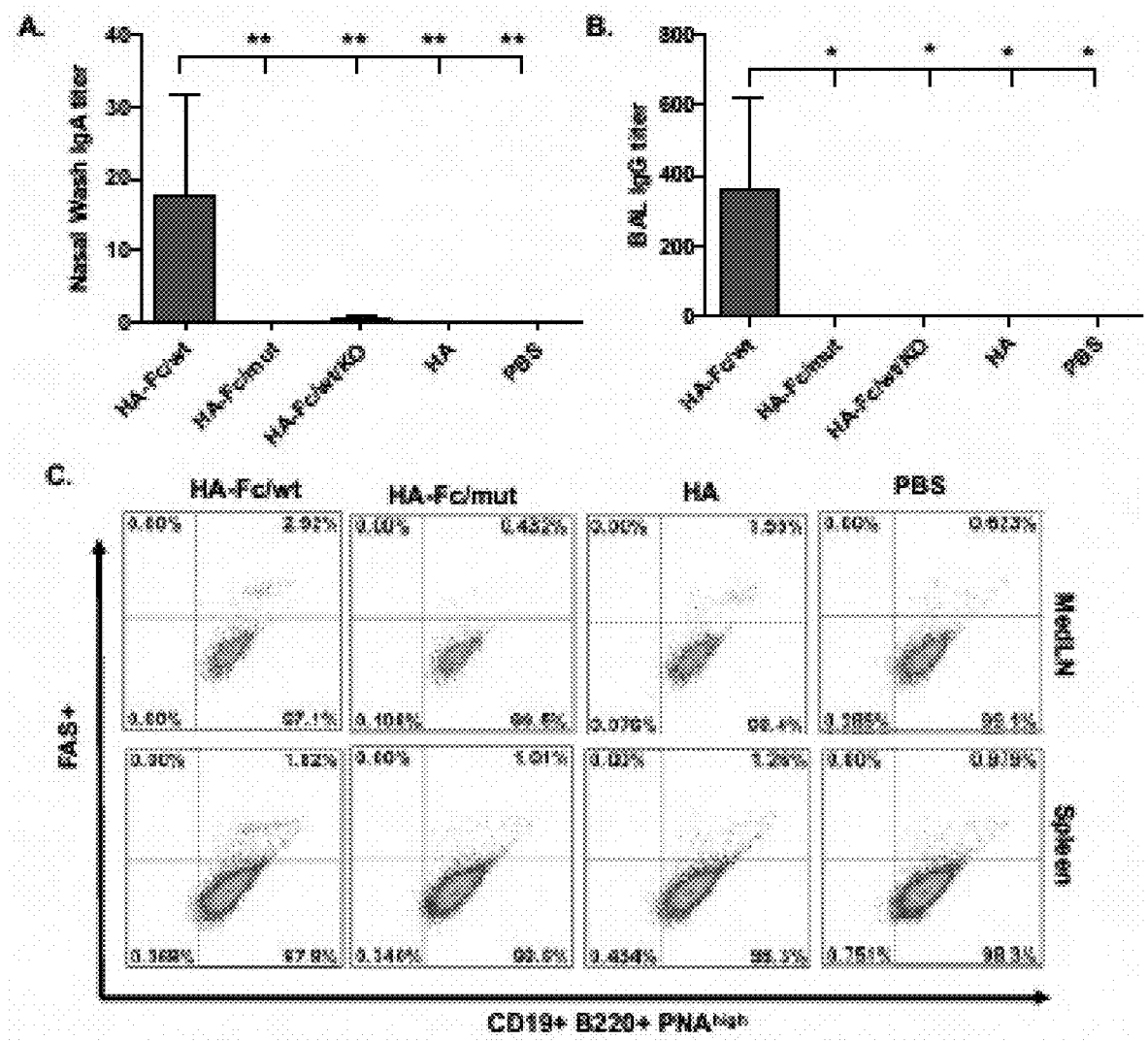
FIGS. 3A-C. FcRn-mediated intranasal vaccination significantly induced HA-specific local immune responses in the respiratory tract (A & B). Measurement of anti-influenza HA-specific Ab titers in nasal washings (A, IgA), and BAL (B, IgG) after the boost. Influenza HA-specific Abs were measured by ELISA 14 days after boost. The Ab titer was measured in 10 representative mouse samples. The data represent mean values for each group (±S.E.M.). (C). Accumulation of activated B cells in germinal centers (GCs) in the mediastinal lymph nodes (MedLNs) and spleens. Representative flow cytometric analyses of GC B cells among CD19+B220+ B cells in the MedLNs and spleens 10 days after the boost. B220+PNAhigh cells are B cells that exhibit the phenotypic attributes of GC B cells. The GC staining in the spleen was used as a positive control. GC B cells are pooled from individual mouse because of the limited cell numbers isolated from each MedLN. Numbers are the percentage of activated GC B cells (PNA+FAS+) among gated B cells and are representative of three independent experiments.
Figure 4A:
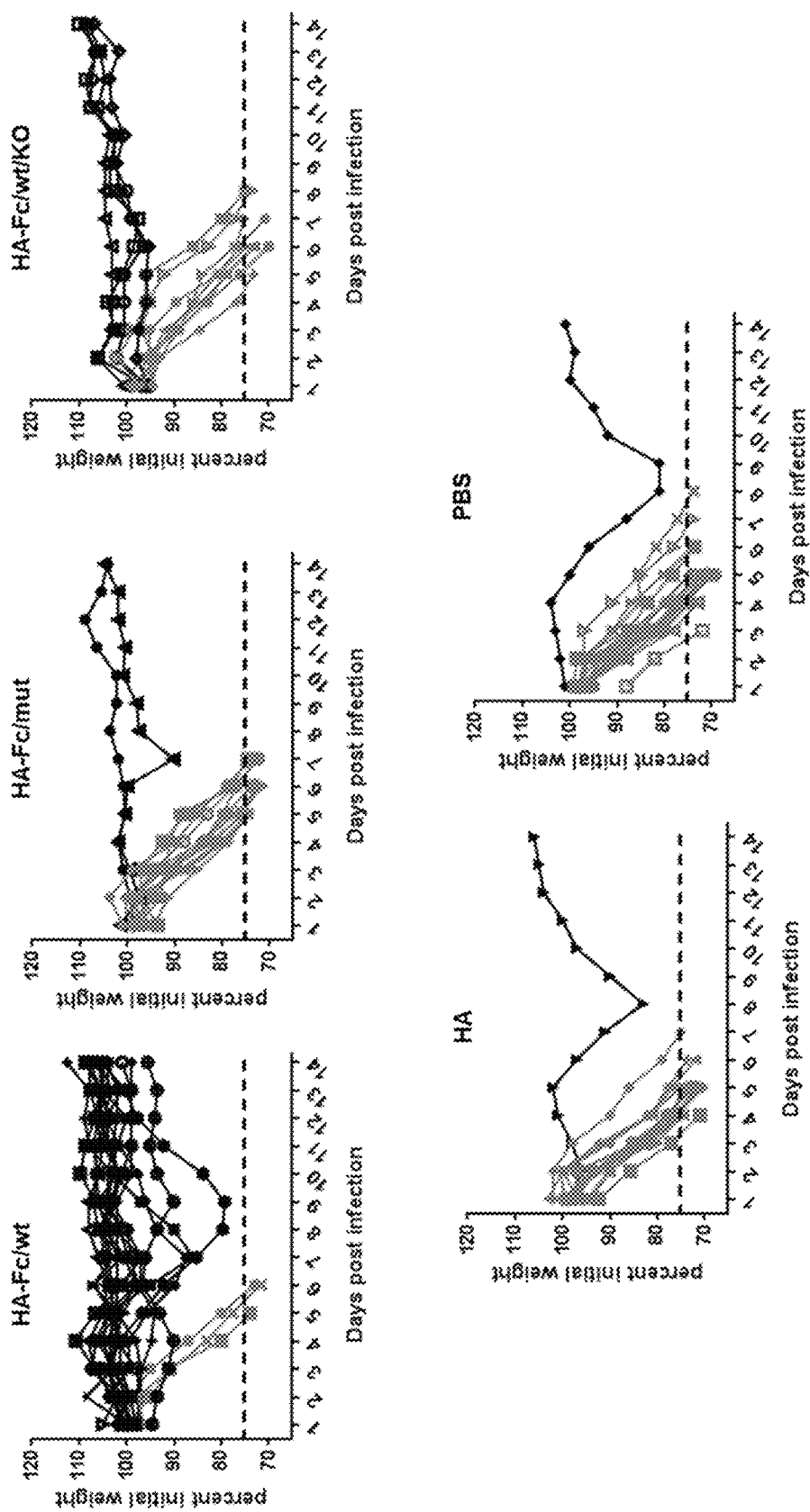
FIGS. 4A-C. FcRn-targeted respiratory immunization engenders protective immunity to intranasal (i.n.) challenge with virulent influenza virus. (A). Body-weight changes following influenza challenge. Two weeks after the boost, groups of 13-20 mice were i.n. challenged with PR8 virus (5 MLD50) and weighed daily for 14 days. Mice were deceased or humanely euthanized if more than 25% of initial body weight was lost. The data is representative of at least three similar experiments. (B) Mean survival following influenza challenge. Two weeks after the boost, groups of 13-20 mice were i.n. challenged with PR8 virus (5 MLD50) and weighed daily for 14 days. Mice were humanely euthanized if more than 25% of initial body weight was lost. The percentage of mice from protection after the challenge was shown by the Kaplan-Meier survival curve. The data is representative of at least three similar experiments. Statistical differences were determined using multiple Mantel-Cox tests. (C) Mean of viral titers in the lungs following influenza virus challenge. The virus titers in the lungs of the immunized and control mice (n=4-5) were determined 4 days after lethal challenge. Supernatants of the lung homogenates were added onto MDCK cells and incubated for three days. The viral titers were measured by 50% endpoint dilution assay along with an HA assay.
Figure 4B:
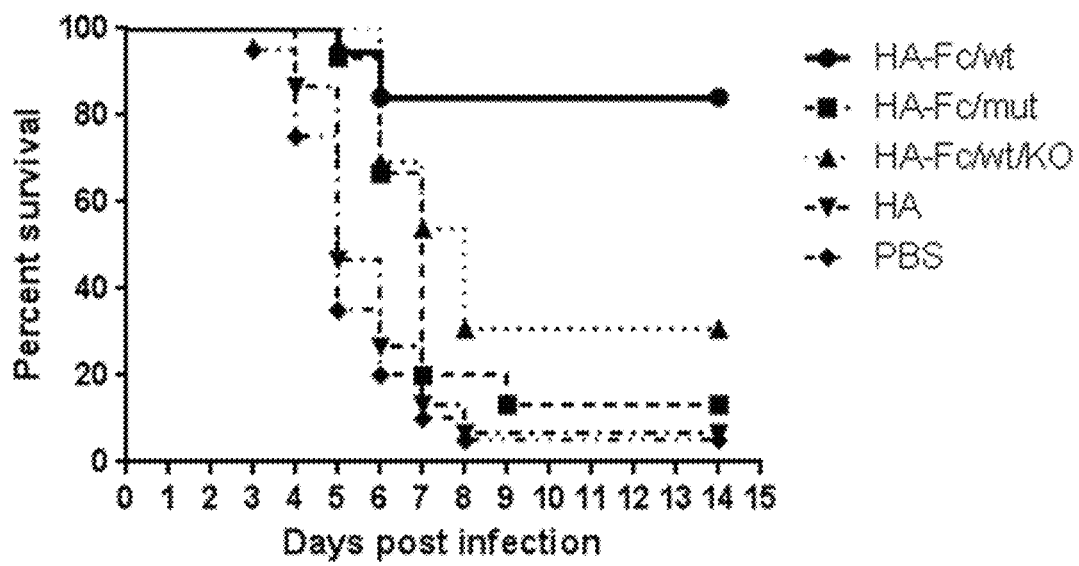
Figure 4C:
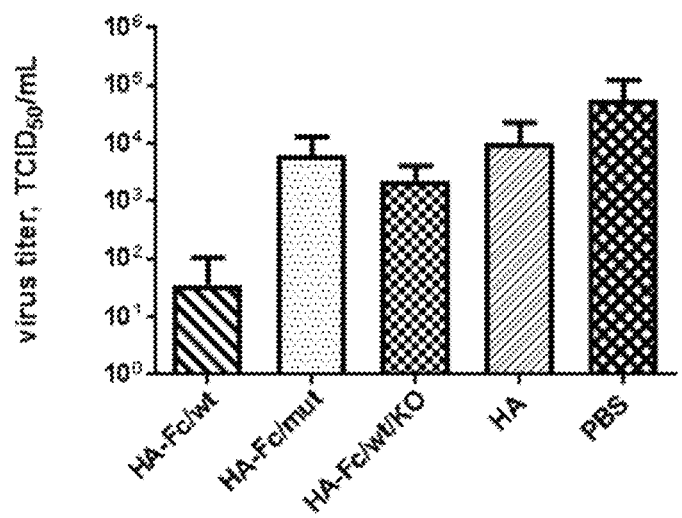
Figure 9:
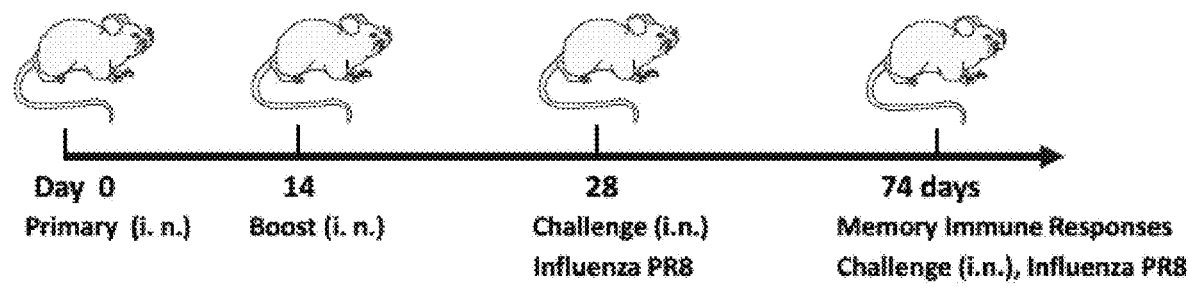
FIG. 9. Schematic description of mouse immunization and challenge. The 5 µg trimeric HA-Fc/wt, HA-Fc/mut, HA, or PBS in combination with 10 µg CpG were i.n. administered into wild-type (WT) or FcRn knockout (KO) mice for prime and boost immunizations at a 14-day interval. The mice were i.n. challenged with influenza PR8 virus as indicated.
Figures 10A, 10B, 10C:
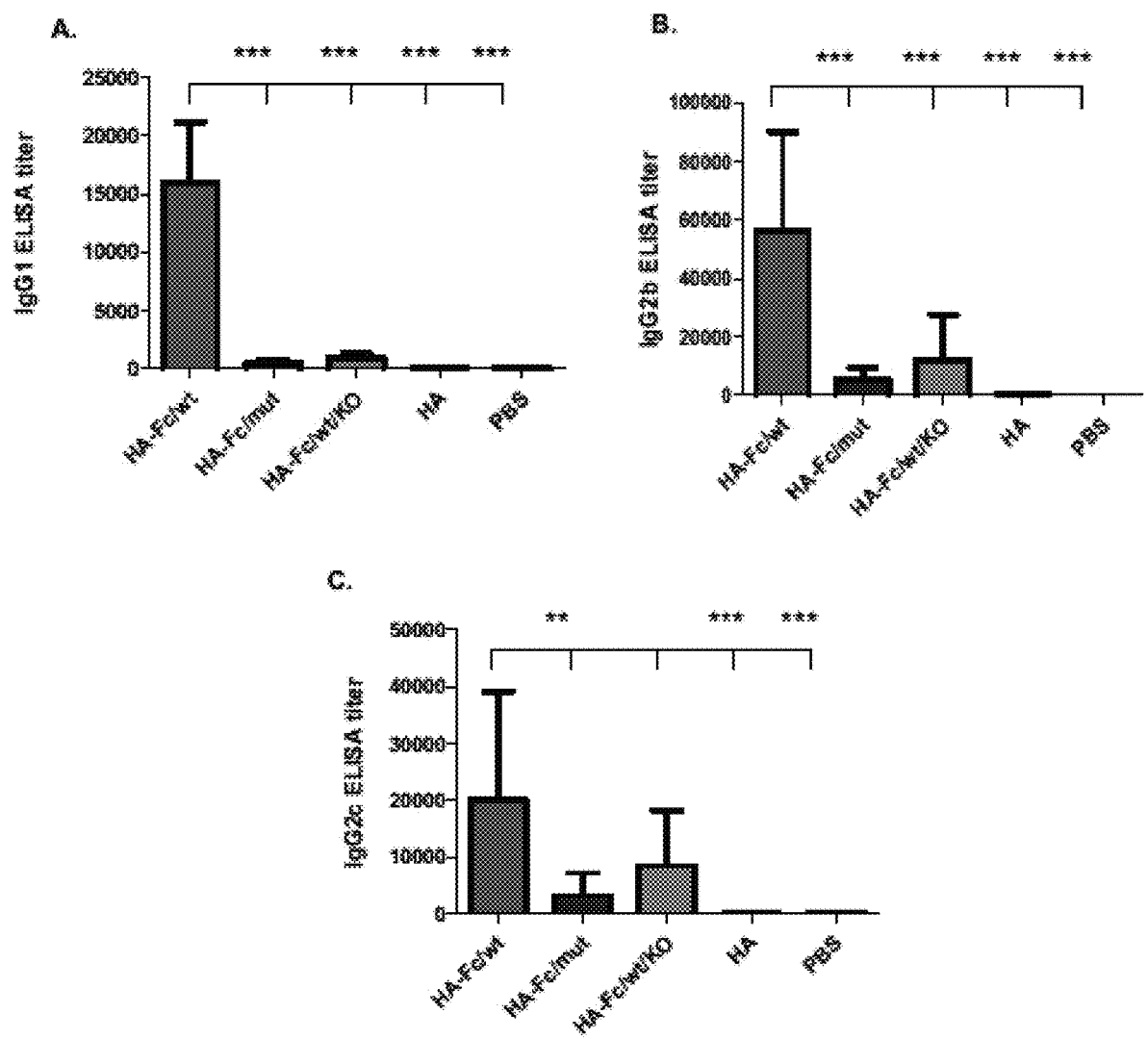
FIGS. 10A-C. Measurement of anti-influenza HA-specific IgG isotype antibody titers in serum. The 5 µg HA-Fc/wt, HA-Fc/mut, HA, or PBS in combination with 10 µg CpG were i.n. administered to wild-type (WT) or FcRn knockout (KO) mice for the prime and boost immunizations. Influenza HA-specific IgG antibodies were measured 14 days after boost by ELISA. IgG1 (A), IgG2b (B), and IgG2c (C) titers were measured in 10 representative mouse sera. The data represent mean titers S.E.M. Values marked with asterisk in the figures: , P<0.01, *, P<0.001. Immunization conditions are displayed on the bottom.
Figures 11A, 11B:
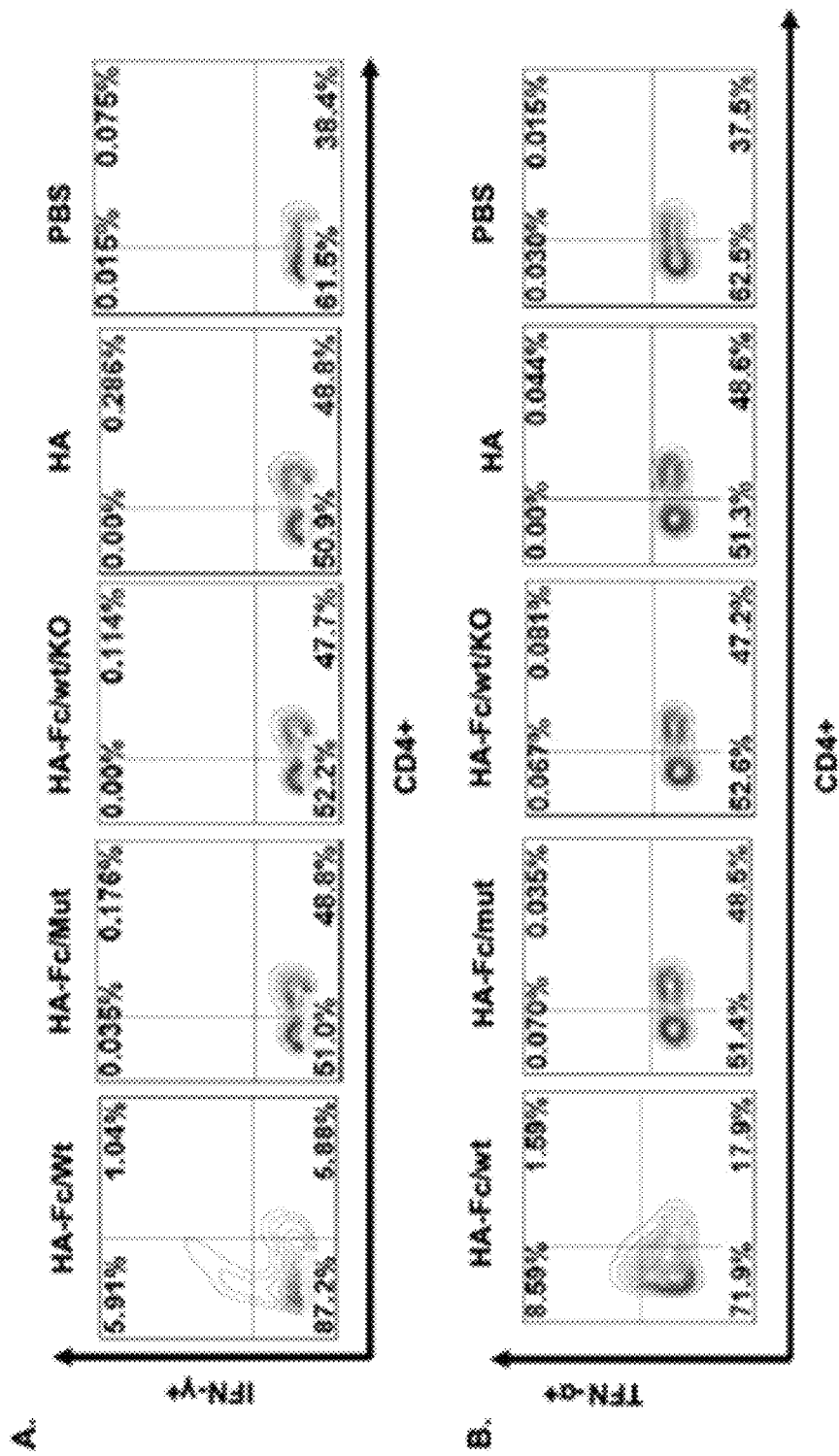
Figures 12A, 12B:
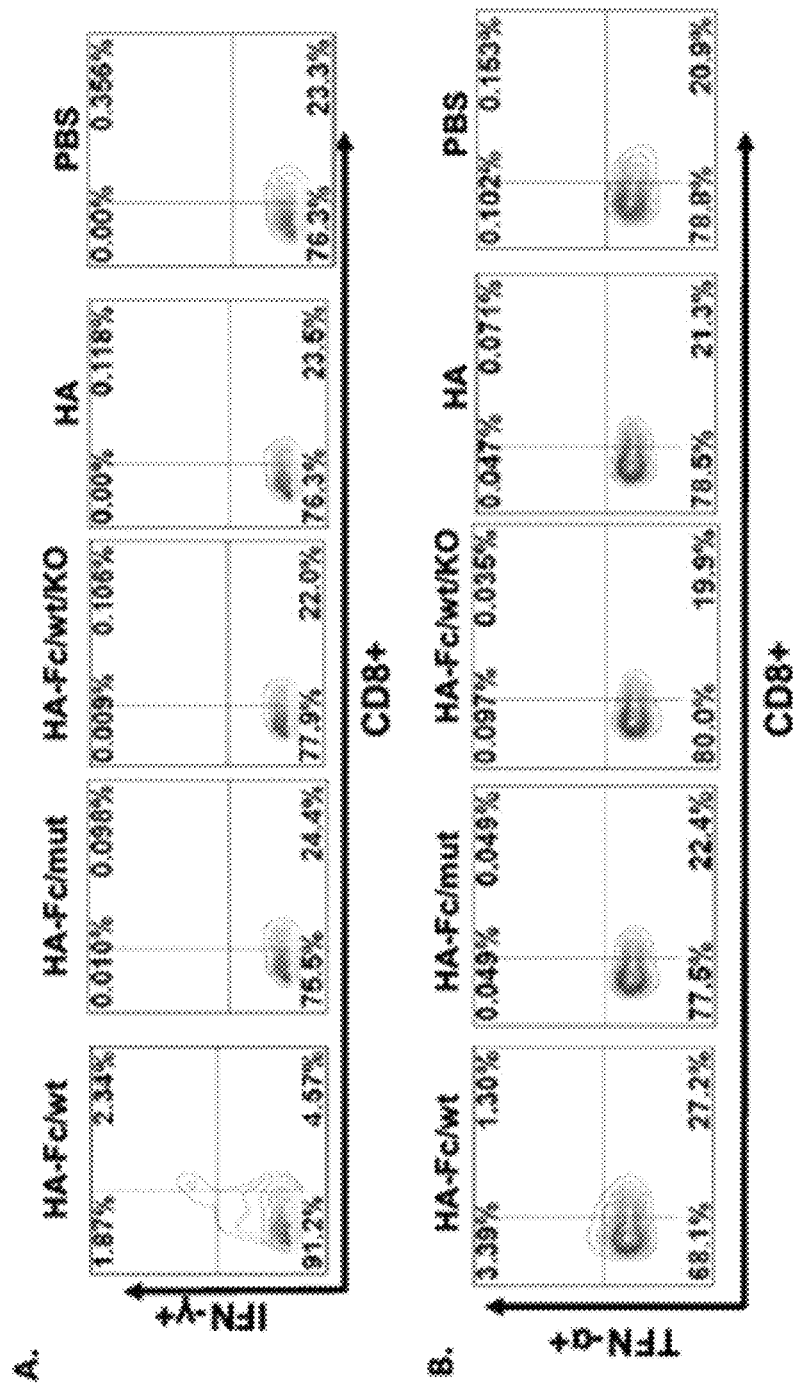
FIGS. 12A and 12B. The percentage of IFN-γ and TNF-α producing T cells in the lung 7 days after the boost. The lung lymphocytes from the immunized mice were stimulated for 10 hr with purified HA or medium control. Lymphocytes were gated by forward and side scatters and T cells labeled with anti-CD3 and identified by their respective surface markers CD4 and CD8 and intracellular IFN-γ or TNF-α staining. Numbers represent the percentage of IFN-γ+CD8+ (A), TNF-α+CD8+(B) T cells. Isotype controls included FITC-mouse-IgG1 with baseline response. Flow cytometry plots are representative of two independent experiments with 4 immunized mice pooled in each group. Numbers in the quadrants are the percentage of CD8+T lymphocytes.

We further determined if the HA portion of the HA-Fc maintains its trimeric conformation. First, the BS3, a hydrophilic, 11 ångström cross-linker that covalently links proteins, can stabilize trimeric influenza HAs (27, 28). Thus, the HA-Fc/wt or HA-Fc/mut proteins were cross-linked with BS3 and the treated proteins were subjected to SDS-PAGE analysis under a reducing and denaturing condition. As shown in FIG. 1E, the treated HA-Fc/wt and HA-Fc/mut proteins migrated to a position at an approximately 330 kDa in comparison with the untreated HA-Fc/wt protein that migrated at 110 kDa position, indicating the HA-Fc/wt protein exists as a trimer. Second, broadly neutralizing HA Abs were used to probe the epitopes on HA-Fc/wt. The HA-Fc/wt expressed either in CHO stable cell lines or the soluble form interacted with 6F12 and KB2 mAbs in an immunofluorescence staining (FIG. 1F) or with CR6261, FI6v3, and 6F12 mAbs in a concentration-dependent manner in ELISA (FIG. 1G). CR8020 mAb showed the binding with low affinity because it preferably binds to the HA stalk of Group 2 influenza virus. All these HA-specific mAbs are conformation-dependent (29-32). Together, it was shown that the HA portion of the HA-Fc proteins forms trimer and maintains the correct conformational structure, while its monomeric Fc portion retains its ability to interact with FcRn.

ii. FcRn-Mediated Intranasal Vaccination Significantly Enhances HA-Specific Immune Responses Whether FcRn-dependent transport augments the immunogenicity to HA protein was tested. Mice were immunized i.n. with 5 μg of HA-Fc, HA protein (equal molar amount), or PBS, all in combination with 10 μg CpG, and boosted after 2 weeks (FIG. 9). The specific engagement of FcRn in enhancing immunity was demonstrated in WT mice that were immunized with trimeric HA-Fc/mut proteins or FcRn knockout (KO) mice that are immunized with trimeric HA-Fc/wt proteins. The HA unlinked to an Fc fragment allowed the evaluation of FcRn-independent effects in vivo and determine the magnitude of any observed enhancement in immune responses conferred by targeting the HA-Fc to FcRn. Therefore, these control groups allow for the evaluation of the extent that interactions between FcRn and Fc contribute to the immune responses. CpG was co-administrated as a mucosal adjuvant (33). Significantly higher titers of total IgG, including individual isotypes, together with IgG1, IgG2b, and IgG2c (FIG. 10), were seen in the HA-Fc/wt immunized mice when compared with the HA, HA-Fc/mut, HA-Fc/wt/KO immunized and PBS-treated groups of mice (FIG. 2A). CpG was found to be necessary to enhance the Ab immune responses when the HA-Fc was targeted to FcRn. Moreover, sera from the HA-Fc/wt immunized mice exhibited strong neutralizing activity relative to other control groups (FIG. 2B). Likewise, HA-Fc/wt proteins induced strong IFN-γ- or TNF-α-producing CD8+ and CD4+ T cell responses, as evidenced by significantly higher percentages of IFN-γ or TNF-α-producing CD4+(FIGS. 2C & 2D and FIGS. 11A & 11B) and CD8+(FIGS. 2E & 2F and FIGS. 125A & 12B) T cells in response to HA stimulation in the lungs of WT mice immunized with HA-Fc/wt comparing to the other groups. This Th1 response was also supported by a major presence of the IgG2c subclass in the sera of the immunized mice (FIG. 10). It remains uncertain whether this polarized Th1 cell response is caused by mucosal immunization as a result of FcRn targeting or, more likely, by the CpG used in as adjuvant. Overall, the data demonstrate that engagement of FcRn greatly increased the efficiency by which HA antigen-specific Ab and cellular immune responses were induced.

iii. FcRn-Mediated Intranasal Vaccination Significantly Induced HA-Specific Local Immune Responses in the Respiratory Tract Because influenza virus initiates its infection in the airway (34), an important objective for FcRn-targeted mucosal delivery of influenza virus vaccines is to elicit stronger mucosal immune responses, including the presence of anti-viral IgA Ab in nasal washes and IgG in the lung. Several lines of evidence demonstrate the outcome. To determine the ability of the FcRn-targeted mucosal immunization to induce local humoral immune responses, HA-specific Abs were examined in mucosal secretions. The nasal wash and bronchoalveolar lavage fluids (BAL) were collected 14 days following the boost and analyzed for HA-specific IgG and IgA by ELISA. Significantly increased levels of HA-specific IgA and IgG were present in the nasal washes (FIG. 3A) and BAL (FIG. 3B) of the HA-Fc/wt protein immunized mice. WT, but not FcRn KO, mice that received the HA-Fc/wt protein had high levels of HA-specific IgA and IgG in the nasal washes and BAL (p<0.01, FIG. 3), indicating that the induction of mucosal IgA and IgG is FcRn-mediated. The formation and maintenance of germinal centers (GC) generally lead to the differentiation of memory B cells and long-lived plasma cells. Second, the activated GC reaction in the MedLN and spleens was monitored 10 days after the boost. As shown in FIG. 3C, the trimeric HA-Fc/wt immunization induced substantially higher levels of FAS+PNA+B220+ B cells in the MedLN or spleen of WT mice in comparison with those of the control groups. HA antigen targeting FcRn, combined with CpG, produced strong Ab and T cell immune responses in the respiratory mucosa.

iv. FcRn-Targeted Respiratory Vaccination Leads to an Increased Protection Against Lethal Influenza Challenge To test whether the humoral and cellular immune responses elicited by FcRn-targeted intranasal vaccination provide protection, all immunized mice were i.n. challenged with a lethal dose (5 MLD$_{50}$) of influenza PR8 virus 2 weeks following the boost. Mice were monitored and weighed daily for a 14-day period and were euthanized at 25% body weight loss as a study endpoint. Most of the mice in the control groups had severe weight loss (up to 25%) within eight days after the challenge (FIG. 4A) and either succumbed to infection or were euthanized. In contrast, only 3 of the 19 HA-Fc/wt-immunized mice experienced 25% body-weight loss. Hence, the trimeric HA-Fc/wt protein-immunized mice led to the protection in 84% mice, which was significantly higher than the survival rates of other control groups (FIG. 4B). In addition, each group was assessed for viral replication in the lungs 4 days after lethal challenge (FIG. 4C). Markedly lower levels of virus was observed in the lungs of the trimeric HA-Fc/wt-immunized mice. After the lethal challenge, there was 1.5 to 3 log reduction of virus titer in the HA-Fc/wt-immunized group when compared with the PBS group (FIG. 4C). Other control groups of mice also essentially failed to contain viral replication.

Figure 5A:
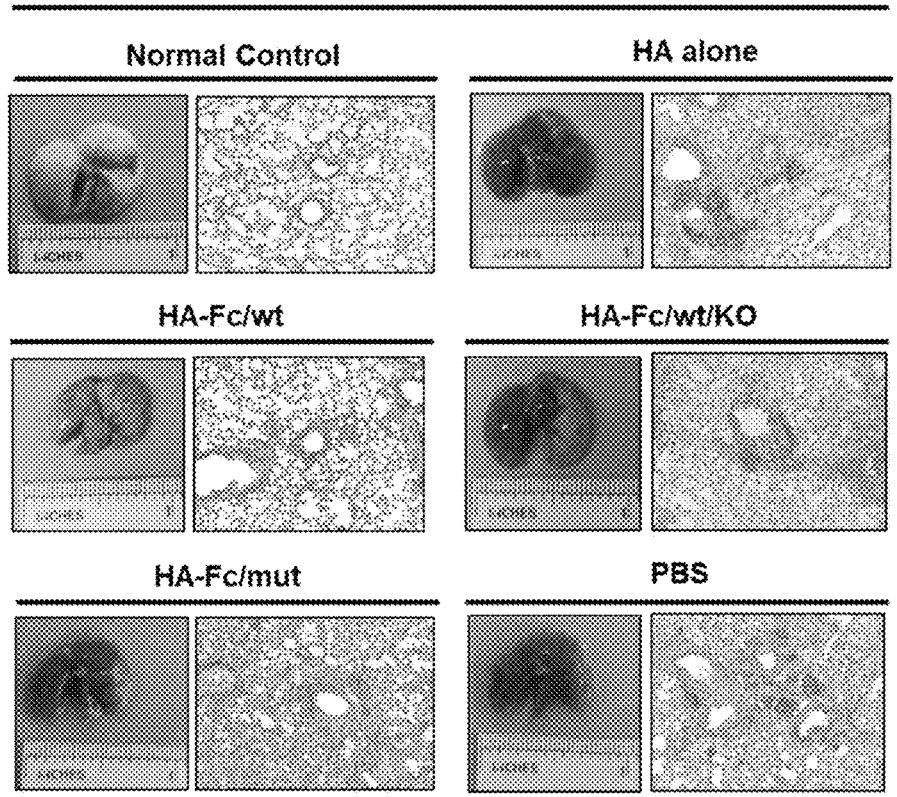
FIGS. 5A and 5B. (A). Gross- and histopathology of the lungs from the challenged mice. Lungs were collected from 6- to 14-day period post challenge based on 25% body-weight loss endpoint. The lungs from uninfected mouse were included as a normal control (n=3). The lung sections were stained with Hematoxylin-Eosin (H & E) to determine the level of inflammation in the lungs (10×). The representative slides were shown in the right. (B). The inflammatory responses for each lung section were scored. Statistical differences were determined by one-way ANOVA with Tukey's multiple comparison tests.
Figure 5B:
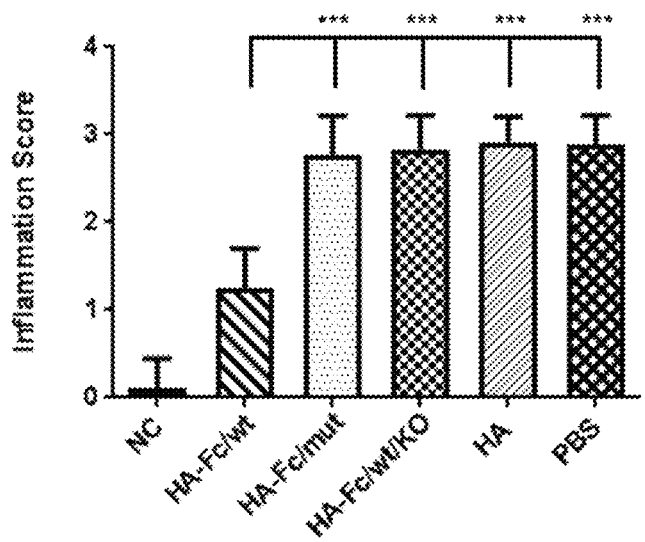
Figure 13:
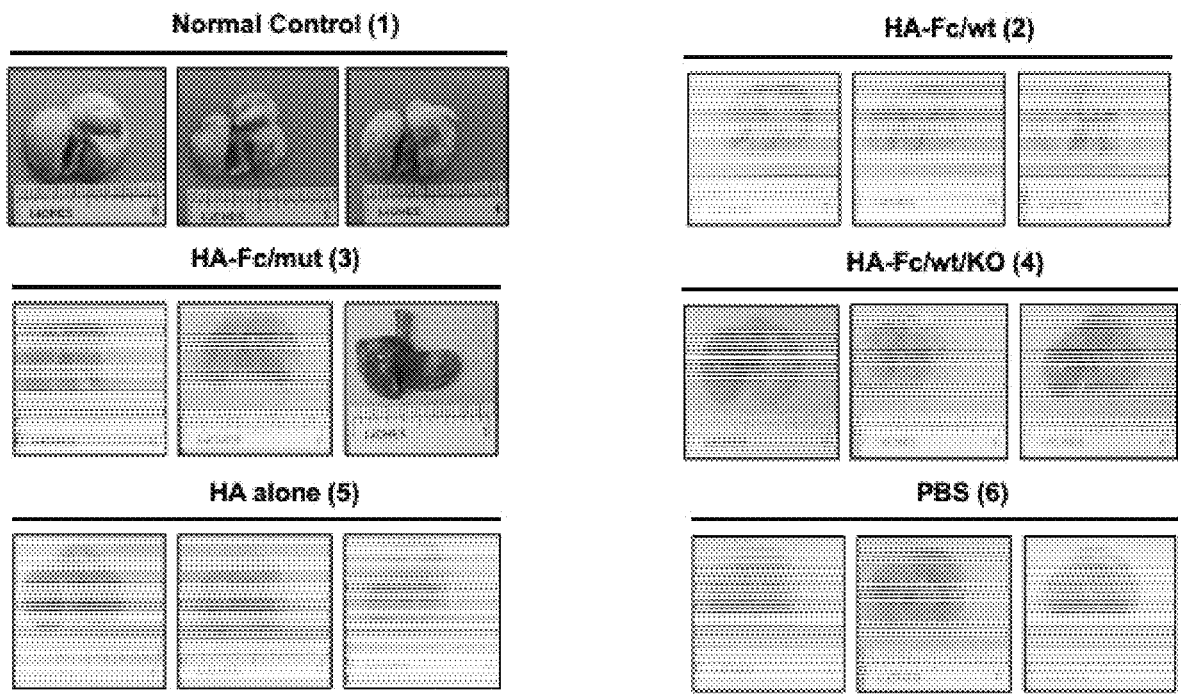
FIG. 13. Gross pathology of mouse lungs from the challenged mice. Lungs were collected from 6- to 14-day period post challenge based on 25% body-weight loss endpoint. The lungs from uninfected mouse included as a normal control (n=3).

To further demonstrate protection, the lung pathology of all groups of mice was characterized following challenge. Based on gross pathology, the lungs of mice in all control groups exhibited severe pulmonary lesions, as evidenced by hemorrhage with redness and edema (FIG. 5A and FIG. 13, images 3-6). However, the lungs of HA-Fc/wt-immunized mice displayed significantly reduced hemorrhage with an overall pink-like color (FIG. 5A and FIG. 13, image 2). The lungs of uninfected mice were used as a normal control (FIG. 5A and FIG. 13, image 1). To verify the gross pathology, histopathology was used to determine the extent of lung inflammation. In agreement with the gross pathology, the histopathology of mouse lungs of all challenged control groups showed remarkable infiltrations of monocytes and lymphocytes, resulting in high levels of inflammation (FIG. 5B). In contrast, the mice immunized with HA-Fc/wt had a significantly lower inflammation score of the lungs, compared to those of mice in the control groups (FIG. 5B). Collectively, these findings demonstrate that FcRn-mediated delivery of the trimeric HA-Fc/wt confers significant protection against lethal PR8 challenge, resulting in decreased mortality, viral replication and pulmonary inflammation. During the challenge, a significant difference in the sensitivity of PR8 infection between WT and FcRn KO mice was not found.

v. FcRn-Targeted Mucosal Vaccination Induces Higher Memory Immune Responses

Figures 6A, 6B, 6C, 6D:
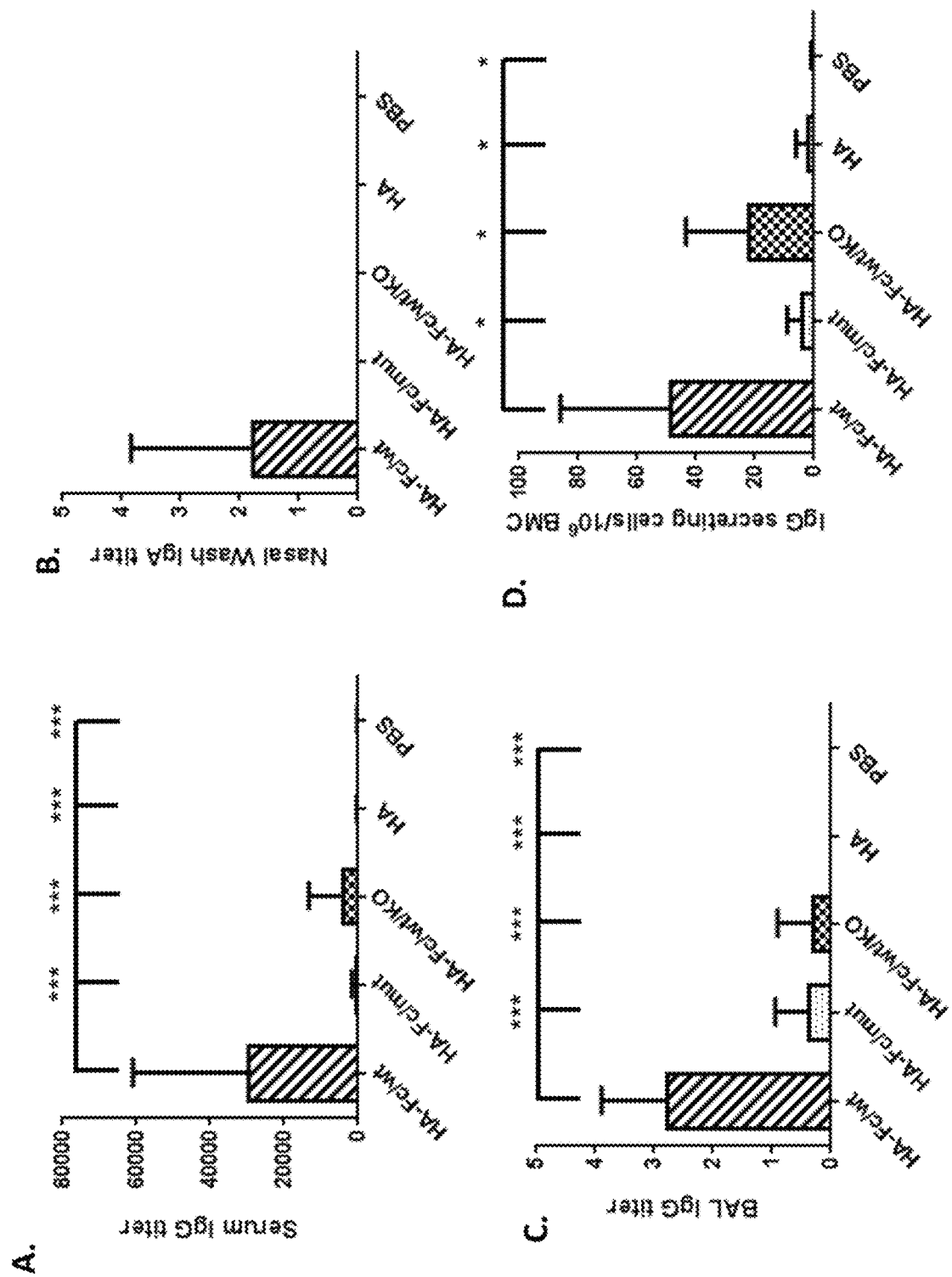
FIGS. 6A-F. Increased memory immune responses in FcRn-mediated respiratory immunization. (A) The duration of influenza-specific serum IgG response. Influenza HA-specific IgG was quantified by ELISA in serum by endpoint titer from 8-10 mice at 8 weeks after the boost. Influenza HA-specific IgG Ab was not detectable (ND) in PBS-immunized mice. (B & C). Measurement of anti-influenza HA-specific Ab titers in nasal washings (B, IgA), and BAL (C, IgG) after the boost immunization. Influenza HA-specific Abs were measured 8 weeks after boosting by ELISA. The Ab titer was measured in 5 representative mouse samples. The data represent mean values for each group (±S.E.M.). (D) Long-lived influenza HA-specific Ab-secreting cells in the bone marrow. Bone marrow cells (BMCs) removed 8 weeks after the boost was placed on HA-coated plates and quantified by ELIspot analysis of IgG-secreting plasma cells. Data were pooled from two separate experiments with 5 immunized mice pooled in each group. The graphs were plotted based on the average ELISPOT for four replicate wells for each experiment. Asterisk denotes statistics significant differences (P<0.05). (E+F). Induction of tissue-resident memory (TRM) T cells in mouse lungs. An additional group of mice that were i.m. immunized HA-Fc/wt was included as a parenteral route control. The CD3+CD4+CD69+CD11a+(E) or CD3+CD8+CD69+CD103+(F) TRM T cells in the lungs were assessed 8 weeks after the boost by FACS. Flow cytometry plots are representative of two independent experiments with 4 immunized mice pooled in each group. Numbers in the quadrants represent the percentage of TRM T lymphocytes.
Figure 14:
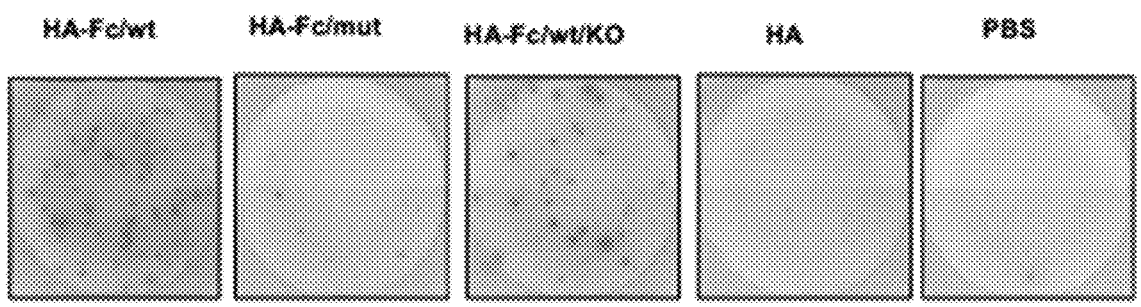
FIG. 14. Long-lived influenza HA-specific IgG antibody-secreting cells in the bone marrow. Bone marrow cells removed 8 weeks after the boost were placed on HA-coated plates and quantified by ELIspot analysis of IgG-secreting plasma cells. Data are representative of two separate experiments with five mice in each group.

In addition to providing an immediate protection against infection after boost, a successful influenza virus mucosal vaccine is expected to induce long-lasting immune memory. This study determined whether the FcRn-mediated respiratory vaccination with HA-Fc/wt promotes an effective memory immune response up to 8 weeks after the boost. As shown in FIG. 6A, higher titers of HA-specific serum IgG were detected in the mice immunized with the HA-Fc/wt. To further show that this group of mice also maintains local immune responses, the IgA Abs in nasal washings and IgG in the BAL were measured. Significantly high levels of HA-specific IgA and IgG were detected in the nasal washes (FIG. 6B) and BAL (FIG. 6C) in the HA-Fc/wt-immunized mice, but not in the mice of control groups. By ELISpot, a significantly higher number of HA-specific IgG-secreting plasma cells were detected in the bone marrow of mice immunized with HA-Fc/wt (FIG. 6D and FIG. 14). The existence of long-lived plasma cells in the bone marrow niche accounts for the maintenance of high levels of viral antigen-specific IgG in circulation (35). Because we detected some IgG secreting plasma cells in the immunized FcRn KO mice, we reason this may be caused by an individual mouse with positive immune responses because the samples were pooled. Also, there was no significant difference in the number of IgG secreting plasma cells between the mice immunized by HA-Fc/mut and FcRn KO mice immunized by HA-Fc/mut proteins (P>0.05). It remains to be determined whether HA-specific IgA-secreting plasma cells also develop. These data indicate that HA-specific B cells maintained significant memory immunity potential at least 2 months after the boost.

Figures 6E, 6F:
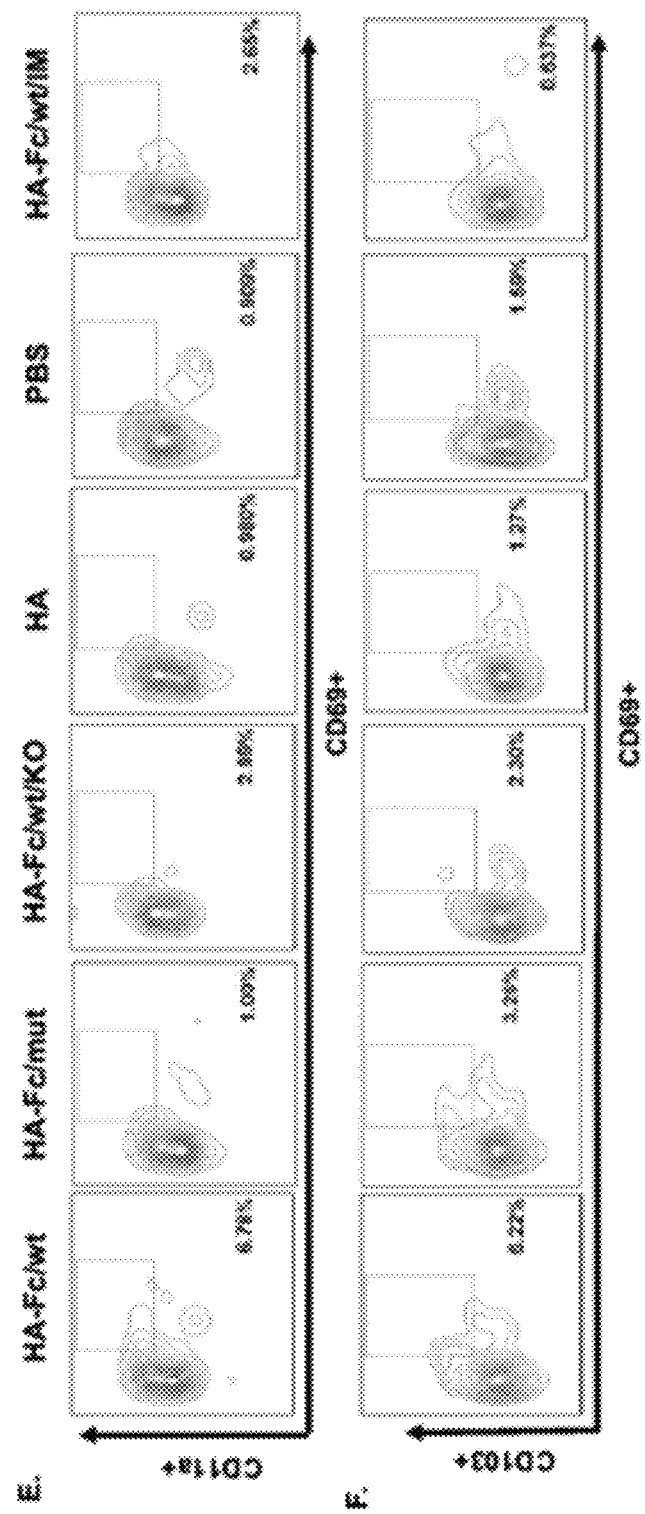
Figures 15A, 15B:
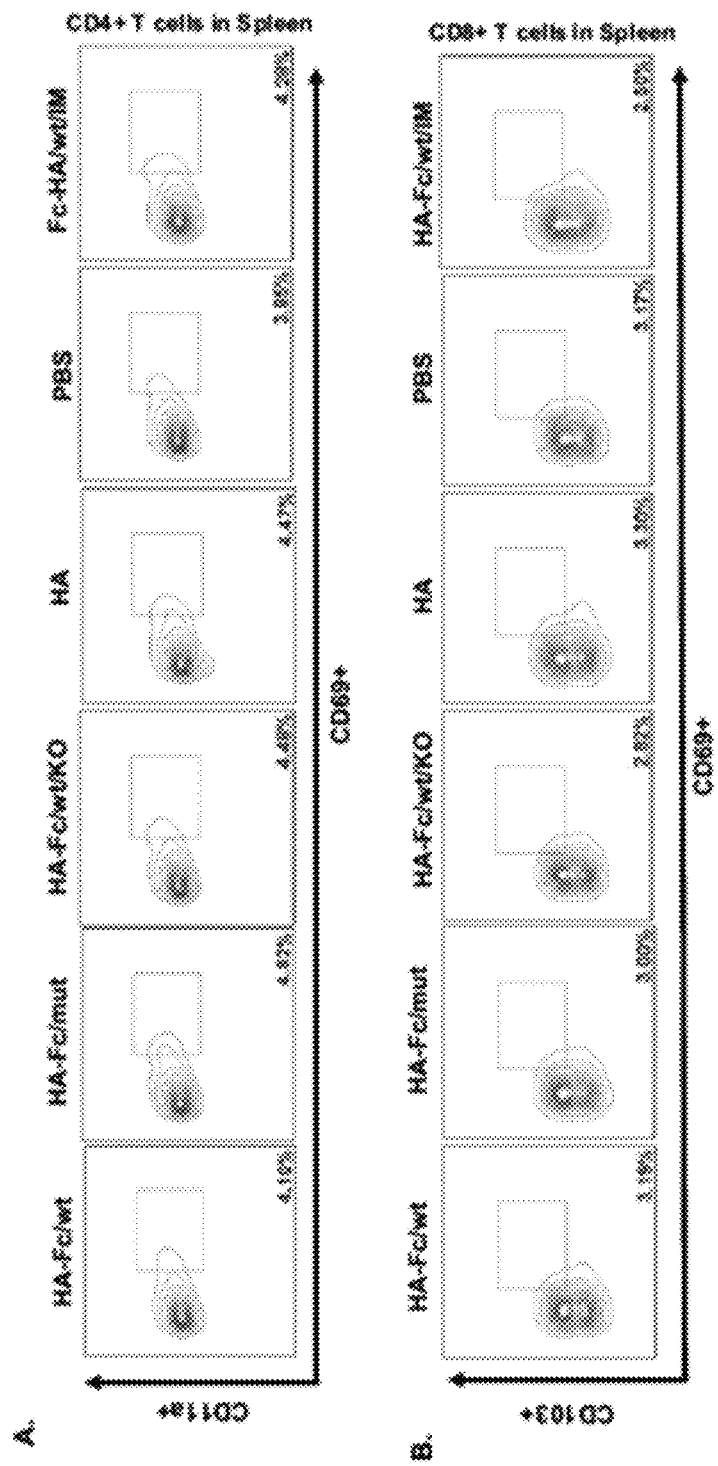
FIGS. 15A and 15B. The percentage of TRM T cells in the spleen. Spleen cells from the immunized mice were isolated 8 weeks after the boost. T lymphocytes were gated by forward and side scatters and T cells labeled with anti-CD3 and identified by their respective surface markers CD4 and CD8 and staining of TRM marker with either CD69+ CD11a+ or CD69+CD103+. Flow cytometry plots are representative of two independent experiments with 4 immunized mice in each group. Numbers in the quadrants represent the percentage of CD3+CD4+CD69+CD11a+(A) or CD3+CD8+CD69+CD103+(B) TRM T lymphocytes. Immunization conditions are displayed on the bottom.

Memory CD4+ and CD8+ T cells are essential to provide protection against influenza virus (6, 36). A recently appreciated subset are TRM T cells, a subset of T cells that are non-circulating and remain in the lung to provide a rapid response against influenza infections (37, 38). Hence, it was determined whether FcRn-mediated immunization could induce TRM T cells in the lung. In order to differentiate circulating T cells from lung TRM T cells, the method of an intravenous (i.v.) in vivo infusion of fluorescently-labeled anti-CD3 Ab which targets T cells in circulation was used, but not CD4+ TRM (CD69+CD11a+) or CD8+TRM (CD69+CD103+) T cells within the lung (37, 38). Substantial numbers of CD4+CD69+CD11a+ TRM cells (FIG. 6E) and CD8+CD69+CD103+ TRM cells (FIG. 6F) were detected in the lungs, but not in the spleen of HA-Fc/wt-immunized mice (FIG. 15), in comparison with that of mice in the control groups. There was no detection of an appreciable increase in CD4+ or CD8+ TRM T cells in the lungs of all experimental animals when mice were immunized by the intramuscular (i.m.) route (FIGS. 6E & 6F). Together, these data indicate that FcRn-targeted respiratory, but not parenteral, immunization can induce lung-resident memory CD4+ and CD8+ T cells.

Figures 7A, 7B:
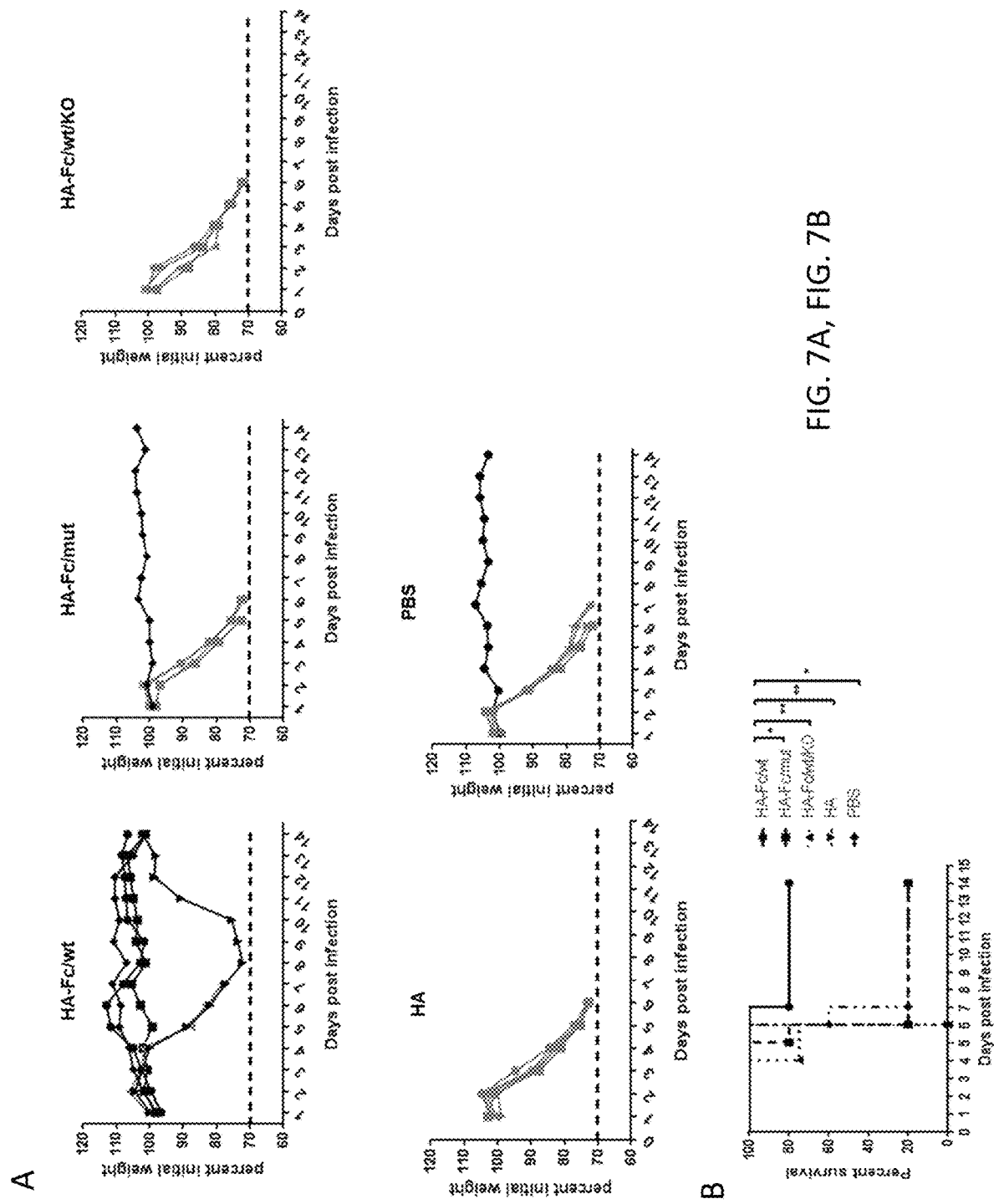
FIGS. 7A-C. (A). Body-weight changes following influenza virus challenge. Two weeks after the boost, groups of five mice were i.n. challenged with PR8 virus (5 MLD50) and weighed daily for 14 days. Mice were deceased or humanely euthanized if more than 30% of initial body weight was lost. (B). Mean survival following influenza virus challenge in mice 8 weeks following the boost. The immunized mice were i.n. challenged with 5 MLD50 of PR8 virus and weighed daily for 14 days. Mice were deceased or humanely euthanized if more than 25-30% of initial body weight was lost. Percentage of mice protected on the indicated days is calculated as the number of mice survived divided by the number of mice in each group (n=5), as shown by Kaplan-Meier survival curve. Statistical differences were determined using multiple Mantel-Cox tests. (C). Proposed model of FcRn-mediated respiratory immunization. The Fc-fused HA antigens are transported by FcRn and targeted to the antigen presenting cells (APCs), such as dendritic cells. The antigen is taken up by pinocytosis or FcγRI-mediated endocytosis in APCs, then processed and presented to T cells in the lung or draining lymph nodes.

Last, to test if these memory immune responses could provide protection, the immunized mice were again challenged with i.n. PR8 strain two and half months after boost. Mice were weighed daily for a 14-day period and were euthanized at 30% body weight loss as a study endpoint. Most of the mice in the control groups had severe weight loss within 6-7 days after the challenge (FIG. 7A), and either succumbed to infection or were euthanized. Upon lethal challenge, mice immunized with the HA-Fc/wt exhibited significantly reduced disease severity with a survival rate of 80% (FIG. 7B), while mice in control groups succumbed to rapid weight loss and death. Overall, FcRn targeted mucosal delivery of influenza HA vaccine engendered an effective memory immune response and provided protection against challenge.

2. Discussion

Respiratory tract infections are important causes of serious illnesses and death. Conventional vaccination with non-replicative vaccines is primarily administered by the parenteral routes. However, successful vaccination against respiratory infections may require high levels of potent and durable humoral and cellular responses in the local respiratory tract that are best achieved by direct, mucosal immunization. To achieve this goal, a strategy to deliver vaccine antigens via the respiratory route is needed to improve the protective efficacy against respiratory infections. Described throughout is a strategy for vaccine delivery based on exploiting the FcRn-mediated Ab transfer pathway to deliver an influenza virus HA-Fc fusion protein vaccine across the respiratory epithelial barrier.

By using an intranasal delivery route that has been already approved for human use, the present study demonstrate that FcRn-targeted respiratory vaccination induced substantial local and systemic immunity against lethal influenza virus infection. Site-specific (lungs)-targeted delivery provided a unique opportunity to improve the efficiency of influenza virus vaccination. This conclusion is supported by several lines of evidence. First, the HA-Fc/wt immunized mice have produced significantly high levels of IgG in the blood. Second, the HA-Fc/wt-immunized mice exhibited strong neutralizing Ab activity relative to control groups. Third, the majority of HA-Fc/wt-immunized mice resisted lethal influenza virus infection with reduced virus replication and inflammation in the lung. In contrast, most mice immunized by HA-Fc/mut or HA alone exhibited poorer immune responses, increased levels of pulmonary inflammation, and decreased protection against virus challenge. The data point to the FcRn pathway as key to the enhanced protection against respiratory virus challenge and demonstrate the value of our trimeric fusion protein strategy for directing viral antigens to this pathway. Several mechanisms may account for the protection against respiratory infection by FcRn-targeted mucosal vaccination. Efficient delivery of HA-Fc proteins across the respiratory barrier may increase the half-life of HA-Fc (21) to allow for enhanced FcγR-mediated uptake of HA-Fc by antigen-presenting cells such as dendritic cells (39-41). Previous studies showed that HA alone by i.n. route elicited some protective immunity following intranasal immunization (42); in our hand, HA alone was very poorly immunogenic and produced minimal protection against virus challenge. Previous work showed CpG does not increase the permeability of airway respiratory barrier; in contrast, it enhances tight junction integrity of the bronchial epithelial cell barrier (43). Other agents are avoided including volatile chemical anesthetics that are known to increase epithelial barrier permeability. Hence, the results clearly point to the benefits of FcRn-mediated delivery for maximizing the efficacy of respiratory tract-administered influenza virus HA vaccines.

Considering influenza virus infects the epithelial cells lining the respiratory tract, a protective vaccine should induce immunity in the mucosa that effectively hinders virus penetration and spread. The local humoral immune response can be characterized by secretion of IgA in the upper respiratory tract or IgG in the BAL, and the presence of activated germinal centers (GCs) in the draining lymph node, and the cytokine secretion by lung-specific T cells (1, 4). First, the trimeric HA-Fc/wt-immunized mice have produced high levels of IgG and IgA Abs in the BAL and nasal secretions. IgA is a major protective Ab in mouse nasal secretions after immunization with influenza (34, 44). Local secretory Abs represent a primary barrier of immune defense against viral infections of the respiratory tract. Second, the HA-Fc/wt induced a high frequency of IFN-γ or TNF-α-producing CD4+ and CD8+ T cells in the lung tissues of the immunized mice. IFN-γ and TNF-α are clearly indispensable for resistance to influenza infections (45). Third, the presence of activated GCs was detected in the MedLNs draining the lung. The nasopharynx-associated lymphoid tissue (NALT) and the MedLNs are usually the sites where respiratory immune responses are initiated against antigens administered intranasally, after reaching the lung. The presence of activated GCs in the NALT merits further investigation. Hence, FcRn-mediated respiratory delivery of influenza virus vaccine antigens promotes potent antiviral humoral and cell-mediated immune responses at the primary site of influenza infection, which is critical for clearance of the virus.

Induction of influenza-specific memory responses is crucial for a vaccine to provide protection after re-exposure to influenza virus (6, 36, 46). Immunological memory has been a concern in protein-based subunit mucosal vaccine development. To establish long-lasting protection, a multifaceted memory immune response is essential, including virus-specific memory T and B cells and long-lasting plasma cells. A remarkable feature of this study is that FcRn-mediated mucosal vaccination with HA-Fc/wt induced and sustained higher levels of HA-specific Abs, both IgA and IgG, and plasma cells 2 months after the boost. More importantly, we detected a higher percentage of CD4+ or CD8+ TRM T cells in the lungs of mice immunized with HA-Fc/wt, but not in control groups. CD4+ T cells are essential for promoting memory CD8+ T cell responses, including TRM CD8+ T cells (6, 47). TRM CD4+ or CD8+ T cells in the lung have been shown to promote rapid viral clearance at the site of infection and mediate survival against lethal influenza challenge (47, 48). In addition, it was shown that TRM T cells are induced only via intranasal immunization and not by intramuscular injections. This result is consistent with other findings that TRM T cells appear in the lung after natural influenza infection (38, 49) or they are induced by intranasal vaccination with live attenuated influenza virus in a mouse model (37). The results from FcRn-mediated respiratory delivery of influenza virus HA antigens verifies that the lung-resident T cells can only be induced solely via respiratory vaccination. Corresponding to the induction of memory humoral and cellular immune responses, most HA-Fc/wt-immunized mice resisted lethal influenza infection 2 months after boost.

The Fc-fused trimeric HA proteins are required to induce the high level of protection from influenza virus infection. Mice were immunized with an Fc-fused monomeric HA protein that mimics IgG structure (FIG. 16). Although the monomeric HA-Fc/wt induced a strong IgG immune response (FIG. 18), it only conferred partial protection to subsequent influenza challenge (FIG. 19 & FIG. 20). This low protection conferred by the monomeric HA vaccine may be interpreted by the fact that the native viral HA exhibits a trimeric presentation, which is essential for inducing conformation-dependent neutralizing Abs that mirror those induced by exposure to natural infection. Hence, a trimeric HA-Fc was designed and produced that mimics the native HA structure, as evidenced by the recognition of the trimeric HA-Fc by conformation-dependent anti-HA Abs and its ability to bind to FcRn. As expected, the mice immunized by the trimeric HA-Fc/wt proteins had high levels of survival and decreased morbidity in HA-Fc/wt vaccinated mice.

Figures 16A, 16B, 16C, 16D, 16E:
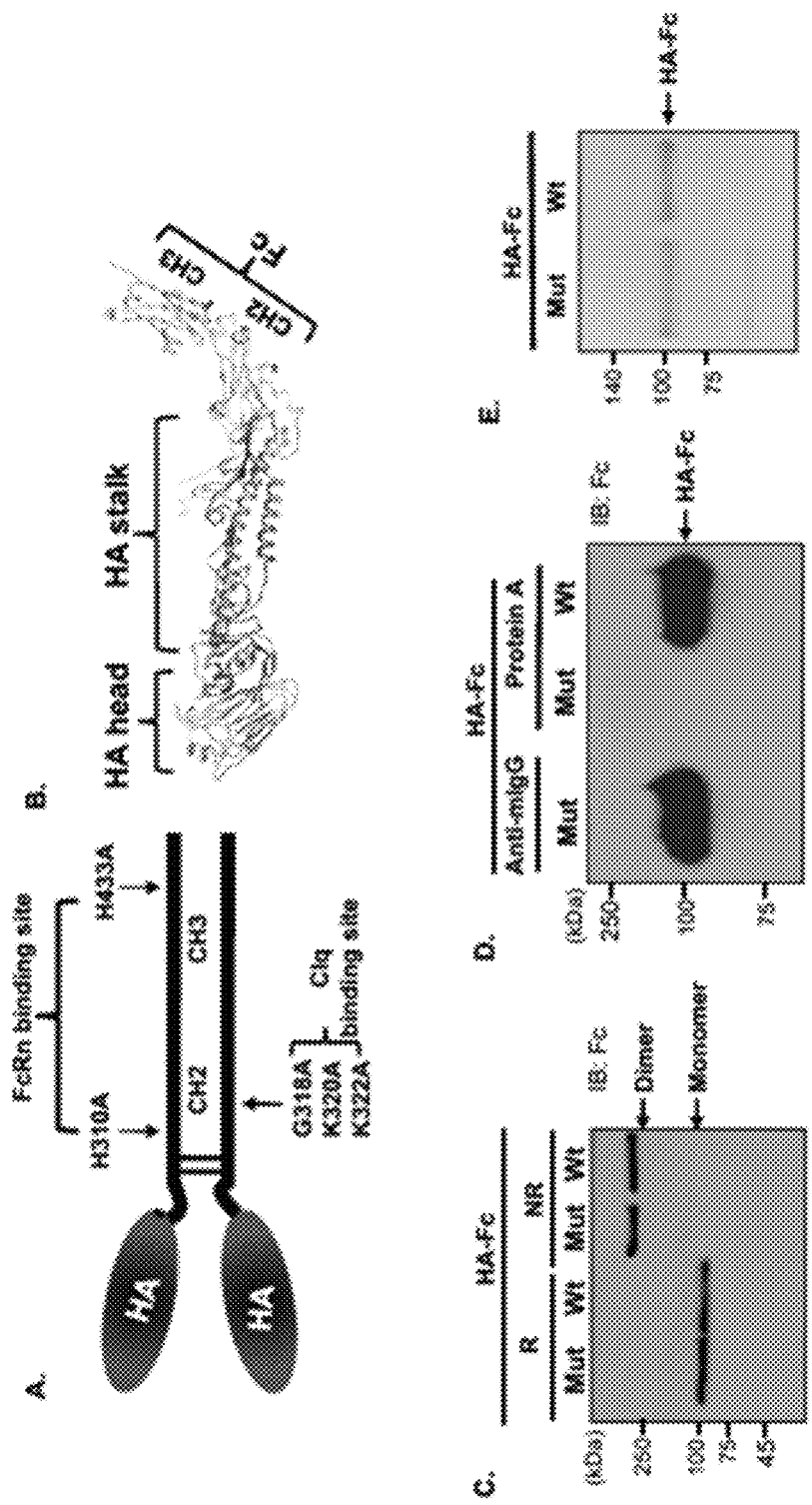
FIGS. 16A-E. Design and characterization of influenza HA fused to IgG Fc fragment. (A). Schematic illustration for the genetic fusion of influenza PR8 HA and murine FcΔ2a cDNA to create a HA-Fc fusion gene that mimics an IgG structure. Mutations were made in the CH2 domain of FcΔ2a fragment by using site-directed mutagenesis to replace Glu318, Lys320, and Lys322 with Ala residues to remove the complement C1 q binding site, and His 310 and His 433 with Ala residues to eliminate FcRn binding sites. (B.) Predicted protein structure of HA-Fc. The structural image was generated based on the nucleotide sequences and modeled through Phyre2 and Chimera. (C). The HA-Fc fusion proteins were secreted by CHO cells. The HA-Fc proteins were subjected to SDS-PAGE gel electrophoresis and Western blot analysis. The HA-Fc proteins were recognized by either goat anti-mouse IgG. The fusion protein appeared as a dimer under non-reducing (NR) or a monomer under reducing (R) conditions. (D). The HA-Fc proteins interact with Protein A. The HA-Fc/wt or HA-Fc/mut protein was incubated with Protein A resin slurry or anti-mouse IgG conjugated Agarose beads for 2 hr at 4° C. Samples were eluted and subjected to SDS-PAGE gel electrophoresis and Western blot analysis with anti-Fc Ab. (E). The HA-Fc/wt and HA-Fc/mut proteins were purified by affinity chromatography and stained with Coomassie blue.

To target the HA to FcRn, we first generated the fusion protein, HA-Fc/wt, by mimicking an IgG structure and cloning the extracellular domain of influenza PR8 HA in frame with a modified mouse IgG2a Fc fragment (FIG. 16A). To create this, the extracellular portion of PR8 HA was amplified by PCR using the primer pair (5'-GCCGAAGCTTGCCACCAT GAAGGCAAACC-TACTGGTCCTGTTAAG-3' (SEQ ID NO:12), 5'-AG-ATCCCGAGCCACCTCCTCCGGACCCAC CCCCGCCTGATCCCTGATAGATCCCCATTGATTCC-3' (SEQ ID NO:13)). The hinge, CH2 and CH3 domains of mouse IgG2a were amplified by PCR using the primer pair (5'-GGATCAGGCGGGGGTGGG TCCGGAG-GAGGTGGCTCGGGATCTGAGCCCAGAGGGCC-CACAATCAAGC-3' (SEQ ID NO:14), 5'-GCCGTCTA-GATTATTTACCCGGAGTCCGGGAGAAGCTC-3' (SEQ ID NO:15)). The HA antisense primer and the Fc sense primer contain complementary glycine (G) and serine (S) codons to produce a 14GS linker to bridge the HA and IgG Fc fragments. A similarly modified HA-Fc/mut fusion protein was generated that is unable to bind FcRn owing to histidine to alanine residue substitutions at positions 310 and 433 (Kim et al, 1995). In both cases, the complement C1q-binding motif was eliminated to abrogate C1q binding (Duncan et al., 1988) (FIG. 16A). All of the resultant plasmids were confirmed by double-stranded DNA sequencing to verify error-free PCR amplification and DNA cloning. To produce proteins, CHO cells were transfected by plasmids to establish stable cell lines by G418 selection. Cell clones secreting the high level of the HA-Fc/wt or HA-Fc/mut proteins were selected.

Figures 17A, 17B:
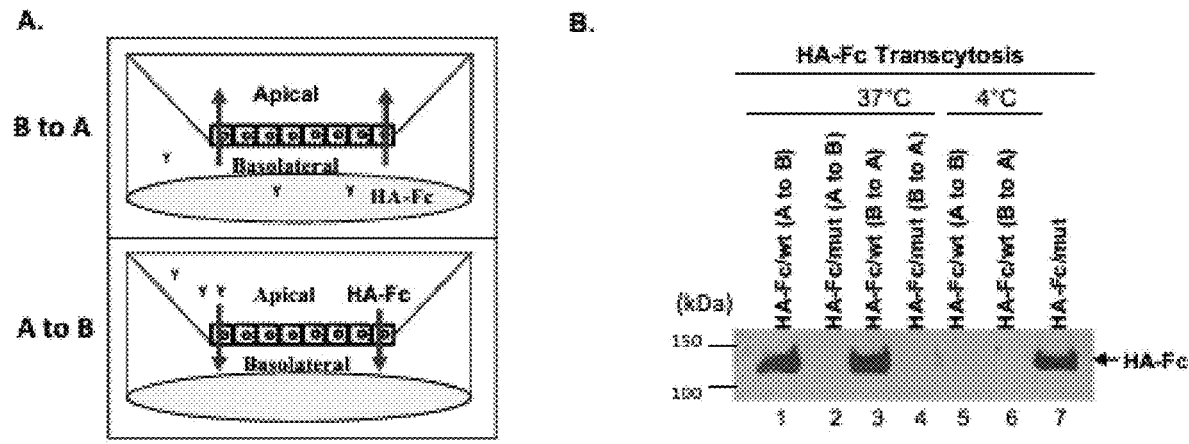
FIGS. 17A and 17B. Transcytosis of the HA-Fc proteins across MDCK cells expressing rat FcRn and β2m. Transport of HA-Fc/wt fusion proteins in rat MDCK-FcRn cell lines. MDCK-rFcRn cells were plated onto 24-mm transwells and grown for 3-6 days to allow a polarized monolayer with resistance greater than 300 Ωcm2 to form. The purified HA-Fc/wt or HA-Fc/mut (50 µg/ml) was applied to the apical (A) or basolateral (B) reservoir and allowed for transport for 2 hr. The proteins were collected from the basolateral (B) or apical (A) reservoir and blotted with anti-HA antibody under reducing condition. The HA-Fc/wt fusion protein (lanes 1& 3), but not the HA-Fc/mut, fusion proteins were transported across MDCK-rFcRn cells in both directions. The HA-Fc/wt transport was inhibited at 4° C.

The HA-Fc fusion proteins were further characterized. Using a SDS-PAGE-Western blot analysis, the HA-Fc proteins were recognized by an Fc-specific antibody. The fusion proteins appeared as Fc dimers in non-reducing conditions, and as a monomer under reducing conditions (FIG. 16C). It was determined if the HA-Fc proteins interact with Protein A, which shares the same IgG Fc binding site with FcRn. After incubation with Protein A-agarose beads, we found the Protein A beads were able to pull down the HA-Fc/wt protein, but not the HA-Fc/mut proteins (FIG. 16D). As expected, the HA-Fc/mut was pulled down by anti-mouse IgG-conjugated beads (FIG. 16D, lane 1). The HA-Fc/dimer/wt and HA-Fc/mut fusion proteins were purified from cell culture supernatants by affinity chromatography using Protein A-conjugated beads or anti-mouse IgG-conjugated beads, respectively (FIG. 16E). To ascertain whether the HA-Fc/wt but not the HA-Fc/mut fusion proteins were transported by FcRn, a transcytosis assay was performed (Bai et al., 2011). MDCK cells expressing rat FcRn were obtained from Dr. Pamela Bjorkman (California Institute of Technology) (Tesar et al., 2006). FcRn-dependent transcytosis of intact HA-Fc/wt, but not HA-Fc/mut, was detected in MDCK cells expressing rat FcRn and β2m (FIG. 17). These results showed that efficient delivery of HA-Fc/wt across the epithelial barrier was dependent on the Fc moiety and its ability to interact with FcRn.

To examine the immune responses elicited by FcRn-targeted mucosal vaccination, groups of mice were intranasally (i.n.) immunized with 5 μg HA-Fc proteins and boosted two weeks later in the presence of 10 μg CpG adjuvant. Wild-type mice were immunized with the HA-Fc/wt (n=39), HA-Fc/mut (n=10), HA (n=10), or PBS (n=40), while FcRn-KO mice (n=14) were immunized with the HA-Fc/wt proteins. The use of HA-Fc/mut, HA protein, or FcRn KO mice served as important controls for determining FcRn-mediated induction of immunity and protection. WT mice-immunized with 5 μg HA-Fc/dimer/wt induced significantly higher titers of HA-specific antibody compared to that of other groups (FIG. 18). The HA protein alone-immunized mice induced a negligible amount of HA-specific antibody.

To evaluate whether the immune responses induced by the HA-Fc/wt proteins can protect mice from influenza infection, all groups of mice were i.n. challenged with PR8 virus and weighed daily for 14 days (FIG. 19). 45% mice immunized by the HA-Fc/wt were protected in comparison with higher rates of morbidity of the control groups, where 90% wild-type mice or 64% FcRn KO mice immunized by the HA-Fc/mut or the HA-Fc/wt, respectively, 100% mice immunized by the HA alone, and 82% mice mock-immunized by PBS succumbed to infection (FIG. 20). FcRn-mediated mucosal delivery of monomeric HA-Fc/wt proteins provided a partial protection from the challenge.

The effects of FcRn-targeted mucosal immunization differ considerably between WT and FcRn KO mice or the HA-Fc/wt and the HA-Fc/mut-immunized mice in terms of mucosal and systemic immune responses, cytokine expression profiles, the maintenance of T and B cell memory and long-lived bone marrow plasma cells, and resistance to infection. In this study, it was shown that FcRn-targeted mucosal delivery of influenza virus HA vaccine can provide protection against homologous influenza virus. This pathway can be used to deliver a universal influenza vaccine which protects against all strains of influenza virus, eliminating the need for seasonal vaccination with a potential to protect against pandemic strains. An optimal universal influenza vaccine is expected to induce broadly neutralizing Abs and cross-reactive T cells against conserved and protective influenza virus antigens, including the stalk domain of HA, nucleoprotein (NP), the ectodomain of matrix 2 (M2e), and/or neuraminidase (NA) (50). The development of a universal influenza virus vaccine using the FcRn-mediated mucosal delivery of highly conserved influenza virus antigens, such as chimeric HA (51-53) or HA stalk-based vaccine (31, 54), is very likely. First, the trimeric HA-Fc antigen is readily recognized by several conformation-dependent, stalk-specific Abs (CR6121, FI6v3, 6F12, and CR8020) in a concentration-dependent manner (FIG. 1H) (29-32). Second, FcRn-mediated influenza HA delivery induces memory immune responses, including TRM T cells. TRM T cells are shown to promote viral clearance and mediate heterosubtypic protection and survival against lethal influenza virus challenge (37, 55). Third, FcRn-mediated mucosal delivery of influenza virus vaccines aimed at stimulating protective immunity in the respiratory tract will make prospective universal influenza virus vaccines more effective and efficient. This mucosal response may forestall influenza virus infection in its early stages, thereby contributing significantly to the reduction in influenza clinical infection and spread in the community. Fourth, influenza virus infection causes severe diseases by the virus itself followed by secondary bacterial infections in the young and the elderly. Effective vaccines in the high-risk populations are essential to prevent severe disease and to reduce virus transmission.

Figure 7C:
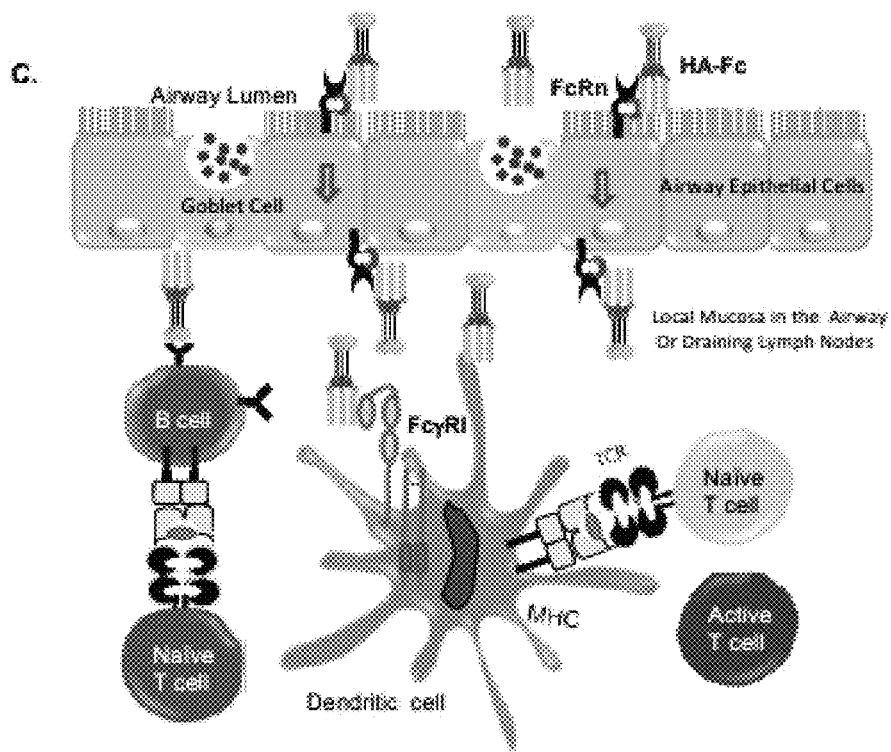

Taken together, this study has demonstrated the important role of FcRn in facilitating intranasal delivery of protective influenza virus vaccine antigens across the respiratory mucosa, highlighting a novel approach for formulating influenza virus vaccines that stimulate long-lasting, protective local and systemic immunities. We propose a model for FcRn-targeted respiratory immunization (FIG. 7C). In general, mucosal DCs take up FcRn-transported antigens and subsequently migrate to MedLNs where they prime CD4+ T cells and initiate the cognate B cell response in the GCs. By increasing the persistence of HA-Fc in tissue and circulation, interactions with FcRn may further enhance the development of long-term humoral and cellular immunity by sustaining high levels of serum IgG Abs and TRM T cells specific for HA. It is expected that FcRn can increase pre-existing influenza immunity because FcRn can transport influenza antigen-Ab complexes across the mucosal barrier (14). The results imply that FcRn-mediated respiratory immunization could be proven to be an effective and safe strategy for maximizing the efficacy of vaccinations directed against influenza virus infections. The goal is to develop multivalent mucosal vaccines offering protection against a spectrum of respiratory infections.

3. Materials and Methods i. Cells, Abs, and Virus.

Chinese hamster ovary (CHO) cells were purchased from the American Tissue Culture Collection (ATCC). MDCK cells were maintained in Opti-MEM complete medium (Invitrogen Life Technologies) and CHO cells were maintained in complete Dulbecco's Minimal Essential Medium (DMEM) (Invitrogen Life Technologies), both supplemented with 10% fetal bovine serum (FBS), 2 mM L-glutamine, nonessential amino acids, and penicillin (100 units/ml)/streptomycin (100 µg/ml). Recombinant CHO cells were grown in a complete medium with G418 (500 µg/ml). All cells were grown at 37° C. in 5% $CO_2$. Influenza A/Puerto Rico/8/34/H1N1 (PR8) virus was provided by Dr. Peter Palese (Icahn School of Medicine) and was amplified in 10- to 11-day-old embryonated chicken eggs and titrated by 50% endpoint dilution assay. The horseradish peroxidase (HRP)-conjugated streptavidin and anti-mouse IgG, IgG1, IgG2b, and IgG2c were obtained from Southern Biotech (Birmingham, Alabama). HA Abs were purchased from Santa Cruz Biotechnology (Santa Cruz, CA) or provided by Dr. Florian Krammer (Icahn School of Medicine) and Dr. Jeffrey Boyington (National Institutes of Health). Recombinant HA was purchased from Sino Biologicals (Shanghai, China) or from Biodefense and Emerging Infections Research Resources Repository (BEI Resources, Manassas, Va.). HIV gp120 specific IgG mAb B12 was also from BEI Resources.

ii. Construction of Influenza Virus HA-Fc Expression Plasmids

To make an IgG Fc fusion protein, a pCDNA3 plasmid encoding the hinge, CH2 and CH3 domains of mouse IgG2a Fc (56) served as a template for the Fc fragment. The rationale for using IgG2a is that it has the highest affinity for activating FcγRI, but the lowest affinity for FcγRIIB. In IgG2a Fc, the Glu318, Lys320, and Lys322 residues were replaced with Ala residues to remove the complement C1q binding site. In addition, to produce a mutant form of IgG Fc protein that cannot bind to FcRn, the His310/Gln311 (HQ) and His433/Asn434 (HN) residues were changed to Ala310/Asp311 (AD) and Ala433/Gln434 (AQ) residues, respectively, to eliminate FcRn binding sites (23).

To generate a trimeric HA that is fused to the Fc, the Cys224, Cys227, and Cys229 residues were converted to Ser residues within the Fc using a DNA mutagenesis kit (Clontech), resulting a monomeric Fc fragment. To make a trimeric HA-Fc fusion gene, the extracellular portion of PR8 HA, excluding the signal peptide sequence, was amplified by PCR from a plasmid containing full-length PR8 HA using the primer pair (5'-GGATCAGGCGGGGGTGGGTCCG-GAGGAGGTGGCTCGGGATCTG ACA CAATATGTATAGGCTACCATGC-3' (SEQ ID NO:16), 5'-CCTCTGGGCACCAGGCTTCTTGATCCTGAGCCT GATCCCTGATAGATCCCCATTGATTCC-3' (SEQ ID NO:17)). The IgG Fc antisense primer and the HA sense primer contain complementary glycine and serine codons to produce a 14GS linker to bridge the IgG Fc and HA fragments. A protein trimerization domain was amplified from a plasmid containing the T4 fibritin foldon sequence. Similarly, the HA antisense primer and the foldon sense primer contain complementary glycine and serine codons to introduce a 6GS linker between the HA and foldon fragments. The Fc, HA, and foldon fragments were fused by overlapping PCR and ligated into the pCDNA3 vector. All the resultant plasmids were confirmed by double-stranded DNA sequencing to verify the fidelity of PCR amplification and DNA cloning.

iii. SDS-PAGE Gel and Western Blotting

Protein concentration and quality were assessed by 8-12% SDS-PAGE gel under reducing and non-reducing conditions. Protein in gels was either stained with Coomassie blue dye or used for transferring onto nitrocellulose membranes (Schleicher & Schuell). The membranes were blocked with 5% milk in PBST (PBS and 0.05% Tween-20) and incubated overnight with anti-IgG2α-HRP (1:10,000) or anti-HA Abs (1:2000). For HA probing, membranes were further incubated with the anti-mouse IgG1-HRP Ab (1:5,000) for 2 hr. SuperSignal West Pico PLUS ECL substrate (Thermo Fisher) was used to visualize protein in membranes and images were developed and captured by the Chemi Doc XRS system (BioRad).

iv. Expression and Characterization of HA-Fc Fusion Proteins

The different HA-Fc plasmids were transfected into CHO cells using PolyJet reagent (SignaGen). Stable cell lines were selected and maintained under G418 (0.5-1 mg/ml). Expression and secretion of HA-Fc fusion proteins were determined by immunofluorescence assay, SDS-PAGE, and Western blotting analysis. The soluble HA-Fc proteins were produced by culturing CHO cells in complete medium containing 5% FBS with ultra-low IgG. The proteins were purified by Protein A column (Thermo Scientific) for the HA-Fc/wt protein and anti-mouse IgG (Rockland) conjugated agarose beads for the HA-Fc/mut protein. Protein concentrations were determined using NanoDrop spectrophotometer (Thermo Scientific).

The trimerization of HA-Fc was determined by the bis [sulfosuccinimidyl] suberate (BS3, Thermo Scientific) cross-linker method. Briefly, HA-Fc proteins (0.1 mg) were incubated with BS3 in 50-fold molar excess for 2 hr on ice. The reaction was then quenched by adding 1M Tris-HCl, pH 7.5 to a final concentration of 50 mM Tris-HCl and further incubated for 15 min at room temperature. The protein samples were subjected to electrophoresis and subsequently analyzed by Western blotting analysis with anti-HA and anti-IgG2a Abs in Western blotting.

v. FcRn Binding Assay

A FcRn binding assay was performed. CHO cells were either transfected with plasmids expressing mouse FcRn and β2m or mock-transfected. 24 hr later, the transfected cells were seeded in a 6-well plate for 6 hr. Cells were subsequently equilibrated with medium under either pH 6.0 or pH 7.4 condition at 4° C. for 30 min, then 3 µg trimeric HA-Fc/wt, HA-Fc/mut, or HA were added into each well or left untreated for 1 hr. The cells were washed with corresponding pH buffer to remove the unbound proteins. The cells were finally lysed in cold PBS (pH 6.0 or 7.4) with 0.5% CHAPS (Sigma-Aldrich) and protease inhibitor cocktail (Calbiochem) mixture on ice for 1 hr. The soluble proteins (10 µg) were subjected to Western blot analysis and blotted with biotin-labeled anti-HA primary Ab and Streptavidin-HRP-conjugated secondary Ab.

vi. Immunofluorescence Assay

Immunofluorescence was performed as previously described (56). Briefly, cells were grown on coverslips for 48 hr. The cells were rinsed with Hank's balanced salt solution (HBSS) and fixed with 4% paraformaldehyde (Sigma) in HBSS for 20 min and quenched with 100 mM glycine in PBS for 10 min. Cells were permeabilized with 0.2% Triton-X in HBSS for 5 min and incubated with blocking solution (3% normal goat serum in PBS) for 30 min. Cells were incubated with anti-HA Ab diluted in blocking solution for 2 hr. After washing, Alexa Fluor 555-conjugated anti-mouse IgG1 or IgG2a secondary Ab were added for 1 hr. Cells were washed with PBS and mounted to slides with ProLong Antifade solution (Thermo Scientific). Images were obtained using a Zeiss LSM 510 confocal microscope and analyzed by LSM Image Examiner software (Zeiss).

vii. Mouse Immunization and Virus Challenge

All the animal experiments were performed with the approval of the Institutional Animal Care and Use Committee. FcRn KO mice are a kind gift from Dr. Derry Roopenian (Jackson Laboratory). Six to eight-week-old C57BL/6 mice (Charles River Laboratory) and FcRn KO mice were intranasally (i.n.) immunized with 20 µl of 5 µg HA-Fc/wt, HA-Fc/mut, recombinant HA, or PBS. All vaccine proteins or PBS were mixed with 10 µg of CpG ODN 1826 (Invivogen). For intramuscular (i.m.) immunizations, mice were injected in the right hind leg with a 50-1 sample containing 5 µg HA-Fc/wt antigen admixed with 10 µg CpG. Two weeks later, the mice were boosted with the same vaccine formulations. The mice were i.n. infected with lethal doses (104 TCID50, equal to 5 MLD50) of the PR8 virus two weeks after the boost. For immunizations and challenge, all mice were anesthetized with an intraperitoneal (i.p.) injection of 200 µl of fresh Avertin (20 mg/ml, Fisher Scientific) and laid down on in a dorsal recumbent position to allow for recovery. After infection, mice were monitored daily for weight loss and other clinical signs of illness for 14 days. Animals that lost above 25% of their body weight on the day of infection or had become grossly moribund were euthanized.

viii. Collections of Bronchoalveolar Lavage (BAL) and Nasal Wash Fluids and Preparation of Single-Cell Suspensions from Tissues BAL and nasal wash fluids were collected 14 days after boost. Briefly, a small incision was made in the trachea. A syringe with a thin tube inserted at the tip was filled with PBS. The syringe was inserted first into the trachea towards the lungs and 1 ml of PBS was carefully injected into the lungs and by keeping the syringe in position, the PBS was retrieved back for the collection of BAL. For sampling the nasal wash, the syringe was similarly inserted into the trachea but towards the nasal cavity. PBS was carefully injected into the nasopharynx and collected when it flowed from the external nares. BAL and nasal wash fluids were then subjected to low-speed centrifugation and the supernatants were retained.

The single-cell suspensions from the mediastinal lymph nodes (MedLN) or spleen were made by mechanical abrasion of the organs. For isolation of cells from bone marrow, tibias and femurs were removed and the ends were clipped. The bone marrow was flushed out with RPMI1640. Isolation of single cells from the lung was performed as previously described (56). Briefly, after perfusion with 3 ml of PBS, lungs were minced and treated to enzymatic digestion in RPMI with pronase (1.5 mg/ml), Dispase (0.2%), and DNase (0.5 mg/ml) for 40 min at 37° C. with rotation. All cells from the MedLN, spleen, bone marrow and lung were filtered through a m nylon cell strainer and treated with red blood cell (RBC) lysis buffer (0.14 M NH4Cl, 0.017 M Tris-HCl at pH 7.2). All cells were washed and suspended in 2% FBS (Invitrogen) in PBS or RPMI1640 complete medium with 1-2% FBS. For each experiment, cells were pooled from 3-5 mice in each animal group.

ix. Intravenous In Vivo Ab Labeling and Flow Cytometry

For intravenous in vivo labeling of circulating T cells, mice were intravenously injected with 3 µg of PerCP-Cy5.5-conjugated anti-mouse CD3 D Ab. After 10 min, lungs were perfused with 3 ml of PBS and the single-cell suspensions were made as described above. Fc block (anti-mouse CD16/CD32, BD Biosciences, 1 µg/sample) was added to the lung and spleen cell samples and incubated for 30 min at 4° C. After wash with FACS buffer, cells were incubated with fluorescently-conjugated Abs to stain for T cell markers, CD3 (145-2C11), CD4 (RM4-5), CD8 (53-6.7), CD69 (H1.2F3), CD11a (2D7), and CD103 (M290), for 1 hr at 4° C. Isotype control Abs were included in each experiment. After washing, cells were suspended in 2% paraformaldehyde and analyzed using a FACSAria cytometer (BD Biosciences) and FlowJo software (Tree Star).

x. Intracellular Cytokine Staining

For determining T cell-derived cytokine levels, intracellular cytokine staining was performed as described (56). Briefly, single-cell suspensions from the lungs were stimulated with 2 µg of HA for 5 hr at 37° C. Cells were then incubated with GolgiStop (BD Biosciences) for an additional 5 hr. After wash, cells were incubated with Fc block and then stained with fluorescently-conjugated Abs for T cell surface markers, CD3, CD4, and CD8. Cells were fixed and permeabilized by incubating with BD CytoFix/Perm. After FACS buffer wash, cells were stained for cytokines IFN-γ and TNF-α. All block, incubation, and permeabilization steps were performed for 20 min at 4° C. After wash, cells were suspended in 2% paraformaldehyde and analyzed by flow cytometry as described above.

xi. Virus Titration and Pulmonary Pathology

Viral titers were determined by 50% endpoint dilution assay and hemagglutination assay as described (57, 58). Briefly, after challenge, mouse lungs were collected four days after lethal infection. Individual lungs were homogenized in the TissueLyser LT (Qiagen). After centrifuging the homogenates, the supernatants were serially diluted and incubated on MDCK cells for 1 hr. The supernatants were removed from cells and replaced with serum-free Opti-MEM with 1 µg/ml tosyl phenylalanyl chloromethyl ketone (TPCK)-treated trypsin. After incubation at 37° C. for 3 days, the supernatant (50 µl) was mixed with chicken RBC (50 µl) and incubated for 35 min. Samples were scored for agglutination and virus titers were calculated by the Reed-Muench method.

To examine the lung pathology, lungs were removed from at least three mice in each group and photographed to observe gross pathology. Lungs were then fixed in 10% formalin solution. The lungs were sectioned by American HistoLabs (Gaithersburg, MD) and stained with Hematoxylin and Eosin (H & E). To determine the level of pulmonary inflammation, the lung inflammations were scored in a blind manner by an independent collaborator.

xii. Enzyme-Linked Immunosorbent Assay (ELISA) and Enzyme-Linked Immunosorbent Spot (ELISpot).

For the detection of HA-specific Abs in serum, BAL fluid, and nasal washes, ELISA plates (Maxisorp, Nunc) were coated with 3 μg/ml of the HA-Fc protein or HA protein in coating buffer and incubated overnight at 4° C. For determination of the interaction between the HA-Fc and HA stalk-specific Abs, plates were coated with serially diluted mAbs, starting from 3 μg/ml. Plates were then washed three times with 0.05% Tween 20 in PBS (PBST) and blocked with 2% bovine serum albumin (BSA) in PBST for 1 hr at room temperature. Samples were serially diluted in 2% BSA-PBST or HA-Fc (0.5 μg/well) was added for 2 hr incubation. After washing 3 times, HRP-conjugated rabbit anti-mouse IgG Ab (1:20000, Pierce) or anti-mouse subclass-specific Ab (1:5000, Southern Biotech) was added. For use of biotin-labeled goat anti-mouse IgG-specific Fab (1:2,000), the streptavidin-RP (1:8000) was added. The reaction was visualized in a colorimetric assay using substrate tetramethyl benzidine (TMB) and analyzed using Victor III microplate reader (Perkin Elmer). Titers represent the highest dilution of samples showing a 2-fold increase over average OD450 nm values of negative controls.

For measuring HA-specific Ab-producing plasma cells, 96-well ELISpot plates (Millipore) were pre-wetted with 35% ethanol and washed with PBS. The plates were then coated with 5 μg/ml of HA protein overnight at 4° C. and blocked with RPMI 1640 complete medium with 10% FBS for 2 hr at 37° C. under 5% $CO_2$. Serial dilutions of single-cell suspensions from bone marrow were prepared in RPMI 1640 and added to the coated wells for 24 hr at 37° C. in 5% $CO_2$. After the incubation, the cells were removed, and the plates were washed 5 times with PBST, then incubated with biotin-labeled goat anti-mouse IgG-specific Fab Ab (1:2000) for 2 hr. After washing with PBST, the streptavidin-conjugated HRP (1:3000) was added and incubated for 1 hr. The samples were developed with 3-amino-9-ethylcarbazole (AEC) substrate (BD Biosciences). After washing, the plates were stored upside down in the dark to dry overnight at room temperature. Spots were counted with ELISpot reader and analyzed by ZellNet Consulting (New Jersey).

xiii. Microneutralization Assay

Neutralizing Abs were measured by a standard microneutralization assay on MDCK cells as previously described (59). Briefly, receptor destroying enzyme (RDE)-treated serum samples were serially diluted in PBS with 1×antibiotics/antimycotics. Then, 100 TCID50 of the PR8 virus was added to each well and incubated at 37° C. for 1 hr. MDCK cells were incubated with the serum/virus mixture for 1 hr at 37° C. After removing the mixture, serum-free Opti-MEM containing 1 μg/ml TPCK-treated trypsin was added to each well and incubated for 3 days at 37° C. Cytopathic effects (CPE) were observed daily and the presence of virus was determined by HA assay as described elsewhere. Neutralizing Ab titers were determined as the reciprocal of the highest serum dilution preventing the appearance of CPE. Each assay was done in triplicate. The average neutralizing Ab titer was determined for each immunization and control group.

xiv. Statistics Analysis.

To compare the Kaplan-Meier survival curves, we used multiple Mantel-Cox tests. Differences in Ab titers, cytokine percentages, virus titers, inflammation scores, and IgG-secreting cell numbers were assessed by using paired Student's two-tailed t-test or one-way ANOVA with Tukey's multiple comparison tests. GraphPad Prism 5.01 software was used for the statistical analyses.

Those skilled in the art will recognize, or be able to ascertain using no more than routine experimentation, many equivalents to the specific embodiments of the method and compositions described herein. Such equivalents are intended to be encompassed by the following claims.

We claim:

1. A peptide comprising
   a monomeric IgG Fc fragment of an immunoglobulin recognized by a neonatal receptor (FcRn), wherein the monomeric Fc fragment comprises one or more mutations in the CH2 domain, wherein the one or more mutations ablate C1q binding to the IgG Fc fragment, wherein the one or more mutations in the CH2 domain comprise a mutation of a Lys residue at a position that corresponds to amino acid 108 of SEQ ID NO:2;

an influenza HA protein comprising HA2; and a trimerization domain.

2. The peptide of claim 1, wherein the trimerization domain is a T4 fibritin trimerization domain.

3. The peptide of claim 2, wherein the T4 fibritin trimerization domain is foldon.

4. The peptide of claim 1, wherein the monomeric IgG Fc fragment of an immunoglobulin recognized by a FcRn is conjugated to the amino or carboxy terminal end of the influenza HA protein.

5. The peptide of claim 1 further comprising one or more linkers.

6. The peptide of claim 5, wherein at least one of the one or more linkers is between the influenza HA protein and the monomeric IgG Fc fragment of an immunoglobulin recognized by a FcRn.

7. The peptide of claim 5, wherein at least one of the one or more linkers is between the trimerization domain and the monomeric IgG Fc fragment of an immunoglobulin recognized by a FcRn.

8. The peptide of claim 5, wherein the one or more linkers comprises a GS-linker.

9. The peptide of claim 1, wherein the monomeric Fc fragment of an immunoglobulin recognized by a FcRn comprises one or more mutations in the cysteine residues responsible for dimer formation.

10. The peptide of claim 1, wherein the influenza HA protein is a non-cleavable HAO protein, wherein the non-cleavable HAO protein cannot be cleaved into HA1 and HA2.

11. The peptide of claim 10, wherein the non-cleavable HAO protein comprises mutations at the cleavage site of wild type HAO, wherein the mutations are SIQS→QRET, amino acids 321-325 of SEQ ID NO:6.

12. A composition comprising the peptide of claim 1.

13. The composition of claim 12, wherein the composition is a vaccine.

14. The composition of claim 12 further comprising a pharmaceutically acceptable carrier.

15. A nucleic acid sequence which encodes the peptide of claim 1.

16. A method for eliciting a protective immune response against influenza comprising administering to a subject an effective amount of a composition comprising the peptide of claim 1, wherein the administering is to a mucosal epithelium.

17. The method of claim 16, wherein the trimerization domain is a T4 fibritin trimerization domain.

18. The method of claim 16, wherein the mucosal epithelium is selected from the group consisting of: lungs, intestines, trachea, colon, nasal tissue, and vaginal tissue.

19. The method of claim 16, wherein the administering is intranasal administering.

20. The method of claim 16, wherein an adjuvant is further administered with the composition.

21. The method of claim 20, wherein the adjuvant is CpG or MPL.

22. A method of treating a subject exposed to influenza or at risk of being exposed to influenza comprising administering to the subject an effective amount of a composition comprising peptide of claim 1, wherein the administering is to a mucosal epithelium.

* * * * *